United States Patent
Jegla et al.

(10) Patent No.: US 7,893,209 B2
(45) Date of Patent: Feb. 22, 2011

(54) SLO2, NOVEL POTASSIUM CHANNEL PROTEINS FROM HUMAN BRAIN

(75) Inventors: Timothy James Jegla, Durham, NC (US); Julie Dickson Witzel, Raleigh, NC (US)

(73) Assignee: ICAgen, Inc., Durham, NC (US)

( * ) Notice: Subject to any disclaimer, the term of this patent is extended or adjusted under 35 U.S.C. 154(b) by 0 days.

(21) Appl. No.: 12/720,461

(22) Filed: Mar. 9, 2010

(65) Prior Publication Data

US 2010/0267930 A1  Oct. 21, 2010

Related U.S. Application Data

(60) Division of application No. 12/177,819, filed on Jul. 22, 2008, now Pat. No. 7,767,450, which is a division of application No. 11/325,764, filed on Jan. 4, 2006, now Pat. No. 7,411,043, which is a continuation of application No. 09/921,159, filed on Aug. 1, 2001, now Pat. No. 7,041,494.

(60) Provisional application No. 60/249,112, filed on Nov. 15, 2000.

(51) Int. Cl.
*C07K 14/705* (2006.01)
(52) U.S. Cl. ...................................................... 530/350
(58) Field of Classification Search ....................... None
See application file for complete search history.

(56) References Cited

U.S. PATENT DOCUMENTS 6,972,187 B2 * 12/2005 Curtis et al. ............... 435/69.1

* cited by examiner

*Primary Examiner*—Michael Pak
(74) *Attorney, Agent, or Firm*—Morgan Lewis & Bockius LLP

(57) ABSTRACT

The invention provides isolated nucleic acid and amino acid sequences of Slo2 and Slo4, members of the Slo family of potassium channel proteins, also known as "maxi" or BK potassium channel proteins. Also provided herein are antibodies to Slo2 and Slo 4, methods of detecting Slo2 and Slo 4, methods of screening for potassium channel activators and inhibitors using biologically active Slo2 and Slo 4, and kits for screening for activators and inhibitors of voltage-gated potassium channels comprising Slo2 and Slo 4.

7 Claims, 13 Drawing Sheets

```
  1   M-----ARAKLPRSPSE---------------------------------PAGAAAPEE  hSlo2
  1   M-----ARAKLPRSPSE---------------------------------GKAGPGGA-  rSLACK
  1   AREEGGGSHSLLPRVGSELPGRMPLPDGARTPGGVCREARGGGYTNRTFEFDDGQCAPR  KIAA1422

30   P-HGLSPLLPARG--GGSVGSDV----GQRLPVEDFSLDSSLSQ------VQEFFYVNENTFK  hSlo2
 30   P-HGLSPLLPTRG--GGSVGSDV----GQRLHVEDFSLDSSLSQ------VQEFFYVNENTFK  rSLACK
 61   PCAGDGALLDTAGFKMSDLDSEVLPLPPRYRFRDLLLGDPSFQNDDRVQVEFFYVNENTFKK  KIAA1422

80   ERLKLFFIKNQRSSLRIRLFNFSLKLLTCLLYIVRVLLDDPALGIGCWGCPKQNYSFNDS   hSlo2
 80   ERLKLFFIKNQRSSLRIRLFNFSLKLLTCLLYIVRVLLDNPDQGIGCWGCTKYNYTFNGS   rSLACK
121   ERLKLFFIKNQRSSLRIRLFNFSLKLLTCLLYIVRVLLDDPALGIGCWGCPKQNYSFNDS   KIAA1422

140   SSEINWAPILWVERKMTLWAIQVIVAIISPLETMLLIYLSYKGNIWEQIFRVSFVLEMIN   hSlo2
140   SSEFHWAPILWVERKMALWVIQVIVATISFLETMLLIYLSYKGNIWEQIFHVSFVLEMIN   rSLACK
181   SSEINWAPILWVERKMTLWAIQVIVAIISFLETMLLIYLSYKGNIWEQIFRVSFVLEMIN   KIAA1422

200   TLPFIITIFWPPLRNLFIPVFLNCWLAKHALENMINDFHRAILRTQSAMFNQVLILFCTL   hSlo2
200   TLPFIITITVFWPPLRNLFIPVFLNCWLAKHALENMINDFHRAILRTQSAMFNQVLILFCTL rSLACK
241   TLPFIITIFWPPLRNLFIPVFLNCWLAKHALENMINDFHRAILRTQSAMFNQVLILFCTL   KIAA1422

260   LCLVFTGTCGIQHLERAGENLSLLTSFYECIVTFSTVGYGDVTPKIWPSQLLVVIMICVA  hSlo2
260   LCLVFTGTCGIQHLERAGGNLNLLTSFYECIVTFSTVGFGDVTPKIWPSQLLVVILICVT  rSLACK
301   LCLVFTGTCGIQHLERAGENLSLLTSFYECIVTFSTVGYGDVTPKIWPSQLLVVIMICVA  KIAA1422

320   LVVLPLQFEEELVYLWMERQKSGGNYSRHRAQTEKHVVLCVSSLKIDLLMDFLNEFYAHPR  hSlo2
320   LVVLPLQFEEELVYLWMERQKSGGNYSRHRARTEKHVVLCVSSLKIDLLMDFLNEFYAHPR  rSLACK
361   LVVLPLQFEEELVYLWMERQKSGGNYSRHRAQTEKHVVLCVSSLKIDLLMDFLNEFYAHPR  KIAA1422

380   LQDYYVVILCPTEMDVQVRRVLQIPLWSQRVIYLQGSALKDQDLMRAKMDNGEACFILSS   hSlo2
380   LQDYYVVILCPSEMDVQVRRVLQIPLWSQRVIYLQGSALKDQDLMRAKMDNGEACFILSS   rSLACK
421   LQDYYVVILCPTEMDVQVRRVLQIPLWSQRVIYLQGSALKDQDLMRAKMDNGEACFILSS   KIAA1422

440   RNEVDRTAADHQTILRAWAVKDFAPNCPLYVQILKPENKFHVKFADHVVCEEECKYAMLA  hSlo2
440   RNEVDRTAADHQTILRAWAVKDFAPNCPLYVQILKPENKFHVKFADHVVCEEECKYAMLA  rSLACK
481   RNEVDRTAADHQTILRAWAVKDFAPNCPLYVQILKPENKFHVKFADHVVCEEECKYAMLA  KIAA1422
```

FIG. 1

```
500  LNCICPATSTLITLLVHTSRGQEGQESPEQWQRMYGRCSGNEVYHIRMGDSKFFREYEGK hSlo2
500  LNCICPATSTLITLLVHTSRGQEGQESPEQWQRMYGRCSGNEVYHIRMGDSKFFREYEGK rSLACK
541  LNCICPATSTLITLLVHTSRGQEGQESPEQWQRMYGRCSGNEVYHIRMGDSKFFREYEGK KIAA1422

560  SFTYAAFHAHKKYGVCLIGLKREDNKSILLNPGPRHILAASDTCFYINITKEENSAFIFK hSlo2
560  SFTYAAFHAHKKYGVCLIGLKREDNKSILLNPGPRHILAASDTCFYINITKEENSAFIFK rSLACK
601  SFTYAAFHAHKKYGVCLIGLKREENKSILLNPGPRHILAASDTCFYINITKEENSAFIFK KIAA1422

620  QEEKRKKRAFSGQGLHEGPARLPVHSIIASM--VAMDLQGTEHRPTQSGGGGGSKLALP  hSlo2
620  QEEKQNRRGLAGQALYEGPSRLPVHSIIASM--VAMDLQNTDCRPSQGGSGGGGKLTLP  rSLACK
661  QEEKRKKRAFSGQGLHEGPARLPVHSIIASMGTVAMDLQGTEHRPTQSGGGGGSKLALP  KIAA1422

678  TENGSGSRRPSIAPVLELADSSALLPCDLLSDQSEDEVTPSDDEGLSVVEYVKGYPPNSP hSlo2
678  TENGSGSRRPSIAPVLELADSSALLPCDLLSDQSEDEVTPSDDEGLSVVEYVKGYPPNSP rSLACK
722  TENGSGSRRPSIAPVLELADSSALLPCDLLSDQSEDEVTPSDDEGLSVVEYVKGYPPNSP KIAA1422

738  YIVSSPTLCHLLPVKAPFCCLRLDKGCKHNSYEDAKAYGFKNKLIIVSAETAGNGLYNFI hSlo2
738  YIGSSPTLCHLLPVKAPFCCLRLDKGCKHNSYEDAKAYGFKNKLIIVSAETAGNGLYNFI rSLACK
781  YIGSSPTLCHLLPVKAPFCCLRLDKGCKHNSYEDAKAYGFKNKLIIVSAETAGNGLYNFI KIAA1422

798  VPLRAYYRSRKELNPIVLLLDNKPDHHFLEAICCFPMVYYMEGSVDNLDSLLQCGIIYAD hSlo2
798  VPLRAYYRSRKELNPIVLLLDNKPDHHFLEAICCFPMVYYMEGSVDNLDSLLQCGIIYAD rSLACK
841  VPLRAYYRSRKELNPIVLLLDNKPDHHFLEAICCFPMVYYMEGSVDNLDSLLQCGIIYAD KIAA1422

858  NLVVVDKESTMSAEEDYMADAKTIVNVQTMFRLFPSLSITTELTHPSNMRFMQFRAKDSY hSlo2
858  NLVVVDKESTMSAEEDYMADAKTIVNVQTMFRLFPSLSITTELTHPSNMRFMQFRAKDSY rSLACK
901  NLVVVDKESTMSAEEDYMADAKTIVNVQTMFRLFPSLSITTELTHPSNMRFMQFRAKDSY KIAA1422

918  SLALSKLEKRERENGSNLAFMFRLPFAAGRVFSISMLDTLLYQSFVKDYMITITRLLLGL hSlo2
918  SLALSKLEKQERENGSNLAFMFRLPFAAGRVFSISMLDTLLYQSFVKDYMITITRLLLGL rSLACK
961  SLALSKLEKRERENGSNLAFMFRLPFAAGRVFSISMLDTLLYQSFVKDYMITITRLLLGL KIAA1422

978  DTTPGSGYLCAMKITEGDLWIRTYGRLFQKLCSSSAEIPIGIYRTESHVFSTSEPHDLRA hSlo2
978  DTTPGSGYLCAMKVTEDDLWIRTYGRLFQKLCSSSAEIPIGIYRTECHVFS-SEPHDLRA rSLACK
1021 DTTPGSGYLCAMKITEGDLWIRTYGRLFQKLCSSSAEIPIGIYRTESHVFSTSEPHDLRA KIAA1422
```

FIG. 1 (CONT.)

```
1038 QSQISVNVEDCEDTREVKGPWGSRAGTGGSS-QGRHTGGGDPAEHPLLRRKSLQWARRLS hSlo2
1037 QSQISVNMEDCEDTREAKGPWGTRAASGGGSTHGRHGGSADPVEHPLLRRKSLQWARKLS rSLACK
1081 QSQISVNVEDCEDTREVKGPWGSRAGTGGSS-QGRHTGGGDPAEHPLLRRKSLQWARRLS KIAA1422

1097 RKAPKQAGRAA-AAEWISQQRLSLYRRSERQELSELVKNRMKHLGLPTTGYEDVANLTAS hSlo2
1097 RKSSKQAGKAPMTTDWITQQRLSLYRRSERQELSELVKNRMKHLGLPTTGYEDVANLTAS rSLACK
1140 RKAPKQAGRAA-A                                                KIAA1422

1156 DVMNRVNLGYLQDEMNDH-QNTLSYVLINPPPDTRLEPSDIVYLIRSDPLAHVASSSQSR hSlo2
1157 DVMNRVNLGYLQDEMNDHHQNTLSYVLINPPPDTRLEPNDIVYLIRSDPLAHVTSSSQSR rSLACK
                                                                  KIAA1422

1215 KSSCCSHKLSSCNPETRDETQL hSlo2
1217 KSSCSNKLSSCNPETRDETQL  rSLACK
                            KIAA1422
```

FIG. 1 (CONT.)

```
  1  MV------------------DLESEVPPLPPRYRFRDLLL----GDQGWQNDDR------        Slo4
  1  MARAKLPRSPSEGKAGPGGAPAGAAAPEEPH-GLSPLLPARGGSVGSDVGQRLPVEDFS        Slo2

33  -----VQVEFYMNENTFKERLKLFFIKNQRSSLRIRLFNPSLKLLSCLLYIIRVLLEN        Slo4
 60  LDSSLSQVQVEFYVNENTFKERLKLFFIKNQRSSLRIRLFNPSLKLLTCLLYIVRVLLDD       Slo2

86  PSQGN-------------------EWSHIFWVNRSLPLWGLQVSVALISLFETILLGYLS       Slo4
120  PALGIGCWGCPKQNYSFNDSSSEINWAPILMVERKMTLWAIQVIVAIISFLETMLLIYLS       Slo2

127  YKGNIWEQILRIPFILEIINAVPFIISIFWPSLRNLFVPVFLNCWLAKHALENMINDLHR       Slo4
180  YKGNIWEQIFRVSRVLEMINTLPFIITIFWPPLRNLFIPVFLNCWLAKHALENMINDFHR       Slo2

187  AIQRTQSAMFNQVLILISTLLCLIFTCICGIQHLERIGKKLNLFDSLYFCIVTFSTVGFG       Slo4
240  AILRTQSAMFNQVLILFCTLLCLVFTGTCGIQHLERAGENLSLTSFYFCIVTFSTVGYG       Slo2

247  DVTPETWSSKLFVVAMICVALVVLPIQFEQLAYLWMERQKSGGNYSRHRAQTEKHVVLCV       Slo4
300  DVTPKIWPSQLLVVIMICVALVVLPLQFEELVYLWMERQKSGGNYSRHRAQTEKHVVLCV       Slo2

306  SSLKIDLLMDFLNEFYAHPRLQDYYVVILCPTEMDVQVRRVLQIPMWSQRVIYLQGSALK      Slo4
360  SSLKIDLLMDFLNEFYAHPRLQDYYVVILCPTEMDVQVRRVLQIPLWSQRVIYLQGSALK      Slo2

367  DQDLLRAKMDDAEACFILSSRCEVDRTSSDHQTILRAWAVKDFAPNCPLYVQILKPENKF      Slo4
420  DQDLMRAKMDNGEACFILSSRNEVDRTAADHQTILRAWAVKDFAPNCPLYVQILKPENKF      Slo2

427  HIKFADHVVCEEEFKYAMLALNCICPATSTLITLLVHTSRGQEGQQSPEQWQKMYGRCSG      Slo4
460  HVKFADHVVCEEECKYAMLALNCICPATSTLITLLVHTSRGQEGQESPEQWQRMYGRCSG      Slo2

487  NEVYHIVLEESTFFAEYEGKSFTYASFHAHKKFGVCLIGVRREDNKNILLNPGPRYIMNS      Slo4
540  NEVYHIRMGDSKFFREYEGKSFTYAAFHAHKKYGVCLIGLKREDNKSILLNPGPRHILAA      Slo2

547  TDICFYINITKEENSAF--KNQDQQRKSNVS-RSFYHGPSRLPVHSIIASMGTVAIDLQD      Slo4
600  SDTCFYINITKEENSAFIFKQEEKRKKRAFSGQGLHEGPARLPVHSIIASM--VAMDLQG      Slo2
```

FIG. 2

```
 604 TSCRSA------SGPTLSLPTEGSKEIRRPSIAPVLEVADTSSIQTCDLLSDQSEDETTP Slo4
 658 TEHRPTQSGGGGGSKLALPTENGSGSRRPSIAPVLELADSSALLPCDLLSDQSEDEVTP Slo2

658 -DEEMSSNLEYAKGYPPYSPYIGSSPTFCHLLHEKVPFCCLRLDKSCQHNYYEDAKAYGF Slo4
 718 SDDEGLSVVEYVKGYPPNSPYIVSSPTLCHLLPVKAPFCCLRLDKGCKHNSYEDAKAYGF Slo2

717 KNKLIIVAAETAGNGLYNFIVPLRAYYRPKKELNPIVLLLDNPPDMHFLDAICWFPMVYY Slo4
 778 KNKLIIVSAETAGNGLYNFIVPLRAYYRSRKELNPIVLLLDNKPDHHFLEAICCFPMVYY Slo2

777 MVGSIDNLDDLLRCGVTFAANMVVVDKESTMSAEEDYMADAKTIVNVQTLFRLFSSLSII Slo4
 838 MEGSVDNLDSLLQCGIIYADNLVVVDKESTMSAEEDYMADAKTIVNVQTMFRLFPSLSIT Slo2

837 TELTHPANMRFMQFRAKDCYSLALSKLEKKERERGSNLAFMFRLPFAAGRVFSISMLDTL Slo4
 898 TELTHPSNMRFMQFRAKDSYSLALSKLEKRERENGSNLAFMFRLPFAAGRVFSISMLDTL Slo2

897 LYQSFVKDYMISITRLLLGLDTTPGSGFLCSMKITADDLWIRTYARLYQKLCSSTGDVPI Slo4
 958 LYQSFVKDYMITITRLLLGLDTTPDSGYLCAMKITEGDLWIRTYGRLFQKLCSSSAEIPI Slo2

957 GIYRTESQKLTTSE------SQISISVEEWEDTKDSKEQGHHR------SNHRNSTSSD Slo4
1018 GIYRTESHVFSTSEPHDLRAQSQISVNVEDCEDTREVKGPWGSRAGTGGSSQGRHTGGGD Slo2

1004 QSDHPLLRRKSMQWARRLSRKGPKHSGKTA--EKITQQRLNLYRRSERQELAELVKNRMK Slo4
1078 PAEHPLLRRKSLQWARRLSRKAPKQAGRAAAAEWISQQRLSLYRRSERQELSELVKNRMK Slo2

1062 HLGLSTVGY-----------DEMNDHQSTLSYILINPSPDTRIELNDVVY Slo4
1138 HLGLPTTGYEDVANLTASDVMNRVNLGYLQDEMNDHQNTLSYVLINPPPDTRLEPSDIVY Slo2

1101 LIRPDPLAYLPNSEPSRRNSICNVT---GQDSREETQL.           Slo4
1198 LIRSDPLAHAVASSQSRKSS-CSHKLSSCNPETRDETQL.           Slo2
```

FIG. 2 (CONT.)

| | 1 | 2 | 3 | 4 | 5 | 6 | 7 | 8 | 9 | 10 | 11 | 12 |
|---|---|---|---|---|---|---|---|---|---|---|---|---|
| A | whole brain | cerebellum, left | substantia nigra | heart | esophagus | colon, transverse | kidney | lung | liver | leukemia, HL-60 | fetal brain | yeast total RNA |
| B | cerebral cortex | cerebellum, right | nucleus accumbens | aorta | stomach | colon, descending | skeletal muscle | placenta | pancreas | Hela | fetal heart | yeast tRNA |
| C | frontal lobe | corpus callosum | thalamus | atrium, left | duodenum | rectum | spleen | bladder | adrenal gland | leukemia, K-562 | fetal kidney | E. coli rRNA |
| D | parietal lobe | amygdala | pituitary gland | atrium, right | jejunum | | thymus | uterus | thyroid gland | leukemia, MOLT-4 | fetal liver | E. coli DNA |
| E | occipital lobe | caudate nucleus | spinal cord | ventricle, left | ileum | | peripheral blood leukocyte | prostate | salivary gland | Burkitt's lymphoma, Raji | fetal spleen | poly r(A) |
| F | temporal lobe | hippocampus | | ventricle, right | ileocecum | | lymph node | testis | mammary gland | Burkitt's lymphoma, Daudi | fetal thymus | human C₀r1 DNA |
| G | p.g.* of cerebral cortex | medulla oblongata | | inter-ventricular septum | appendix | | bone marrow | ovary | | colorectal adeno-carcinoma, SW480 | fetal lung | human DNA 100 mg |
| H | pons | putamen | | apex of the heart | colon, ascending | | trachea | | | lung carcinoma, A549 | | human DNA 500 mg |

Slo4 mRNA Dot Blot

\* paracontral gyrus

FIG. 7B

SEQUENCE LISTING

<160> NUMBER OF SEQ ID NOS: 38

<210> SEQ ID NO 1
<211> LENGTH: 3708
<212> TYPE: DNA
<213> ORGANISM: Homo sapiens
<220> FEATURE:
<221> NAME/KEY: CDS
<222> LOCATION: (1)..(3708)
<223> OTHER INFORMATION: human Slo2 potassium channel alpha subunit

<400> SEQUENCE: 1

```
atg gcg cgg gcc aag ctg ccg cgc tcg ccg tcc gag ggc aag gcg ggc        48
Met Ala Arg Ala Lys Leu Pro Arg Ser Pro Ser Glu Gly Lys Ala Gly
 1               5                  10                  15 ccg ggg ggc gcc cca gcc ggc gcc gca gcc ccc gag gag cct cac ggg        96
Pro Gly Gly Ala Pro Ala Gly Ala Ala Ala Pro Glu Glu Pro His Gly
             20                  25                  30 ctc agc ccg ctg ctg ccg gcc cgc ggc ggg ggc tcc gtg ggc agc gac       144
Leu Ser Pro Leu Leu Pro Ala Arg Gly Gly Gly Ser Val Gly Ser Asp
         35                  40                  45 gtg ggc cag agg ctt cct gta gaa gat ttc agc ctg gac tcc tcc ctg       192
Val Gly Gln Arg Leu Pro Val Glu Asp Phe Ser Leu Asp Ser Ser Leu
     50                  55                  60 tct cag gtc cag gtg gag ttc tac gtc aac gag aac acc ttc aag gag       240
Ser Gln Val Gln Val Glu Phe Tyr Val Asn Glu Asn Thr Phe Lys Glu
 65                  70                  75                  80 cgg ctc aag ctg ttc ttc atc aaa aac caa aga tcg agc ctg agg atc       288
Arg Leu Lys Leu Phe Phe Ile Lys Asn Gln Arg Ser Ser Leu Arg Ile
                 85                  90                  95 cgg ctg ttc aac ttc tcc ctg aag ctg ctc acc tgc ctg ctc tac att       336
Arg Leu Phe Asn Phe Ser Leu Lys Leu Leu Thr Cys Leu Leu Tyr Ile
            100                 105                 110 gtg cgc gtc ctg ctc gat gac ccg gcc ctg ggc atc gga tgc tgg ggc       384
Val Arg Val Leu Leu Asp Asp Pro Ala Leu Gly Ile Gly Cys Trp Gly
        115                 120                 125 tgc cca aag cag aac tac tcc ttc aat gac tcg tcc tcc gag atc aac       432
Cys Pro Lys Gln Asn Tyr Ser Phe Asn Asp Ser Ser Ser Glu Ile Asn
    130                 135                 140 tgg gct cct att ctg tgg gtg gag aga aag atg aca ctg tgg gcg atc       480
Trp Ala Pro Ile Leu Trp Val Glu Arg Lys Met Thr Leu Trp Ala Ile
145                 150                 155                 160 cag gtc atc gtg gcc ata ata agc ttc ctg gag acg atg ctt ctc atc       528
Gln Val Ile Val Ala Ile Ile Ser Phe Leu Glu Thr Met Leu Leu Ile
                165                 170                 175 tac ctc agc tac aaa ggc aac atc tgg gag cag atc ttc gcg gtg tcc       576
Tyr Leu Ser Tyr Lys Gly Asn Ile Trp Glu Gln Ile Phe Arg Val Ser
            180                 185                 190 ttc gtc ctg gag atg atc aac act ctg ccc ttc atc atc acg atc ttc       624
Phe Val Leu Glu Met Ile Asn Thr Leu Pro Phe Ile Ile Thr Ile Phe
        195                 200                 205 tgg ccg ccg ctg cgg aac ctg ttc atc ccc gtc ttt ctg aac tgc tgg       672
Trp Pro Pro Leu Arg Asn Leu Phe Ile Pro Val Phe Leu Asn Cys Trp
    210                 215                 220 ctg gcc aag cac gcg ctg gaa aac atg att aat gac ttc cac cgt gcc       720
Leu Ala Lys His Ala Leu Glu Asn Met Ile Asn Asp Phe His Arg Ala
225                 230                 235                 240 atc ctg cgg aca cag tca gcc atg ttc aac cag gtc ctc atc ctc ttc       768
Ile Leu Arg Thr Gln Ser Ala Met Phe Asn Gln Val Leu Ile Leu Phe
                245                 250                 255
```

-continued

```
tgc acc ctg ctg tgc ctc gtt ttc acg ggg acc tgc ggc atc cag cac        816
Cys Thr Leu Leu Cys Leu Val Phe Thr Gly Thr Cys Gly Ile Gln His
        260                 265                 270 ctg gag cgg gcg ggc gag aac ctg tcc ctc ctg acc tcc ttc tac ttc        864
Leu Glu Arg Ala Gly Glu Asn Leu Ser Leu Leu Thr Ser Phe Tyr Phe
            275                 280                 285 tgc atc gtc acc ttc tcc acc gtg ggc tac ggt gac gtc acg ccc aag        912
Cys Ile Val Thr Phe Ser Thr Val Gly Tyr Gly Asp Val Thr Pro Lys
290                 295                 300 atc tgg cca tcg cag ctg ctg gtg gtc atc atg atc tgc gtg gcc ctc        960
Ile Trp Pro Ser Gln Leu Leu Val Val Ile Met Ile Cys Val Ala Leu
305                 310                 315                 320 gtg gtg ctc cca ctg cag ttc gag gag ctc gtc tac ctc tgg atg gag       1008
Val Val Leu Pro Leu Gln Phe Glu Glu Leu Val Tyr Leu Trp Met Glu
                325                 330                 335 cgg cag aag tca ggg ggc aac tac agc cgc cac cgt gcg cag acg gag       1056
Arg Gln Lys Ser Gly Gly Asn Tyr Ser Arg His Arg Ala Gln Thr Glu
            340                 345                 350 aag cac gtg gtc ctg tgt gtc agc tcc ctc aag atc gac ctt ctc atg       1104
Lys His Val Val Leu Cys Val Ser Ser Leu Lys Ile Asp Leu Leu Met
        355                 360                 365 gac ttc ctg aac gag ttc tac gcc cac ccc cgg ctc cag gac tat tac       1152
Asp Phe Leu Asn Glu Phe Tyr Ala His Pro Arg Leu Gln Asp Tyr Tyr
370                 375                 380 gtg gtc atc ctg tgc ccc acg gag atg gat gtc cag gtg cgc aga gtc       1200
Val Val Ile Leu Cys Pro Thr Glu Met Asp Val Gln Val Arg Arg Val
385                 390                 395                 400 ctg cag atc cct ctg tgg tcc cag cgg gtc atc tac ctc cag ggc tct       1248
Leu Gln Ile Pro Leu Trp Ser Gln Arg Val Ile Tyr Leu Gln Gly Ser
                405                 410                 415 gca ctc aaa gac cag gac ctc atg cga gcc aag atg gac aat ggg gag       1296
Ala Leu Lys Asp Gln Asp Leu Met Arg Ala Lys Met Asp Asn Gly Glu
            420                 425                 430 gcc tgc ttc atc ctc agc agc agg aac gag gtg gac cgc acg gct gca       1344
Ala Cys Phe Ile Leu Ser Ser Arg Asn Glu Val Asp Arg Thr Ala Ala
        435                 440                 445 gac cac cag acc atc ctg cgc gcc tgg gcc gtg aag gac ttc gcc ccc       1392
Asp His Gln Thr Ile Leu Arg Ala Trp Ala Val Lys Asp Phe Ala Pro
450                 455                 460 aac tgc ccc ctc tac gtc cag atc ctc aaa cct gaa aac aag ttt cac       1440
Asn Cys Pro Leu Tyr Val Gln Ile Leu Lys Pro Glu Asn Lys Phe His
465                 470                 475                 480 gtc aag ttt gct gac cac gtg gtg tgt gag gag gag tgc aag tac gcc       1488
Val Lys Phe Ala Asp His Val Val Cys Glu Glu Glu Cys Lys Tyr Ala
                485                 490                 495 atg ctg gcg ctg aac tgc atc tgc ccg gcg acc tcc acc ctc atc acc       1536
Met Leu Ala Leu Asn Cys Ile Cys Pro Ala Thr Ser Thr Leu Ile Thr
            500                 505                 510 ctg ctg gtg cac acg tcc cgc ggc cag gag gga cag gag tct ccg gag       1584
Leu Leu Val His Thr Ser Arg Gly Gln Glu Gly Gln Glu Ser Pro Glu
        515                 520                 525 cag tgg cag cgc atg tat ggg cgc tgc tcc ggc aac gag gtg tac cac       1632
Gln Trp Gln Arg Met Tyr Gly Arg Cys Ser Gly Asn Glu Val Tyr His
530                 535                 540 atc cgc atg ggt gac agc aag ttc ttc cgc gag tac gag ggc aag agc       1680
Ile Arg Met Gly Asp Ser Lys Phe Phe Arg Glu Tyr Glu Gly Lys Ser
545                 550                 555                 560 ttc acc tac gcg gcc ttc cac gcc cac aag aag tat ggc gtg tgc ctc       1728
Phe Thr Tyr Ala Ala Phe His Ala His Lys Lys Tyr Gly Val Cys Leu
```

```
                    565                 570                 575
atc ggg ctg aag cgg gag gac aac aag agc atc ctg ctg aac ccg ggg       1776
Ile Gly Leu Lys Arg Glu Asp Asn Lys Ser Ile Leu Leu Asn Pro Gly
            580                 585                 590 ccc cgg cac atc ctg gcc gcc tct gac acc tgc ttc tac atc aac atc       1824
Pro Arg His Ile Leu Ala Ala Ser Asp Thr Cys Phe Tyr Ile Asn Ile
        595                 600                 605 acc aag gag gag aac tcg gcc ttc atc ttc aag cag gag gag aag cgg       1872
Thr Lys Glu Glu Asn Ser Ala Phe Ile Phe Lys Gln Glu Glu Lys Arg
    610                 615                 620 aag aag agg gcc ttc tcg ggg cag ggg ctg cac gag ggt ccg gcc cgc       1920
Lys Lys Arg Ala Phe Ser Gly Gln Gly Leu His Glu Gly Pro Ala Arg
625                 630                 635                 640 ctg ccc gtg cac agc atc atc gcc tcc atg gtg gcc atg gac ctg cag       1968
Leu Pro Val His Ser Ile Ile Ala Ser Met Val Ala Met Asp Leu Gln
                645                 650                 655 ggc aca gag cac cgg cct acg cag agc ggc ggt ggg ggc ggg ggc agc       2016
Gly Thr Glu His Arg Pro Thr Gln Ser Gly Gly Gly Gly Gly Gly Ser
            660                 665                 670 aag ctg gca ctg ccc acg gag aac ggc tcg ggc agc cgg cgg ccc agc       2064
Lys Leu Ala Leu Pro Thr Glu Asn Gly Ser Gly Ser Arg Arg Pro Ser
        675                 680                 685 atc gcg ccc gtc ctg gaa ctg gcc gac agc tca gcc ctg ctg ccc tgc       2112
Ile Ala Pro Val Leu Glu Leu Ala Asp Ser Ser Ala Leu Leu Pro Cys
    690                 695                 700 gac ctg ctg agc gac cag tcg gag gat gag gtg acg ccg tcg gac gac       2160
Asp Leu Leu Ser Asp Gln Ser Glu Asp Glu Val Thr Pro Ser Asp Asp
705                 710                 715                 720 gag ggg ctc tcc gtg gta gag tat gtg aag ggc tac cct ccc aac tcg       2208
Glu Gly Leu Ser Val Val Glu Tyr Val Lys Gly Tyr Pro Pro Asn Ser
                725                 730                 735 ccc tac atc gtc agc tcc cca acc ctg tgc cac ctc ctg cct gtg aaa       2256
Pro Tyr Ile Val Ser Ser Pro Thr Leu Cys His Leu Leu Pro Val Lys
            740                 745                 750 gcc ccc ttc tgc tgc ctg cgg ctg gac aag ggc tgc aag cac aac agc       2304
Ala Pro Phe Cys Cys Leu Arg Leu Asp Lys Gly Cys Lys His Asn Ser
        755                 760                 765 tat gaa gac gcc aag gcc tac ggg ttc aag aac aag ctg atc atc gtc       2352
Tyr Glu Asp Ala Lys Ala Tyr Gly Phe Lys Asn Lys Leu Ile Ile Val
    770                 775                 780 tcg gca gag acg gcc ggc aat ggg ctg tac aac ttc atc gtg cca ctg       2400
Ser Ala Glu Thr Ala Gly Asn Gly Leu Tyr Asn Phe Ile Val Pro Leu
785                 790                 795                 800 cgg gcc tac tac aga tcc cgc aag gag ctg aac ccc atc gtg ctg ctg       2448
Arg Ala Tyr Tyr Arg Ser Arg Lys Glu Leu Asn Pro Ile Val Leu Leu
                805                 810                 815 ctg gac aac aag ccc gac cac cac ttc ctg gaa gcc atc tgc tgc ttc       2496
Leu Asp Asn Lys Pro Asp His His Phe Leu Glu Ala Ile Cys Cys Phe
            820                 825                 830 ccc atg gtc tac tac atg gag ggc tct gtg gac aac ctg gac agc ctg       2544
Pro Met Val Tyr Tyr Met Glu Gly Ser Val Asp Asn Leu Asp Ser Leu
        835                 840                 845 ctg cag tgt ggc atc atc tat gcg gac aac ctg gtg gtg gtg gac aag       2592
Leu Gln Cys Gly Ile Ile Tyr Ala Asp Asn Leu Val Val Val Asp Lys
    850                 855                 860 gag agc acc atg agc gcc gag gag gac tac atg gcg gac gcc aag acc       2640
Glu Ser Thr Met Ser Ala Glu Glu Asp Tyr Met Ala Asp Ala Lys Thr
865                 870                 875                 880 atc gtc aac gtg cag acc atg ttc cgg ctc ttc ccc agc ctc agc atc       2688
```

```
Ile Val Asn Val Gln Thr Met Phe Arg Leu Phe Pro Ser Leu Ser Ile
            885                 890                 895 acc acg gag ctc acc cac cct tcc aac atg cgc ttc atg cag ttc cgc      2736
Thr Thr Glu Leu Thr His Pro Ser Asn Met Arg Phe Met Gln Phe Arg
        900                 905                 910 gcc aag gac agc tac tct ctg gct ctt tcc aaa cta gaa aag agg gag      2784
Ala Lys Asp Ser Tyr Ser Leu Ala Leu Ser Lys Leu Glu Lys Arg Glu
        915                 920                 925 cga gag aat ggc tcc aac ctg gcc ttc atg ttc cgc ctg ccg ttc gcc      2832
Arg Glu Asn Gly Ser Asn Leu Ala Phe Met Phe Arg Leu Pro Phe Ala
    930                 935                 940 gcc ggc cgc gtc ttc agc atc agc atg ttg gac aca ctg ctc tac cag      2880
Ala Gly Arg Val Phe Ser Ile Ser Met Leu Asp Thr Leu Leu Tyr Gln
945                 950                 955                 960 tcc ttc gtg aag gac tac atg atc acc atc acc cgg ctg ctg ctg ggc      2928
Ser Phe Val Lys Asp Tyr Met Ile Thr Ile Thr Arg Leu Leu Leu Gly
                965                 970                 975 ctg gac acc acg ccg ggc tcg ggg tac ctc tgt gcc atg aaa atc acc      2976
Leu Asp Thr Thr Pro Gly Ser Gly Tyr Leu Cys Ala Met Lys Ile Thr
            980                 985                 990 gag ggc gac ctg tgg atc cgc acg tac ggc cgc ctc ttc cag aag ctc      3024
Glu Gly Asp Leu Trp Ile Arg Thr Tyr Gly Arg Leu Phe Gln Lys Leu
        995                 1000                1005 tgc tcc tcc agc gcc gag atc ccc att ggc atc tac cgg aca gag agc      3072
Cys Ser Ser Ser Ala Glu Ile Pro Ile Gly Ile Tyr Arg Thr Glu Ser
    1010                1015                1020 cac gtc ttc tcc acc tcg gag ccc cac gac ctc aga gcc cag tcc cag      3120
His Val Phe Ser Thr Ser Glu Pro His Asp Leu Arg Ala Gln Ser Gln
1025                1030                1035                1040 atc tcg gtg aac gtg gag gac tgt gag gac aca cgg gaa gtg aag ggg      3168
Ile Ser Val Asn Val Glu Asp Cys Glu Asp Thr Arg Glu Val Lys Gly
                1045                1050                1055 ccc tgg ggc tcc cgc gct ggc acc gga ggc agc tcc cag ggc cgc cac      3216
Pro Trp Gly Ser Arg Ala Gly Thr Gly Gly Ser Ser Gln Gly Arg His
            1060                1065                1070 acg ggc ggc ggt gac ccc gca gag cac cca ctg cta cgg cgc aag agc      3264
Thr Gly Gly Gly Asp Pro Ala Glu His Pro Leu Leu Arg Arg Lys Ser
        1075                1080                1085 ctg cag tgg gcc cgg agg ctg agc cgc aag gcg ccc aag cag gca ggc      3312
Leu Gln Trp Ala Arg Arg Leu Ser Arg Lys Ala Pro Lys Gln Ala Gly
    1090                1095                1100 cgg gcg gcg gcc gcg gag tgg atc agc cag cag cgc ctc agc ctg tac      3360
Arg Ala Ala Ala Ala Glu Trp Ile Ser Gln Gln Arg Leu Ser Leu Tyr
1105                1110                1115                1120 cgg cgc tct gag cgc cag gag ctc tcc gag ctg gtg aag aac cgc atg      3408
Arg Arg Ser Glu Arg Gln Glu Leu Ser Glu Leu Val Lys Asn Arg Met
                1125                1130                1135 aag cac ctg ggg ctg ccc acc acc ggc tac gag gac gta gca aat tta      3456
Lys His Leu Gly Leu Pro Thr Thr Gly Tyr Glu Asp Val Ala Asn Leu
            1140                1145                1150 aca gcc agt gat gtc atg aat cgg gta aac ctg gga tat ttg caa gac      3504
Thr Ala Ser Asp Val Met Asn Arg Val Asn Leu Gly Tyr Leu Gln Asp
        1155                1160                1165 gag atg aac gac cac cag aac acc ctc tcc tac gtc ctc atc aac cct      3552
Glu Met Asn Asp His Gln Asn Thr Leu Ser Tyr Val Leu Ile Asn Pro
    1170                1175                1180 ccg ccc gac acg agg ctg gag ccc agt gac att gtc tat ctc atc cgc      3600
Pro Pro Asp Thr Arg Leu Glu Pro Ser Asp Ile Val Tyr Leu Ile Arg
1185                1190                1195                1200
```

-continued

```
tcc gac ccc ctg gct cac gtg gcc agc agc tcc cag agc cgg aag agc    3648
Ser Asp Pro Leu Ala His Val Ala Ser Ser Ser Gln Ser Arg Lys Ser
            1205                1210                1215 agc tgc agc cac aag ctg tcg tcc tgc aac ccc gag act cgc gac gag    3696
Ser Cys Ser His Lys Leu Ser Ser Cys Asn Pro Glu Thr Arg Asp Glu
        1220                1225                1230 aca cag ctc taa                                                     3708
Thr Gln Leu
        1235

<210> SEQ ID NO 2
<211> LENGTH: 1235
<212> TYPE: PRT
<213> ORGANISM: Homo sapiens
<220> FEATURE:
<223> OTHER INFORMATION: human Slo2 potassium channel alpha subunit

<400> SEQUENCE: 2

Met Ala Arg Ala Lys Leu Pro Arg Ser Pro Ser Glu Gly Lys Ala Gly
  1               5                  10                  15

Pro Gly Gly Ala Pro Ala Gly Ala Ala Ala Pro Glu Glu Pro His Gly
             20                  25                  30

Leu Ser Pro Leu Leu Pro Ala Arg Gly Gly Gly Ser Val Gly Ser Asp
         35                  40                  45

Val Gly Gln Arg Leu Pro Val Glu Asp Phe Ser Leu Asp Ser Ser Leu
     50                  55                  60

Ser Gln Val Gln Val Glu Phe Tyr Val Asn Glu Asn Thr Phe Lys Glu
 65                  70                  75                  80

Arg Leu Lys Leu Phe Phe Ile Lys Asn Gln Arg Ser Ser Leu Arg Ile
                 85                  90                  95

Arg Leu Phe Asn Phe Ser Leu Lys Leu Leu Thr Cys Leu Leu Tyr Ile
            100                 105                 110

Val Arg Val Leu Leu Asp Asp Pro Ala Leu Gly Ile Gly Cys Trp Gly
        115                 120                 125

Cys Pro Lys Gln Asn Tyr Ser Phe Asn Asp Ser Ser Ser Glu Ile Asn
    130                 135                 140

Trp Ala Pro Ile Leu Trp Val Glu Arg Lys Met Thr Leu Trp Ala Ile
145                 150                 155                 160

Gln Val Ile Val Ala Ile Ile Ser Phe Leu Glu Thr Met Leu Leu Ile
                165                 170                 175

Tyr Leu Ser Tyr Lys Gly Asn Ile Trp Glu Gln Ile Phe Arg Val Ser
            180                 185                 190

Phe Val Leu Glu Met Ile Asn Thr Leu Pro Phe Ile Ile Thr Ile Phe
        195                 200                 205

Trp Pro Pro Leu Arg Asn Leu Phe Ile Pro Val Phe Leu Asn Cys Trp
    210                 215                 220

Leu Ala Lys His Ala Leu Glu Asn Met Ile Asn Asp Phe His Arg Ala
225                 230                 235                 240

Ile Leu Arg Thr Gln Ser Ala Met Phe Asn Gln Val Leu Ile Leu Phe
                245                 250                 255

Cys Thr Leu Leu Cys Leu Val Phe Thr Gly Thr Cys Gly Ile Gln His
            260                 265                 270

Leu Glu Arg Ala Gly Glu Asn Leu Ser Leu Leu Thr Ser Phe Tyr Phe
        275                 280                 285

Cys Ile Val Thr Phe Ser Thr Val Gly Tyr Gly Asp Val Thr Pro Lys
    290                 295                 300
```

```
Ile Trp Pro Ser Gln Leu Leu Val Val Ile Met Ile Cys Val Ala Leu
305                 310                 315                 320

Val Val Leu Pro Leu Gln Phe Glu Glu Leu Val Tyr Leu Trp Met Glu
            325                 330                 335

Arg Gln Lys Ser Gly Gly Asn Tyr Ser Arg His Arg Ala Gln Thr Glu
            340                 345                 350

Lys His Val Val Leu Cys Val Ser Ser Leu Lys Ile Asp Leu Leu Met
            355                 360                 365

Asp Phe Leu Asn Glu Phe Tyr Ala His Pro Arg Leu Gln Asp Tyr Tyr
    370                 375                 380

Val Val Ile Leu Cys Pro Thr Glu Met Asp Val Gln Val Arg Arg Val
385                 390                 395                 400

Leu Gln Ile Pro Leu Trp Ser Gln Arg Val Ile Tyr Leu Gln Gly Ser
                405                 410                 415

Ala Leu Lys Asp Gln Asp Leu Met Arg Ala Lys Met Asp Asn Gly Glu
            420                 425                 430

Ala Cys Phe Ile Leu Ser Ser Arg Asn Glu Val Asp Arg Thr Ala Ala
            435                 440                 445

Asp His Gln Thr Ile Leu Arg Ala Trp Ala Val Lys Asp Phe Ala Pro
    450                 455                 460

Asn Cys Pro Leu Tyr Val Gln Ile Leu Lys Pro Glu Asn Lys Phe His
465                 470                 475                 480

Val Lys Phe Ala Asp His Val Val Cys Glu Glu Cys Lys Tyr Ala
                485                 490                 495

Met Leu Ala Leu Asn Cys Ile Cys Pro Ala Thr Ser Thr Leu Ile Thr
            500                 505                 510

Leu Leu Val His Thr Ser Arg Gly Gln Glu Gly Gln Glu Ser Pro Glu
            515                 520                 525

Gln Trp Gln Arg Met Tyr Gly Arg Cys Ser Gly Asn Glu Val Tyr His
    530                 535                 540

Ile Arg Met Gly Asp Ser Lys Phe Phe Arg Glu Tyr Glu Gly Lys Ser
545                 550                 555                 560

Phe Thr Tyr Ala Ala Phe His Ala His Lys Lys Tyr Gly Val Cys Leu
                565                 570                 575

Ile Gly Leu Lys Arg Glu Asp Asn Lys Ser Ile Leu Leu Asn Pro Gly
            580                 585                 590

Pro Arg His Ile Leu Ala Ala Ser Asp Thr Cys Phe Tyr Ile Asn Ile
            595                 600                 605

Thr Lys Glu Glu Asn Ser Ala Phe Ile Phe Lys Gln Glu Glu Lys Arg
    610                 615                 620

Lys Lys Arg Ala Phe Ser Gly Gln Gly Leu His Glu Gly Pro Ala Arg
625                 630                 635                 640

Leu Pro Val His Ser Ile Ile Ala Ser Met Val Ala Met Asp Leu Gln
                645                 650                 655

Gly Thr Glu His Arg Pro Thr Gln Ser Gly Gly Gly Gly Gly Gly Ser
            660                 665                 670

Lys Leu Ala Leu Pro Thr Glu Asn Gly Ser Gly Ser Arg Arg Pro Ser
            675                 680                 685

Ile Ala Pro Val Leu Glu Leu Ala Asp Ser Ser Ala Leu Leu Pro Cys
    690                 695                 700

Asp Leu Leu Ser Asp Gln Ser Glu Asp Glu Val Thr Pro Ser Asp Asp
705                 710                 715                 720

Glu Gly Leu Ser Val Val Glu Tyr Val Lys Gly Tyr Pro Pro Asn Ser
```

-continued

```
                725                 730                 735
Pro Tyr Ile Val Ser Ser Pro Thr Leu Cys His Leu Pro Val Lys
            740                 745                 750
Ala Pro Phe Cys Cys Leu Arg Leu Asp Lys Gly Cys Lys His Asn Ser
            755                 760                 765
Tyr Glu Asp Ala Lys Ala Tyr Gly Phe Lys Asn Lys Leu Ile Ile Val
            770                 775                 780
Ser Ala Glu Thr Ala Gly Asn Gly Leu Tyr Asn Phe Ile Val Pro Leu
785                 790                 795                 800
Arg Ala Tyr Tyr Arg Ser Arg Lys Glu Leu Asn Pro Ile Val Leu Leu
                805                 810                 815
Leu Asp Asn Lys Pro Asp His His Phe Leu Glu Ala Ile Cys Cys Phe
            820                 825                 830
Pro Met Val Tyr Tyr Met Glu Gly Ser Val Asp Asn Leu Asp Ser Leu
            835                 840                 845
Leu Gln Cys Gly Ile Ile Tyr Ala Asp Asn Leu Val Val Asp Lys
            850                 855                 860
Glu Ser Thr Met Ser Ala Glu Glu Asp Tyr Met Ala Asp Ala Lys Thr
865                 870                 875                 880
Ile Val Asn Val Gln Thr Met Phe Arg Leu Phe Pro Ser Leu Ser Ile
                885                 890                 895
Thr Thr Glu Leu Thr His Pro Ser Asn Met Arg Phe Met Gln Phe Arg
            900                 905                 910
Ala Lys Asp Ser Tyr Ser Leu Ala Leu Ser Lys Leu Glu Lys Arg Glu
            915                 920                 925
Arg Glu Asn Gly Ser Asn Leu Ala Phe Met Phe Arg Leu Pro Phe Ala
            930                 935                 940
Ala Gly Arg Val Phe Ser Ile Ser Met Leu Asp Thr Leu Leu Tyr Gln
945                 950                 955                 960
Ser Phe Val Lys Asp Tyr Met Ile Thr Ile Thr Arg Leu Leu Leu Gly
                965                 970                 975
Leu Asp Thr Thr Pro Gly Ser Gly Tyr Leu Cys Ala Met Lys Ile Thr
            980                 985                 990
Glu Gly Asp Leu Trp Ile Arg Thr Tyr Gly Arg Leu Phe Gln Lys Leu
            995                 1000                1005
Cys Ser Ser Ser Ala Glu Ile Pro Ile Gly Ile Tyr Arg Thr Glu Ser
    1010                1015                1020
His Val Phe Ser Thr Ser Glu Pro His Asp Leu Arg Ala Gln Ser Gln
1025                1030                1035                1040
Ile Ser Val Asn Val Glu Asp Cys Glu Asp Thr Arg Glu Val Lys Gly
                1045                1050                1055
Pro Trp Gly Ser Arg Ala Gly Thr Gly Gly Ser Ser Gln Gly Arg His
            1060                1065                1070
Thr Gly Gly Gly Asp Pro Ala Glu His Pro Leu Leu Arg Arg Lys Ser
            1075                1080                1085
Leu Gln Trp Ala Arg Arg Leu Ser Arg Lys Ala Pro Lys Gln Ala Gly
            1090                1095                1100
Arg Ala Ala Ala Ala Glu Trp Ile Ser Gln Gln Arg Leu Ser Leu Tyr
1105                1110                1115                1120
Arg Arg Ser Glu Arg Gln Glu Leu Ser Glu Leu Val Lys Asn Arg Met
                1125                1130                1135
Lys His Leu Gly Leu Pro Thr Thr Gly Tyr Glu Asp Val Ala Asn Leu
            1140                1145                1150
```

-continued

```
Thr Ala Ser Asp Val Met Asn Arg Val Asn Leu Gly Tyr Leu Gln Asp
       1155                1160                1165

Glu Met Asn Asp His Gln Asn Thr Leu Ser Tyr Val Leu Ile Asn Pro
   1170                1175                1180

Pro Pro Asp Thr Arg Leu Glu Pro Ser Asp Ile Val Tyr Leu Ile Arg
1185                1190                1195                1200

Ser Asp Pro Leu Ala His Val Ala Ser Ser Ser Gln Ser Arg Lys Ser
               1205                1210                1215

Ser Cys Ser His Lys Leu Ser Ser Cys Asn Pro Glu Thr Arg Asp Glu
           1220                1225                1230

Thr Gln Leu
       1235

<210> SEQ ID NO 3
<211> LENGTH: 3408
<212> TYPE: DNA
<213> ORGANISM: Homo sapiens
<220> FEATURE:
<221> NAME/KEY: CDS
<222> LOCATION: (1)..(3408)
<223> OTHER INFORMATION: human Slo4 potassium channel alpha subunit

<400> SEQUENCE: 3 atg gtt gat ttg gag agc gaa gtg ccc cct ctg cct ccc agg tac agg      48
Met Val Asp Leu Glu Ser Glu Val Pro Pro Leu Pro Pro Arg Tyr Arg
  1               5                  10                  15 ttt cga gat ttg ctg cta ggg gac caa gga tgg caa aac gac gac agg      96
Phe Arg Asp Leu Leu Leu Gly Asp Gln Gly Trp Gln Asn Asp Asp Arg
             20                  25                  30 gta caa gtt gaa ttc tat atg aat gaa aat aca ttt aaa gaa aga cta     144
Val Gln Val Glu Phe Tyr Met Asn Glu Asn Thr Phe Lys Glu Arg Leu
         35                  40                  45 aaa tta ttt ttc ata aaa aac cag aga tca agt cta agg ata cgc ctg     192
Lys Leu Phe Phe Ile Lys Asn Gln Arg Ser Ser Leu Arg Ile Arg Leu
     50                  55                  60 ttc aat ttt tct ctc aaa tta cta agc tgc tta tta tac ata atc cga     240
Phe Asn Phe Ser Leu Lys Leu Leu Ser Cys Leu Leu Tyr Ile Ile Arg
 65                  70                  75                  80 gta cta cta gaa aac cct tca caa gga aat gaa tgg tct cat atc ttt     288
Val Leu Leu Glu Asn Pro Ser Gln Gly Asn Glu Trp Ser His Ile Phe
                 85                  90                  95 tgg gtg aac aga agt cta cct ttg tgg ggc tta cag gtt tca gtg gca     336
Trp Val Asn Arg Ser Leu Pro Leu Trp Gly Leu Gln Val Ser Val Ala
            100                 105                 110 ttg ata agt ctg ttt gaa aca ata tta ctt ggt tat ctt agt tat aag     384
Leu Ile Ser Leu Phe Glu Thr Ile Leu Leu Gly Tyr Leu Ser Tyr Lys
        115                 120                 125 gga aac atc tgg gaa cag att tta cga ata ccc ttc atc ttg gaa ata     432
Gly Asn Ile Trp Glu Gln Ile Leu Arg Ile Pro Phe Ile Leu Glu Ile
    130                 135                 140 att aat gca gtt ccc ttc att atc tca ata ttc tgg cct tcc tta agg     480
Ile Asn Ala Val Pro Phe Ile Ile Ser Ile Phe Trp Pro Ser Leu Arg
145                 150                 155                 160 aat cta ttt gtc cca gtc ttt ctg aac tgt tgg ctt gcc aaa cat gcc     528
Asn Leu Phe Val Pro Val Phe Leu Asn Cys Trp Leu Ala Lys His Ala
                165                 170                 175 ttg gaa aat atg att aat gat cta cac aga gcc att cag cgt aca cag     576
Leu Glu Asn Met Ile Asn Asp Leu His Arg Ala Ile Gln Arg Thr Gln
            180                 185                 190
```

```
                                                                  -continued
tct gca atg ttt aat caa gtt ttg att tta ata tct aca tta cta tgc    624
Ser Ala Met Phe Asn Gln Val Leu Ile Leu Ile Ser Thr Leu Leu Cys
        195                 200                 205 ctt atc ttc acc tgc att tgt ggg atc caa cat ctg gaa cga ata gga    672
Leu Ile Phe Thr Cys Ile Cys Gly Ile Gln His Leu Glu Arg Ile Gly
210                 215                 220 aag aag ctg aat ctc ttt gac tcc ctt tat ttc tgc att gtg acg ttt    720
Lys Lys Leu Asn Leu Phe Asp Ser Leu Tyr Phe Cys Ile Val Thr Phe
225                 230                 235                 240 tct act gtg ggc ttc ggg gat gtc act cct gaa aca tgg tcc tcc aag    768
Ser Thr Val Gly Phe Gly Asp Val Thr Pro Glu Thr Trp Ser Ser Lys
                245                 250                 255 ctt ttt gta gtt gct atg att tgt gtt gct ctt gtg gtt cta ccc ata    816
Leu Phe Val Val Ala Met Ile Cys Val Ala Leu Val Val Leu Pro Ile
            260                 265                 270 cag ttt gaa cag ctg gct tat ttg tgg atg gag aga caa aag tca gga    864
Gln Phe Glu Gln Leu Ala Tyr Leu Trp Met Glu Arg Gln Lys Ser Gly
        275                 280                 285 gga aac tat agt cga cat aga gct caa act gaa aag cat gtc gtc ctg    912
Gly Asn Tyr Ser Arg His Arg Ala Gln Thr Glu Lys His Val Val Leu
    290                 295                 300 tgt gtc agc tca ctg aag att gat tta ctt atg gat ttt tta aat gaa    960
Cys Val Ser Ser Leu Lys Ile Asp Leu Leu Met Asp Phe Leu Asn Glu
305                 310                 315                 320 ttc tat gct cat cct agg ctc cag gat tat tat gtg gtg att tgt tgt   1008
Phe Tyr Ala His Pro Arg Leu Gln Asp Tyr Tyr Val Val Ile Cys
                325                 330                 335 cct act gaa atg gat gta cag gtt cga agg gta ctg cag att cca atg   1056
Pro Thr Glu Met Asp Val Gln Val Arg Arg Val Leu Gln Ile Pro Met
            340                 345                 350 tgg tcc caa cga gtt atc tac ctt caa ggt tca gcc ctt aaa gat caa   1104
Trp Ser Gln Arg Val Ile Tyr Leu Gln Gly Ser Ala Leu Lys Asp Gln
        355                 360                 365 gac cta ttg aga gca aag atg gat gac gct gag gcc tgt ttt att ctc   1152
Asp Leu Leu Arg Ala Lys Met Asp Asp Ala Glu Ala Cys Phe Ile Leu
    370                 375                 380 agt agc cgt tgt gaa gtg gat agg aca tca tct gat cac caa aca att   1200
Ser Ser Arg Cys Glu Val Asp Arg Thr Ser Ser Asp His Gln Thr Ile
385                 390                 395                 400 ttg aga gca tgg gct gtg aaa gat ttt gct cca aat tgt cct ttg tat   1248
Leu Arg Ala Trp Ala Val Lys Asp Phe Ala Pro Asn Cys Pro Leu Tyr
                405                 410                 415 gtc cag ata tta aag cct gaa aat aaa ttt cac atc aaa ttt gct gat   1296
Val Gln Ile Leu Lys Pro Glu Asn Lys Phe His Ile Lys Phe Ala Asp
            420                 425                 430 cat gtt gtt tgt gaa gaa gag ttt aaa tac gcc atg tta gct tta aac   1344
His Val Val Cys Glu Glu Glu Phe Lys Tyr Ala Met Leu Ala Leu Asn
        435                 440                 445 tgt ata tgc cca gca aca tct aca ctt att aca cta ctg gtt cat acc   1392
Cys Ile Cys Pro Ala Thr Ser Thr Leu Ile Thr Leu Leu Val His Thr
    450                 455                 460 tct aga ggg caa gaa ggc cag caa tcg cca gaa caa tgg cag aag atg   1440
Ser Arg Gly Gln Glu Gly Gln Gln Ser Pro Glu Gln Trp Gln Lys Met
465                 470                 475                 480 tac ggt aga tgc tcc ggg aat gaa gtc tac cac att gtt ttg gaa gaa   1488
Tyr Gly Arg Cys Ser Gly Asn Glu Val Tyr His Ile Val Leu Glu Glu
                485                 490                 495 agt aca ttt ttt gct gaa tat gaa gga aag agt ttt aca tat gcc tct   1536
Ser Thr Phe Phe Ala Glu Tyr Glu Gly Lys Ser Phe Thr Tyr Ala Ser
            500                 505                 510
```

```
ttc cat gca cac aaa aag ttt ggc gtc tgc ttg att ggt gtt agg agg      1584
Phe His Ala His Lys Lys Phe Gly Val Cys Leu Ile Gly Val Arg Arg
        515                 520                 525 gag gat aat aaa aac att ttg ctg aat cca ggt cct cga tac att atg      1632
Glu Asp Asn Lys Asn Ile Leu Leu Asn Pro Gly Pro Arg Tyr Ile Met
530                 535                 540 aat tct aca gac ata tgc ttt tat att aat att acc aaa gaa gag aat      1680
Asn Ser Thr Asp Ile Cys Phe Tyr Ile Asn Ile Thr Lys Glu Glu Asn
545                 550                 555                 560 tca gca ttt aaa aac caa gac cag cag aga aaa agc aat gtg tcc agg      1728
Ser Ala Phe Lys Asn Gln Asp Gln Gln Arg Lys Ser Asn Val Ser Arg
        565                 570                 575 tcg ttt tat cat gga cct tcc aga tta cct gta cat agc ata att gcc      1776
Ser Phe Tyr His Gly Pro Ser Arg Leu Pro Val His Ser Ile Ile Ala
        580                 585                 590 agc atg ggt act gtg gct ata gac ttg caa gat aca agc tgt aga tca      1824
Ser Met Gly Thr Val Ala Ile Asp Leu Gln Asp Thr Ser Cys Arg Ser
        595                 600                 605 gca agt ggc cct acc ctg tct ctt cct aca gag gga agc aaa gaa ata      1872
Ala Ser Gly Pro Thr Leu Ser Leu Pro Thr Glu Gly Ser Lys Glu Ile
610                 615                 620 aga aga cct agc att gct cct gtt tta gag gtt gca gat aca tca tcg      1920
Arg Arg Pro Ser Ile Ala Pro Val Leu Glu Val Ala Asp Thr Ser Ser
625                 630                 635                 640 att caa aca tgt gat ctt cta agt gac caa tca gaa gat gaa act aca      1968
Ile Gln Thr Cys Asp Leu Leu Ser Asp Gln Ser Glu Asp Glu Thr Thr
                645                 650                 655 cca gat gaa gaa atg tct tca aac tta gag tat gct aaa ggt tac cca      2016
Pro Asp Glu Glu Met Ser Ser Asn Leu Glu Tyr Ala Lys Gly Tyr Pro
            660                 665                 670 cct tat tct cca tat ata gga agt tca ccc act ttt tgt cat ctc ctt      2064
Pro Tyr Ser Pro Tyr Ile Gly Ser Ser Pro Thr Phe Cys His Leu Leu
        675                 680                 685 cat gaa aaa gta cca ttt tgc tgc tta aga tta gac aag agt tgc caa      2112
His Glu Lys Val Pro Phe Cys Cys Leu Arg Leu Asp Lys Ser Cys Gln
690                 695                 700 cat aac tac tat gag gat gca aaa gcc tat gga ttc aaa aat aaa cta      2160
His Asn Tyr Tyr Glu Asp Ala Lys Ala Tyr Gly Phe Lys Asn Lys Leu
705                 710                 715                 720 att ata gtt gca gct gaa aca gct gga aat gga tta tat aac ttt att      2208
Ile Ile Val Ala Ala Glu Thr Ala Gly Asn Gly Leu Tyr Asn Phe Ile
                725                 730                 735 gtt cct ctc agg gca tat tat aga cca aag aaa gaa ctt aat ccc ata      2256
Val Pro Leu Arg Ala Tyr Tyr Arg Pro Lys Lys Glu Leu Asn Pro Ile
            740                 745                 750 gta ctg cta ttg gat aac ccg cca gat atg cat ttt ctg gat gca atc      2304
Val Leu Leu Leu Asp Asn Pro Pro Asp Met His Phe Leu Asp Ala Ile
        755                 760                 765 tgt tgg ttt cca atg gtt tac tac atg gtg ggc tct att gac aac cta      2352
Cys Trp Phe Pro Met Val Tyr Tyr Met Val Gly Ser Ile Asp Asn Leu
        770                 775                 780 gat gac tta ctc agg tgt gga gtg act ttt gct gct aat atg gtg gtt      2400
Asp Asp Leu Leu Arg Cys Gly Val Thr Phe Ala Ala Asn Met Val Val
785                 790                 795                 800 gtg gat aaa gag agc acc atg agt gcc gag gaa gac tac atg gca gat      2448
Val Asp Lys Glu Ser Thr Met Ser Ala Glu Glu Asp Tyr Met Ala Asp
                805                 810                 815 gcc aaa acc att gtg aac gtg cag aca ctc ttc agg ttg ttt tcc agt      2496
Ala Lys Thr Ile Val Asn Val Gln Thr Leu Phe Arg Leu Phe Ser Ser
```

-continued

```
                820                 825                 830
ctc agt att atc aca gag cta act cac ccc gcc aac atg aga ttc atg      2544
Leu Ser Ile Ile Thr Glu Leu Thr His Pro Ala Asn Met Arg Phe Met
            835                 840                 845 caa ttc aga gcc aaa gac tgt tac tct ctt gct ctt tca aaa ctg gaa      2592
Gln Phe Arg Ala Lys Asp Cys Tyr Ser Leu Ala Leu Ser Lys Leu Glu
850                 855                 860 aag aaa gaa cgg gag aga ggc tct aac ttg gcc ttt atg ttt cga ctg      2640
Lys Lys Glu Arg Glu Arg Gly Ser Asn Leu Ala Phe Met Phe Arg Leu
865                 870                 875                 880 cct ttt gct gct ggg agg gtg ttt agc atc agt atg ttg gac act ctg      2688
Pro Phe Ala Ala Gly Arg Val Phe Ser Ile Ser Met Leu Asp Thr Leu
                885                 890                 895 ctg tat cag tca ttt gtg aag gat tat atg att tct atc acg aga ctt      2736
Leu Tyr Gln Ser Phe Val Lys Asp Tyr Met Ile Ser Ile Thr Arg Leu
            900                 905                 910 ctg ttg gga ctg gac act aca cca gga tct ggg ttt ctt tgt tct atg      2784
Leu Leu Gly Leu Asp Thr Thr Pro Gly Ser Gly Phe Leu Cys Ser Met
        915                 920                 925 aaa atc act gca gat gac tta tgg atc aga act tat gcc aga ctt tat      2832
Lys Ile Thr Ala Asp Asp Leu Trp Ile Arg Thr Tyr Ala Arg Leu Tyr
930                 935                 940 cag aag ttg tgt tct tct act gga gat gtt ccc att gga atc tac agg      2880
Gln Lys Leu Cys Ser Ser Thr Gly Asp Val Pro Ile Gly Ile Tyr Arg
945                 950                 955                 960 act gag tct cag aaa ctt act aca tct gag tct caa ata tct atc agt      2928
Thr Glu Ser Gln Lys Leu Thr Thr Ser Glu Ser Gln Ile Ser Ile Ser
                965                 970                 975 gta gaa gag tgg gaa gac acc aaa gac tcc aaa gaa caa ggg cac cac      2976
Val Glu Glu Trp Glu Asp Thr Lys Asp Ser Lys Glu Gln Gly His His
            980                 985                 990 cgc agc aac cac cgc aac tca aca tcc agt gac cag tcg gac cat ccc      3024
Arg Ser Asn His Arg Asn Ser Thr Ser Ser Asp Gln Ser Asp His Pro
        995                 1000                1005 ttg ctg cgg aga aaa agc atg cag tgg gcc cga aga ctg agc aga aaa      3072
Leu Leu Arg Arg Lys Ser Met Gln Trp Ala Arg Arg Leu Ser Arg Lys
    1010                1015                1020 ggc cca aaa cac tct ggt aaa aca gct gaa aaa ata acc cag cag cga      3120
Gly Pro Lys His Ser Gly Lys Thr Ala Glu Lys Ile Thr Gln Gln Arg
1025                1030                1035                1040 ctg aac ctc tac agg agg tca gaa aga caa gag ctt gct gaa ctt gtg      3168
Leu Asn Leu Tyr Arg Arg Ser Glu Arg Gln Glu Leu Ala Glu Leu Val
                1045                1050                1055 aaa aat aga atg aaa cac ttg ggt ctt tct aca gtg gga tat gat gaa      3216
Lys Asn Arg Met Lys His Leu Gly Leu Ser Thr Val Gly Tyr Asp Glu
            1060                1065                1070 atg aat gat cat caa agt acc ctc tcc tac atc ctg att aac cca tct      3264
Met Asn Asp His Gln Ser Thr Leu Ser Tyr Ile Leu Ile Asn Pro Ser
        1075                1080                1085 cca gat acc aga ata gag ctg aat gat gtt gta tac tta att cga cca      3312
Pro Asp Thr Arg Ile Glu Leu Asn Asp Val Val Tyr Leu Ile Arg Pro
    1090                1095                1100 gat cca ctg gcc tac ctt cca aac agt gag ccc agt cga aga aac agc      3360
Asp Pro Leu Ala Tyr Leu Pro Asn Ser Glu Pro Ser Arg Arg Asn Ser
1105                1110                1115                1120 atc tgc aat gtc act ggt caa gat tct cgg gag gaa act caa ctt tga      3408
Ile Cys Asn Val Thr Gly Gln Asp Ser Arg Glu Glu Thr Gln Leu
                1125                1130                1135
```

<210> SEQ ID NO 4
<211> LENGTH: 1135
<212> TYPE: PRT
<213> ORGANISM: Homo sapiens
<220> FEATURE:
<223> OTHER INFORMATION: human Slo4 potassium channel alpha subunit

<400> SEQUENCE: 4

```
Met Val Asp Leu Glu Ser Glu Val Pro Pro Leu Pro Pro Arg Tyr Arg
 1               5                  10                  15

Phe Arg Asp Leu Leu Leu Gly Asp Gln Gly Trp Gln Asn Asp Asp Arg
             20                  25                  30

Val Gln Val Glu Phe Tyr Met Asn Glu Asn Thr Phe Lys Glu Arg Leu
         35                  40                  45

Lys Leu Phe Phe Ile Lys Asn Gln Arg Ser Ser Leu Arg Ile Arg Leu
     50                  55                  60

Phe Asn Phe Ser Leu Lys Leu Leu Ser Cys Leu Leu Tyr Ile Ile Arg
 65                  70                  75                  80

Val Leu Leu Glu Asn Pro Ser Gln Gly Asn Glu Trp Ser His Ile Phe
                 85                  90                  95

Trp Val Asn Arg Ser Leu Pro Leu Trp Gly Leu Gln Val Ser Val Ala
            100                 105                 110

Leu Ile Ser Leu Phe Glu Thr Ile Leu Leu Gly Tyr Leu Ser Tyr Lys
        115                 120                 125

Gly Asn Ile Trp Glu Gln Ile Leu Arg Ile Pro Phe Ile Leu Glu Ile
    130                 135                 140

Ile Asn Ala Val Pro Phe Ile Ile Ser Ile Phe Trp Pro Ser Leu Arg
145                 150                 155                 160

Asn Leu Phe Val Pro Val Phe Leu Asn Cys Trp Leu Ala Lys His Ala
                165                 170                 175

Leu Glu Asn Met Ile Asn Asp Leu His Arg Ala Ile Gln Arg Thr Gln
            180                 185                 190

Ser Ala Met Phe Asn Gln Val Leu Ile Leu Ser Thr Leu Leu Cys
        195                 200                 205

Leu Ile Phe Thr Cys Ile Cys Gly Ile Gln His Leu Glu Arg Ile Gly
    210                 215                 220

Lys Lys Leu Asn Leu Phe Asp Ser Leu Tyr Phe Cys Ile Val Thr Phe
225                 230                 235                 240

Ser Thr Val Gly Phe Gly Asp Val Thr Pro Glu Thr Trp Ser Ser Lys
                245                 250                 255

Leu Phe Val Val Ala Met Ile Cys Val Ala Leu Val Val Leu Pro Ile
            260                 265                 270

Gln Phe Glu Gln Leu Ala Tyr Leu Trp Met Glu Arg Gln Lys Ser Gly
        275                 280                 285

Gly Asn Tyr Ser Arg His Arg Ala Gln Thr Glu Lys His Val Val Leu
    290                 295                 300

Cys Val Ser Ser Leu Lys Ile Asp Leu Leu Met Asp Phe Leu Asn Glu
305                 310                 315                 320

Phe Tyr Ala His Pro Arg Leu Gln Asp Tyr Tyr Val Val Ile Leu Cys
                325                 330                 335

Pro Thr Glu Met Asp Val Gln Val Arg Arg Val Leu Gln Ile Pro Met
            340                 345                 350

Trp Ser Gln Arg Val Ile Tyr Leu Gln Gly Ser Ala Leu Lys Asp Gln
        355                 360                 365

Asp Leu Leu Arg Ala Lys Met Asp Asp Ala Glu Ala Cys Phe Ile Leu
```

-continued

```
            370                 375                 380
Ser Ser Arg Cys Glu Val Asp Arg Thr Ser Ser Asp His Gln Thr Ile
385                 390                 395                 400

Leu Arg Ala Trp Ala Val Lys Asp Phe Ala Pro Asn Cys Pro Leu Tyr
                405                 410                 415

Val Gln Ile Leu Lys Pro Glu Asn Lys Phe His Ile Lys Phe Ala Asp
            420                 425                 430

His Val Val Cys Glu Glu Glu Phe Lys Tyr Ala Met Leu Ala Leu Asn
                435                 440                 445

Cys Ile Cys Pro Ala Thr Ser Thr Leu Ile Thr Leu Leu Val His Thr
450                 455                 460

Ser Arg Gly Gln Glu Gly Gln Gln Ser Pro Glu Gln Trp Gln Lys Met
465                 470                 475                 480

Tyr Gly Arg Cys Ser Gly Asn Glu Val Tyr His Ile Val Leu Glu Glu
                485                 490                 495

Ser Thr Phe Phe Ala Glu Tyr Glu Gly Lys Ser Phe Thr Tyr Ala Ser
                500                 505                 510

Phe His Ala His Lys Lys Phe Gly Val Cys Leu Ile Gly Val Arg Arg
                515                 520                 525

Glu Asp Asn Lys Asn Ile Leu Leu Asn Pro Gly Pro Arg Tyr Ile Met
530                 535                 540

Asn Ser Thr Asp Ile Cys Phe Tyr Ile Asn Ile Thr Lys Glu Glu Asn
545                 550                 555                 560

Ser Ala Phe Lys Asn Gln Asp Gln Gln Arg Lys Ser Asn Val Ser Arg
                565                 570                 575

Ser Phe Tyr His Gly Pro Ser Arg Leu Pro Val His Ser Ile Ile Ala
                580                 585                 590

Ser Met Gly Thr Val Ala Ile Asp Leu Gln Asp Thr Ser Cys Arg Ser
                595                 600                 605

Ala Ser Gly Pro Thr Leu Ser Leu Pro Thr Glu Gly Ser Lys Glu Ile
                610                 615                 620

Arg Arg Pro Ser Ile Ala Pro Val Leu Glu Val Ala Asp Thr Ser Ser
625                 630                 635                 640

Ile Gln Thr Cys Asp Leu Leu Ser Asp Gln Ser Glu Asp Glu Thr Thr
                645                 650                 655

Pro Asp Glu Glu Met Ser Ser Asn Leu Glu Tyr Ala Lys Gly Tyr Pro
                660                 665                 670

Pro Tyr Ser Pro Tyr Ile Gly Ser Ser Pro Thr Phe Cys His Leu Leu
                675                 680                 685

His Glu Lys Val Pro Phe Cys Cys Leu Arg Leu Asp Lys Ser Cys Gln
                690                 695                 700

His Asn Tyr Tyr Glu Asp Ala Lys Ala Tyr Gly Phe Lys Asn Lys Leu
705                 710                 715                 720

Ile Ile Val Ala Ala Glu Thr Ala Gly Asn Gly Leu Tyr Asn Phe Ile
                725                 730                 735

Val Pro Leu Arg Ala Tyr Tyr Arg Pro Lys Lys Glu Leu Asn Pro Ile
                740                 745                 750

Val Leu Leu Leu Asp Asn Pro Pro Asp Met His Phe Leu Asp Ala Ile
                755                 760                 765

Cys Trp Phe Pro Met Val Tyr Tyr Met Val Gly Ser Ile Asp Asn Leu
                770                 775                 780

Asp Asp Leu Leu Arg Cys Gly Val Thr Phe Ala Ala Asn Met Val Val
785                 790                 795                 800
```

```
Val Asp Lys Glu Ser Thr Met Ser Ala Glu Asp Tyr Met Ala Asp
            805                 810                 815

Ala Lys Thr Ile Val Asn Val Gln Thr Leu Phe Arg Leu Phe Ser Ser
            820                 825                 830

Leu Ser Ile Ile Thr Glu Leu Thr His Pro Ala Asn Met Arg Phe Met
            835                 840                 845

Gln Phe Arg Ala Lys Asp Cys Tyr Ser Leu Ala Leu Ser Lys Leu Glu
            850                 855                 860

Lys Lys Glu Arg Glu Arg Gly Ser Asn Leu Ala Phe Met Phe Arg Leu
865                 870                 875                 880

Pro Phe Ala Ala Gly Arg Val Phe Ser Ile Ser Met Leu Asp Thr Leu
            885                 890                 895

Leu Tyr Gln Ser Phe Val Lys Asp Tyr Met Ile Ser Ile Thr Arg Leu
            900                 905                 910

Leu Leu Gly Leu Asp Thr Thr Pro Gly Ser Gly Phe Leu Cys Ser Met
            915                 920                 925

Lys Ile Thr Ala Asp Asp Leu Trp Ile Arg Thr Tyr Ala Arg Leu Tyr
            930                 935                 940

Gln Lys Leu Cys Ser Ser Thr Gly Asp Val Pro Ile Gly Ile Tyr Arg
945                 950                 955                 960

Thr Glu Ser Gln Lys Leu Thr Ser Glu Ser Gln Ile Ser Ile Ser
            965                 970                 975

Val Glu Glu Trp Glu Asp Thr Lys Asp Ser Lys Glu Gln Gly His His
            980                 985                 990

Arg Ser Asn His Arg Asn Ser Thr Ser Ser Asp Gln Ser Asp His Pro
            995                 1000                1005

Leu Leu Arg Arg Lys Ser Met Gln Trp Ala Arg Arg Leu Ser Arg Lys
            1010                1015                1020

Gly Pro Lys His Ser Gly Lys Thr Ala Glu Lys Ile Thr Gln Gln Arg
1025                1030                1035                1040

Leu Asn Leu Tyr Arg Arg Ser Glu Arg Gln Glu Leu Ala Glu Leu Val
            1045                1050                1055

Lys Asn Arg Met Lys His Leu Gly Leu Ser Thr Val Gly Tyr Asp Glu
            1060                1065                1070

Met Asn Asp His Gln Ser Thr Leu Ser Tyr Ile Leu Ile Asn Pro Ser
            1075                1080                1085

Pro Asp Thr Arg Ile Glu Leu Asn Asp Val Val Tyr Leu Ile Arg Pro
            1090                1095                1100

Asp Pro Leu Ala Tyr Leu Pro Asn Ser Glu Pro Ser Arg Arg Asn Ser
1105                1110                1115                1120

Ile Cys Asn Val Thr Gly Gln Asp Ser Arg Glu Glu Thr Gln Leu
            1125                1130                1135

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:Slo2
      gene-specific nested RACE PCR amplification sense
      primer oligo 1

<400> SEQUENCE: 5
caccacggag ctcacccacc cttcc                                          25
```

```
<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence:Slo2
      gene-specific nested 3' RACE PCR amplification
      sense primer oligo 2

<400> SEQUENCE: 6
cgcgtcttca gcatcagcat gttggac                                        27

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence:Slo2
      gene-specific nested 5' RACE PCR amplification
      antisense primer oligo 3

<400> SEQUENCE: 7
ctggtagagc agtgtgtcca acatgctg                                       28

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence:Slo2-
      specific nested 5' RACE PCR amplification antisense primer
      oligo 4

<400> SEQUENCE: 8
actgcatgaa gcgcatgttg gaagggtg                                       28

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:Slo2
      gene-specific nested 5' RACE PCR amplification
      antisense primer oligo 5

<400> SEQUENCE: 9
cccattgccg gccgtctctg ccgag                                          25

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence:Slo2
      gene-specific nested 5' RACE PCR amplification
      antisense primer oligo 6

<400> SEQUENCE: 10
cttgaacccg taggccttgg cgtcttc                                        27

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence:new
      Slo2-specific 5' PCR amplification antisense
      primer oligo 7
```

```
<400> SEQUENCE: 11
cacaccacgt ggtcagcaaa cttgacg                                        27

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence:new
      Slo2-specific 5' PCR amplification antisense
      primer oligo 8

<400> SEQUENCE: 12
gcagttgggg gcgaagtcct tcacgg                                         26

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence:Slo2
      overlap extension PCR amplification sense primer oligo 9

<400> SEQUENCE: 13
caccttcaag gagcggctca agctg                                          25

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence:Slo2
      overlap extension PCR amplification antisense primer oligo
      10

<400> SEQUENCE: 14
gacgtgtgca ccagcagggt gatgag                                         26

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence:Slo2
      overlap extension PCR amplification sense primer oligo 11

<400> SEQUENCE: 15
gtttcacgtc aagtttgctg accacg                                         26

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence:Slo2
      overlap extension PCR amplification antisense primer oligo
      12

<400> SEQUENCE: 16
ccgtacgtgc ggatccacag gtcg                                           24

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence:Slo2
```

-continued amplification sense primer oligo 13

<400> SEQUENCE: 17
cgtgaaggac tacatgatca ccatc					25

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence:Slo2
      overlap extension PCR amplification antisense primer oligo
      14

<400> SEQUENCE: 18
ttagagctgt gtctcgtcgc gagtctc					27

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence:Slo2
      amplification sense primer oligo 15

<400> SEQUENCE: 19
atggcgcggg ccaagct					17

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence:Slo2
      amplification antisense primer oligo 16

<400> SEQUENCE: 20
gagacaggga ggagtccagg ctgaa					25

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence:Slo2
      amplification primer oligo 17

<400> SEQUENCE: 21
cgtgggccag aggcttcctg tagaa					25

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence:Slo2
      amplification primer oligo 18

<400> SEQUENCE: 22
gctcccagat gttgcctttg tagctg					26

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence:Slo4 amplification sense primer oligo 19

<400> SEQUENCE: 23
ggcgtctgct tgattggtgt tagga                                          25

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence:Slo4
      amplification antisense primer oligo 20
      overlapping the stop codon in the EST sequence

<400> SEQUENCE: 24
atcaaagttg agtttcctcc cgag                                           24

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence:Slo4-
      specific 5' RACE PCR amplification antisense primer oligo
      21

<400> SEQUENCE: 25
cccggagcat ctaccgtaca tcttc                                          25

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence:Slo4-
      specific nested 5' RACE PCR amplification antisense primer
      oligo 22

<400> SEQUENCE: 26
ccagctgttc aaactgtatg ggtag                                          25

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence:
      Description of Artificial SequenceSlo4-specific 5' RACE PCR
      amplification antisense primer oligo 23

<400> SEQUENCE: 27
gcttggagga ccatgtttca ggagt                                          25

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence:Slo4
      amplification sense primer oligo 24 overlapping
      the initiator Met codon

<400> SEQUENCE: 28
atggttgatt tggagagcga agtg                                           24

<210> SEQ ID NO 29
<211> LENGTH: 27

```
<212> TYPE: DNA
<213> ORGANISM: Artificial Sequence
<220> FEATURE:
<223> OTHER INFORMATION: Description of Artificial Sequence:Slo4-
      specific amplification sense primer oligo 25

<400> SEQUENCE: 29
caattttgag agcatgggct gtgaaag                                            27

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence:Slo4-
      specific amplification sense primer oligo 26

<400> SEQUENCE: 30
gacttatgga tcagaactta tgcccag                                            27

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence:Slo4-
      specific amplification antisense primer oligo 27

<400> SEQUENCE: 31
catctggtgt agtttcatct tctgattgg                                          29

<210> SEQ ID NO 32
<211> LENGTH: 1237
<212> TYPE: PRT
<213> ORGANISM: Rattus norvegicus
<220> FEATURE:
<223> OTHER INFORMATION: rat potassium channel subunit SLACK

<400> SEQUENCE: 32
```

Met Ala Arg Ala Lys Leu Pro Arg Ser Pro Ser Glu Gly Lys Ala Gly
 1               5                  10                  15

Pro Gly Asp Thr Pro Ala Gly Ser Ala Ala Pro Glu Glu Pro His Gly
                20                  25                  30

Leu Ser Pro Leu Leu Pro Thr Arg Gly Gly Gly Ser Val Gly Ser Asp
            35                  40                  45

Val Gly Gln Arg Leu His Val Glu Asp Phe Ser Leu Asp Ser Ser Leu
        50                  55                  60

Ser Gln Val Gln Val Glu Phe Tyr Val Asn Glu Asn Thr Phe Lys Glu
 65                  70                  75                  80

Arg Leu Lys Leu Phe Phe Ile Lys Asn Gln Arg Ser Ser Leu Arg Ile
                 85                  90                  95

Arg Leu Phe Asn Phe Ser Leu Lys Leu Leu Thr Cys Leu Leu Tyr Ile
            100                 105                 110

Val Arg Val Leu Leu Asp Asn Pro Asp Gln Gly Ile Gly Cys Trp Gly
        115                 120                 125

Cys Thr Lys Tyr Asn Tyr Thr Phe Asn Gly Ser Ser Ser Glu Phe His
    130                 135                 140

Trp Ala Pro Ile Leu Trp Val Glu Arg Lys Met Ala Leu Trp Val Ile
145                 150                 155                 160

Gln Val Ile Val Ala Thr Ile Ser Phe Leu Glu Thr Met Leu Leu Ile
                165                 170                 175

-continued

Tyr Leu Ser Tyr Lys Gly Asn Ile Trp Glu Gln Ile Phe His Val Ser
            180                 185                 190

Phe Val Leu Glu Met Ile Asn Thr Leu Pro Phe Ile Ile Thr Val Phe
            195                 200                 205

Trp Pro Pro Leu Arg Asn Leu Phe Ile Pro Val Phe Leu Asn Cys Trp
210                 215                 220

Leu Ala Lys His Ala Leu Glu Asn Met Ile Asn Asp Phe His Arg Ala
225                 230                 235                 240

Ile Leu Arg Thr Gln Ser Ala Met Phe Asn Gln Val Leu Ile Leu Phe
                245                 250                 255

Cys Thr Leu Leu Cys Leu Val Phe Thr Gly Thr Cys Gly Ile Gln His
            260                 265                 270

Leu Glu Arg Ala Gly Gly Asn Leu Asn Leu Leu Thr Ser Phe Tyr Phe
            275                 280                 285

Cys Ile Val Thr Phe Ser Thr Val Gly Phe Gly Asp Val Thr Pro Lys
            290                 295                 300

Ile Trp Pro Ser Gln Leu Leu Val Val Ile Leu Ile Cys Val Thr Leu
305                 310                 315                 320

Val Val Leu Pro Leu Gln Phe Glu Glu Leu Val Tyr Leu Trp Met Glu
                325                 330                 335

Arg Gln Lys Ser Gly Gly Asn Tyr Ser Arg His Arg Ala Arg Thr Glu
            340                 345                 350

Lys His Val Val Leu Cys Val Ser Ser Leu Lys Ile Asp Leu Leu Met
            355                 360                 365

Asp Phe Leu Asn Glu Phe Tyr Ala His Pro Arg Leu Gln Asp Tyr Tyr
            370                 375                 380

Val Val Ile Leu Cys Pro Ser Glu Met Asp Val Gln Val Arg Arg Val
385                 390                 395                 400

Leu Gln Ile Pro Leu Trp Ser Gln Arg Val Ile Tyr Leu Gln Gly Ser
                405                 410                 415

Ala Leu Lys Asp Gln Asp Leu Met Arg Ala Lys Met Asp Asn Gly Glu
            420                 425                 430

Ala Cys Phe Ile Leu Ser Ser Arg Asn Glu Val Asp Arg Thr Ala Ala
            435                 440                 445

Asp His Gln Thr Ile Leu Arg Ala Trp Ala Val Lys Asp Phe Ala Pro
            450                 455                 460

Asn Cys Pro Leu Tyr Val Gln Ile Leu Lys Pro Glu Asn Lys Phe His
465                 470                 475                 480

Val Lys Phe Ala Asp His Val Val Cys Glu Glu Cys Lys Tyr Ala
                485                 490                 495

Met Leu Ala Leu Asn Cys Ile Cys Pro Ala Thr Ser Thr Leu Ile Thr
            500                 505                 510

Leu Leu Val His Thr Ser Arg Gly Gln Glu Gly Gln Glu Ser Pro Glu
            515                 520                 525

Gln Trp Gln Arg Met Tyr Gly Arg Cys Ser Gly Asn Glu Val Tyr His
            530                 535                 540

Ile Arg Met Gly Asp Ser Lys Phe Phe Arg Glu Tyr Glu Gly Lys Ser
545                 550                 555                 560

Phe Thr Tyr Ala Ala Phe His Ala His Lys Lys Tyr Gly Val Cys Leu
                565                 570                 575

Ile Gly Leu Lys Arg Glu Glu Asn Lys Ser Ile Leu Leu Asn Pro Gly
            580                 585                 590

Pro Arg His Ile Leu Ala Ala Ser Asp Thr Cys Phe Tyr Ile Asn Ile

```
                595                 600                 605
    Thr Lys Glu Glu Asn Ser Ala Phe Ile Phe Lys Gln Glu Glu Lys Gln
    610                 615                 620

Asn Arg Arg Gly Leu Ala Gly Gln Ala Leu Tyr Glu Gly Pro Ser Arg
    625                 630                 635                 640

Leu Pro Val His Ser Ile Ile Ala Ser Met Val Ala Met Asp Leu Gln
                        645                 650                 655

Asn Thr Asp Cys Arg Pro Ser Gln Gly Gly Ser Gly Gly Gly Gly Gly
                    660                 665                 670

Lys Leu Thr Leu Pro Thr Glu Asn Gly Ser Gly Ser Arg Arg Pro Ser
                675                 680                 685

Ile Ala Pro Val Leu Glu Leu Ala Asp Ser Ser Ala Leu Leu Pro Cys
    690                 695                 700

Asp Leu Leu Ser Asp Gln Ser Glu Asp Glu Val Thr Pro Ser Asp Asp
    705                 710                 715                 720

Glu Gly Leu Ser Val Val Glu Tyr Val Lys Gly Tyr Pro Pro Asn Ser
                        725                 730                 735

Pro Tyr Ile Gly Ser Ser Pro Thr Leu Cys His Leu Leu Pro Val Lys
                    740                 745                 750

Ala Pro Phe Cys Cys Leu Arg Leu Asp Lys Gly Cys Lys His Asn Ser
                755                 760                 765

Tyr Glu Asp Ala Lys Ala Tyr Gly Phe Lys Asn Lys Leu Ile Ile Val
    770                 775                 780

Ser Ala Glu Thr Ala Gly Asn Gly Leu Tyr Asn Phe Ile Val Pro Leu
    785                 790                 795                 800

Arg Ala Tyr Tyr Arg Ser Arg Arg Glu Leu Asn Pro Ile Val Leu Leu
                        805                 810                 815

Leu Asp Asn Lys Pro Asp His His Phe Leu Glu Ala Ile Cys Cys Phe
                    820                 825                 830

Pro Met Val Tyr Tyr Met Gly Gly Ser Val Asp Asn Leu Asp Ser Leu
                835                 840                 845

Leu Gln Cys Gly Ile Ile Tyr Ala Asp Asn Leu Val Val Val Asp Lys
    850                 855                 860

Glu Ser Thr Met Ser Ala Glu Glu Asp Tyr Met Ala Asp Ala Lys Thr
    865                 870                 875                 880

Ile Val Asn Val Gln Thr Met Phe Arg Leu Phe Pro Ser Leu Ser Ile
                        885                 890                 895

Thr Thr Glu Leu Thr His Pro Ser Asn Met Arg Phe Met Gln Phe Arg
                    900                 905                 910

Ala Lys Asp Ser Tyr Ser Leu Ala Leu Ser Lys Leu Glu Lys Gln Glu
                915                 920                 925

Arg Glu Asn Gly Ser Asn Leu Ala Phe Met Phe Arg Leu Pro Phe Ala
    930                 935                 940

Ala Gly Arg Val Phe Ser Ile Ser Met Leu Asp Thr Leu Leu Tyr Gln
    945                 950                 955                 960

Ser Phe Val Lys Asp Tyr Met Ile Thr Ile Thr Arg Leu Leu Leu Gly
                        965                 970                 975

Leu Asp Thr Thr Pro Gly Ser Gly Tyr Leu Cys Ala Met Lys Val Thr
                    980                 985                 990

Glu Asp Asp Leu Trp Ile Arg Thr Tyr Gly Arg Leu Phe Gln Lys Leu
                995                 1000                1005

Cys Ser Ser Ser Ala Glu Ile Pro Ile Gly Ile Tyr Arg Thr Glu Cys
            1010                1015                1020
```

His Val Phe Ser Ser Glu Pro His Asp Leu Arg Ala Gln Ser Gln Ile
1025                1030                1035                1040

Ser Val Asn Met Glu Asp Cys Glu Asp Thr Arg Glu Ala Lys Gly Pro
            1045                1050                1055

Trp Gly Thr Arg Ala Ala Ser Gly Gly Gly Ser Thr His Gly Arg His
        1060                1065                1070

Gly Gly Ser Ala Asp Pro Val Glu His Pro Leu Arg Arg Lys Ser
    1075                1080                1085

Leu Gln Trp Ala Arg Lys Leu Ser Arg Lys Ser Ser Lys Gln Ala Gly
    1090                1095                1100

Lys Ala Pro Met Thr Thr Asp Trp Ile Thr Gln Gln Arg Leu Ser Leu
1105                1110                1115                1120

Tyr Arg Arg Ser Glu Arg Gln Glu Leu Ser Glu Leu Val Lys Asn Arg
            1125                1130                1135

Met Lys His Leu Gly Leu Pro Thr Thr Gly Tyr Glu Asp Val Ala Asn
            1140                1145                1150

Leu Thr Ala Ser Asp Val Met Asn Arg Val Asn Leu Gly Tyr Leu Gln
        1155                1160                1165

Asp Glu Met Asn Asp His His Gln Asn Thr Leu Ser Tyr Val Leu Ile
    1170                1175                1180

Asn Pro Pro Pro Asp Thr Arg Leu Glu Pro Asn Asp Ile Val Tyr Leu
1185                1190                1195                1200

Ile Arg Ser Asp Pro Leu Ala His Val Thr Ser Ser Ser Gln Ser Arg
            1205                1210                1215

Lys Ser Ser Cys Ser Asn Lys Leu Ser Ser Cys Asn Pro Glu Thr Arg
            1220                1225                1230

Asp Glu Thr Gln Leu
        1235

<210> SEQ ID NO 33
<211> LENGTH: 1151
<212> TYPE: PRT
<213> ORGANISM: Homo sapiens
<220> FEATURE:
<223> OTHER INFORMATION: partial human cDNA KIAA1422

<400> SEQUENCE: 33

Ala Arg Glu Glu Gly Gly Gly Ser His Ser Leu Leu Pro Arg Val Gly
1               5                   10                  15

Ser Glu Leu Pro Gly Arg Met Pro Leu Pro Asp Gly Ala Arg Thr Pro
            20                  25                  30

Gly Gly Val Cys Arg Glu Ala Arg Gly Gly Gly Tyr Thr Asn Arg Thr
        35                  40                  45

Phe Glu Phe Asp Asp Gly Gln Cys Ala Pro Arg Pro Cys Ala Gly
    50                  55                  60

Asp Gly Ala Leu Leu Asp Thr Ala Gly Phe Lys Met Ser Asp Leu Asp
65                  70                  75                  80

Ser Glu Val Leu Pro Leu Pro Arg Tyr Arg Phe Arg Asp Leu Leu
            85                  90                  95

Leu Gly Asp Pro Ser Phe Gln Asn Asp Asp Arg Val Gln Val Glu Phe
        100                 105                 110

Tyr Val Asn Glu Asn Thr Phe Lys Glu Arg Leu Lys Leu Phe Phe Ile
    115                 120                 125

Lys Asn Gln Arg Ser Ser Leu Arg Ile Arg Leu Phe Asn Phe Ser Leu
    130                 135                 140

-continued

```
Lys Leu Leu Thr Cys Leu Leu Tyr Ile Val Arg Val Leu Leu Asp Asp
145                 150                 155                 160

Pro Ala Leu Gly Ile Gly Cys Trp Gly Cys Pro Lys Gln Asn Tyr Ser
                165                 170                 175

Phe Asn Asp Ser Ser Glu Ile Asn Trp Ala Pro Ile Leu Trp Val
            180                 185                 190

Glu Arg Lys Met Thr Leu Trp Ala Ile Gln Val Ile Val Ala Ile Ile
            195                 200                 205

Ser Phe Leu Glu Thr Met Leu Leu Ile Tyr Leu Ser Tyr Lys Gly Asn
    210                 215                 220

Ile Trp Glu Gln Ile Phe Arg Val Ser Phe Val Leu Glu Met Ile Asn
225                 230                 235                 240

Thr Leu Pro Phe Ile Ile Thr Ile Phe Trp Pro Pro Leu Arg Asn Leu
                245                 250                 255

Phe Ile Pro Val Phe Leu Asn Cys Trp Leu Ala Lys His Ala Leu Glu
            260                 265                 270

Asn Met Ile Asn Asp Phe His Arg Ala Ile Leu Arg Thr Gln Ser Ala
    275                 280                 285

Met Phe Asn Gln Val Leu Ile Leu Phe Cys Thr Leu Leu Cys Leu Val
    290                 295                 300

Phe Thr Gly Thr Cys Gly Ile Gln His Leu Glu Arg Ala Gly Glu Asn
305                 310                 315                 320

Leu Ser Leu Leu Thr Ser Phe Tyr Phe Cys Ile Val Thr Phe Ser Thr
                325                 330                 335

Val Gly Tyr Gly Asp Val Thr Pro Lys Ile Trp Pro Ser Gln Leu Leu
            340                 345                 350

Val Val Ile Met Ile Cys Val Ala Leu Val Val Leu Pro Leu Gln Phe
            355                 360                 365

Glu Glu Leu Val Tyr Leu Trp Met Glu Arg Gln Lys Ser Gly Gly Asn
    370                 375                 380

Tyr Ser Arg His Arg Ala Gln Thr Glu Lys His Val Val Leu Cys Val
385                 390                 395                 400

Ser Ser Leu Lys Ile Asp Leu Leu Met Asp Phe Leu Asn Glu Phe Tyr
                405                 410                 415

Ala His Pro Arg Leu Gln Asp Tyr Tyr Val Val Ile Leu Cys Pro Thr
            420                 425                 430

Glu Met Asp Val Gln Val Arg Arg Val Leu Gln Ile Pro Leu Trp Ser
    435                 440                 445

Gln Arg Val Ile Tyr Leu Gln Gly Ser Ala Leu Lys Asp Gln Asp Leu
    450                 455                 460

Met Arg Ala Lys Met Asp Asn Gly Glu Ala Cys Phe Ile Leu Ser Ser
465                 470                 475                 480

Arg Asn Glu Val Asp Arg Thr Ala Ala Asp His Gln Thr Ile Leu Arg
                485                 490                 495

Ala Trp Ala Val Lys Asp Phe Ala Pro Asn Cys Pro Leu Tyr Val Gln
            500                 505                 510

Ile Leu Lys Pro Glu Asn Lys Phe His Val Lys Phe Ala Asp His Val
    515                 520                 525

Val Cys Glu Glu Glu Cys Lys Tyr Ala Met Leu Ala Leu Asn Cys Ile
    530                 535                 540

Cys Pro Ala Thr Ser Thr Leu Ile Thr Leu Leu Val His Thr Ser Arg
545                 550                 555                 560
```

-continued

```
Gly Gln Glu Gly Gln Glu Ser Pro Glu Gln Trp Gln Arg Met Tyr Gly
                565                 570                 575

Arg Cys Ser Gly Asn Glu Val Tyr His Ile Arg Met Gly Asp Ser Lys
            580                 585                 590

Phe Phe Arg Glu Tyr Gly Lys Ser Phe Thr Tyr Ala Ala Phe His
        595                 600                 605

Ala His Lys Lys Tyr Gly Val Cys Leu Ile Gly Leu Lys Arg Glu Asp
        610                 615                 620

Asn Lys Ser Ile Leu Leu Asn Pro Gly Pro Arg His Ile Leu Ala Ala
625                 630                 635                 640

Ser Asp Thr Cys Phe Tyr Ile Asn Ile Thr Lys Glu Glu Asn Ser Ala
                645                 650                 655

Phe Ile Phe Lys Gln Glu Glu Lys Arg Lys Lys Arg Ala Phe Ser Gly
                660                 665                 670

Gln Gly Leu His Glu Gly Pro Ala Arg Leu Pro Val His Ser Ile Ile
        675                 680                 685

Ala Ser Met Gly Thr Val Ala Met Asp Leu Gln Gly Thr Glu His Arg
        690                 695                 700

Pro Thr Gln Ser Gly Gly Gly Gly Gly Ser Lys Leu Ala Leu Pro
705                 710                 715                 720

Thr Glu Asn Gly Ser Gly Ser Arg Arg Pro Ser Ile Ala Pro Val Leu
            725                 730                 735

Glu Leu Ala Asp Ser Ser Ala Leu Leu Pro Cys Asp Leu Leu Ser Asp
                740                 745                 750

Gln Ser Glu Asp Glu Val Thr Pro Ser Asp Asp Glu Gly Leu Ser Val
            755                 760                 765

Val Glu Tyr Val Lys Gly Tyr Pro Pro Asn Ser Pro Tyr Ile Gly Ser
770                 775                 780

Ser Pro Thr Leu Cys His Leu Leu Pro Val Lys Ala Pro Phe Cys Cys
785                 790                 795                 800

Leu Arg Leu Asp Lys Gly Cys Lys His Asn Ser Tyr Glu Asp Ala Lys
            805                 810                 815

Ala Tyr Gly Phe Lys Asn Lys Leu Ile Ile Val Ser Ala Glu Thr Ala
        820                 825                 830

Gly Asn Gly Leu Tyr Asn Phe Ile Val Pro Leu Arg Ala Tyr Tyr Arg
        835                 840                 845

Ser Arg Lys Glu Leu Asn Pro Ile Val Leu Leu Leu Asp Asn Lys Pro
850                 855                 860

Asp His His Phe Leu Glu Ala Ile Cys Cys Phe Pro Met Val Tyr Tyr
865                 870                 875                 880

Met Glu Gly Ser Val Asp Asn Leu Asp Ser Leu Leu Gln Cys Gly Ile
            885                 890                 895

Ile Tyr Ala Asp Asn Leu Val Val Asp Lys Glu Ser Thr Met Ser
        900                 905                 910

Ala Glu Glu Asp Tyr Met Ala Asp Ala Lys Thr Ile Val Asn Val Gln
        915                 920                 925

Thr Met Phe Arg Leu Phe Pro Ser Leu Ser Ile Thr Thr Glu Leu Thr
        930                 935                 940

His Pro Ser Asn Met Arg Phe Met Gln Phe Arg Ala Lys Asp Ser Tyr
945                 950                 955                 960

Ser Leu Ala Leu Ser Lys Leu Glu Lys Arg Glu Arg Glu Asn Gly Ser
            965                 970                 975

Asn Leu Ala Phe Met Phe Arg Leu Pro Phe Ala Ala Gly Arg Val Phe
```

-continued

```
                980                 985                 990
Ser Ile Ser Met Leu Asp Thr Leu Leu Tyr Gln Ser Phe Val Lys Asp
            995                1000                1005

Tyr Met Ile Thr Ile Thr Arg Leu Leu Leu Gly Leu Asp Thr Thr Pro
       1010                1015                1020

Gly Ser Gly Tyr Leu Cys Ala Met Lys Ile Thr Glu Gly Asp Leu Trp
1025                1030                1035                1040

Ile Arg Thr Tyr Gly Arg Leu Phe Gln Lys Leu Cys Ser Ser Ser Ala
            1045                1050                1055

Glu Ile Pro Ile Gly Ile Tyr Arg Thr Glu Ser His Val Phe Ser Thr
            1060                1065                1070

Ser Glu Pro His Asp Leu Arg Ala Gln Ser Gln Ile Ser Val Asn Val
       1075                1080                1085

Glu Asp Cys Glu Asp Thr Arg Glu Val Lys Gly Pro Trp Gly Ser Arg
       1090                1095                1100

Ala Gly Thr Gly Gly Ser Ser Gln Gly Arg His Thr Gly Gly Gly Asp
1105                1110                1115                1120

Pro Ala Glu His Pro Leu Leu Arg Arg Lys Ser Leu Gln Trp Ala Arg
            1125                1130                1135

Arg Leu Ser Arg Lys Ala Pro Lys Gln Ala Gly Arg Ala Ala Ala
            1140                1145                1150

<210> SEQ ID NO 34
<211> LENGTH: 200
<212> TYPE: PRT
<213> ORGANISM: Artificial Sequence
<220> FEATURE:
<223> OTHER INFORMATION: Description of Artificial Sequence:poly
      Gly flexible linker
<220> FEATURE:
<221> NAME/KEY: MOD_RES
<222> LOCATION: (6)..(200)
<223> OTHER INFORMATION: Gly at positions 6-200 may be present or
      absent

<400> SEQUENCE: 34

Gly Gly Gly Gly Gly Gly Gly Gly Gly Gly Gly Gly Gly Gly Gly
  1               5                  10                  15

Gly Gly Gly Gly Gly Gly Gly Gly Gly Gly Gly Gly Gly Gly Gly
             20                  25                  30

Gly Gly Gly Gly Gly Gly Gly Gly Gly Gly Gly Gly Gly Gly Gly
         35                  40                  45

Gly Gly Gly Gly Gly Gly Gly Gly Gly Gly Gly Gly Gly Gly Gly
     50                  55                  60

Gly Gly Gly Gly Gly Gly Gly Gly Gly Gly Gly Gly Gly Gly Gly
 65                  70                  75                  80

Gly Gly Gly Gly Gly Gly Gly Gly Gly Gly Gly Gly Gly Gly Gly
             85                  90                  95

Gly Gly Gly Gly Gly Gly Gly Gly Gly Gly Gly Gly Gly Gly Gly
        100                 105                 110

Gly Gly Gly Gly Gly Gly Gly Gly Gly Gly Gly Gly Gly Gly Gly
    115                 120                 125

Gly Gly Gly Gly Gly Gly Gly Gly Gly Gly Gly Gly Gly Gly Gly
130                 135                 140

Gly Gly Gly Gly Gly Gly Gly Gly Gly Gly Gly Gly Gly Gly Gly
            145                 150                 155                 160

Gly Gly Gly Gly Gly Gly Gly Gly Gly Gly Gly Gly Gly Gly Gly
```

```
                165              170             175
Gly Gly Gly Gly Gly Gly Gly Gly Gly Gly Gly Gly Gly Gly
            180             185             190
Gly Gly Gly Gly Gly Gly Gly Gly
        195             200

<210> SEQ ID NO 35
<211> LENGTH: 38
<212> TYPE: DNA
<213> ORGANISM: Artificial Sequence
<220> FEATURE:
<223> OTHER INFORMATION: Description of Artificial Sequence:Slo2
      overlap extension PCR amplification antisense primer oligo
      14 plus 5' Xba site for subcloning

<400> SEQUENCE: 35
cagggtctag attagagctg tgtctcgtcg cgagtctc                       38

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence:Slo2
      amplification sense primer oligo 15 and added
      Kozak consensus sequence for expression vector
      construction

<400> SEQUENCE: 36
ccaccatggc gcgggccaag ct                                        22

<210> SEQ ID NO 37
<211> LENGTH: 34
<212> TYPE: DNA
<213> ORGANISM: Artificial Sequence
<220> FEATURE:
<223> OTHER INFORMATION: Description of Artificial Sequence:Slo4
      amplification antisense primer oligo 20
      overlapping the stop codonin the EST sequence and
      5' XbaI restriction site to assist subcloning

<400> SEQUENCE: 37
tttatctaga atcaaagttg agtttcctcc cgag                           34

<210> SEQ ID NO 38
<211> LENGTH: 39
<212> TYPE: DNA
<213> ORGANISM: Artificial Sequence
<220> FEATURE:
<223> OTHER INFORMATION: Description of Artificial Sequence:Slo4
      amplification sense primer oligo 24 overlapping
      the initiator Met codon and 5' MunI site for
      subcloning and Kozak consensus sequence

<400> SEQUENCE: 38
atcccaattg ccgccatggt tgatttggag agcgaagtg                      39
```

SLO2, NOVEL POTASSIUM CHANNEL PROTEINS FROM HUMAN BRAIN

CROSS-REFERENCES TO RELATED APPLICATIONS

The present application is a division of U.S. Ser. No. 12/177,819, filed Jul. 22, 2008, which is a division of U.S. Ser. No. 11/325,764, filed Jan. 4, 2006, now U.S. Pat. No. 7,411,043, which is a continuation of U.S. Ser. No. 09/921,159, filed Aug. 1, 2001, now U.S. Pat. No. 7,041,494, which claims priority to U.S. Ser. No. 60/249,112, the contents of each of the above are herein incorporated by reference in the entirety.

STATEMENT AS TO RIGHTS TO INVENTIONS MADE UNDER FEDERALLY SPONSORED RESEARCH AND DEVELOPMENT

Not applicable.

BACKGROUND OF THE INVENTION

Potassium channels are involved in a number of physiological processes, including regulation of heartbeat, dilation of arteries, release of insulin, excitability of nerve cells, and regulation of renal electrolyte transport. Potassium channels are thus found in a wide variety of animal cells such as nervous, muscular, glandular, immune, reproductive, and epithelial tissue. These channels allow the flow of potassium in and/or out of the cell under certain conditions. For example, the outward flow of potassium ions upon opening of these channels makes the interior of the cell more negative, counteracting depolarizing voltages applied to the cell. These channels are regulated, e.g., by calcium sensitivity, voltage-gating, second messengers, extracellular ligands, and ATP-sensitivity.

Potassium channels are made by alpha subunits that fall into 8 families, based on predicted structural and functional similarities (Wei et al., *Neuropharmacology* 35(7):805-829 (1997)). Three of these families (Kv, Eag-related, and KQT, now referred to as KCNQ) share a common motif of six transmembrane domains and are primarily gated by voltage. Two other families, CNG and SK/IK, also contain this motif but are gated by cyclic nucleotides and calcium, respectively. The three other families of potassium channel alpha subunits have distinct patterns of transmembrane domains: inward rectifier potassium channels, Slo potassium channels, and TP potassium channels. Slo family potassium channels (also known as BK or "maxi" channels) are large conductance channel types, are voltage gated, have six to seven transmembrane domains, a pore loop domain, and a cytoplasmic tail domain involved in gating, e.g., ion (e.g., calcium) and pH regulation (see, e.g., Schreiber et al., *J. Biol. Chem.* 273:3509-3515 (1998); Butler et al., *Science* 261:221-224 (1993); Meera et al., *Proc. Natl. Acad. Sci. U.S.A.* 94(25):14066-71 (1997); Wei et al., *Neuron* 13:671-681 (1994)). The inward rectifier family of potassium channels (Kir), belong to a structural family containing 2 transmembrane domains (see, e.g., Lagrutta et al., *Jpn. Heart. J.* 37:651-660 1996)). Yet another functionally diverse family (TP, or "two-pore") contains 2 tandem repeats of this inward rectifier motif.

As described above, potassium channels are typically formed by four alpha subunits, and can be homomeric (made of identical alpha subunits) or heteromeric (made of two or more distinct types of alpha subunits). In addition, potassium channels have often been found to contain additional, structurally distinct auxiliary, or beta, subunits (e.g., Kv, Slo, and KCNQ potassium channel families; see, e.g., McManus et al., *Neuron* 14:645-650 (1995); Schopperle et al., *Neuron* 20:565-573 (1998); Brenner et al., *J. Biol. Chem.* 275:6453-6461 (1999); and WO 0050444). These beta subunits do not form potassium channels themselves, but instead they act as auxiliary subunits to modify the functional properties of channels formed by alpha subunits. For example, the Kv beta subunits are cytoplasmic and are known to increase the surface expression of Kv channels and/or modify inactivation kinetics of the channel (Heinemann et al., *J. Physiol.* 493: 625-633 (1996); Shi et al., *Neuron* 16(4):843-852 (1996)). In another example, the KCNQ family beta subunit, minK, primarily changes activation kinetics (Sanguinetti et al., *Nature* 384:80-83 (1996)).

The Slo family of potassium channels can be further divided into two subfamilies, based on homology. The first subfamily includes Slo1 and Slo3 (see, e.g., Elkins et al., *Proc. Nat'l Acad. Sci. USA* 83:8415 (1986); Atkinson et al., *Science* 253:551 (1991); Adelman et al., *Neuron* 9:209 (1992) (*Drosophila* Slo1); Bulter et al., *Science* 261:221-224 (1993); Dworetsky et al., *Mol Brain Res.* 27:189-193 (1994); Tseng-Crank et al., *Neuron* 13:1315-1330 (1994); McCobb et al., *Am. J. Physiol.* 269:H767-H777 (1995); Wallner et al., *Rec. Chan.* 3:185-199 (1995) (human and mouse Slo1); Schreiber et al., *J. Biol. Chem.* 273:3509-3515 (1998); WO 99/20754 (human and mouse Slo3). Slo1 is calcium activated, while Slo 3 is regulated by internal pH. Potassium channels from the second subfamily include *C. elegans* Slo2 and rat "SLACK" (Joiner et al., *Nat. Neurosci.* 1:462-469 (1998) (rat SLACK or Slo2); Yuan et al., *Nat. Neurosci.* 3:771-779 (2000); Lim et al., *Gene* 240:35-43 (1999) (*C. elegans* "Slo2"). The members of the second subfamily share the same structural motifs, are also voltage gated, and can also be gated by other ions, e.g., calcium or chloride (see, e.g., Joiner et al., supra, Yuan et al., supra). However, the members of the second subfamily appear to share less overall homology to Slo1 and Slo3 channels.

Slo channels play a role in a wide variety of physiological processes ranging from renal salt secretion (Wang et al., *Annu. Rev. Physiol.* 59:413-36 (1997), regulation of neuronal and glandular secretion (Lingle et al., *Ion Channels* 4:261-301 (1996); Robitaille et al., *Neuron* 11:645-655 (1993); Peterson et al., *Nature* 307:693-696 (1984); Robitaille & Charlton, *J. Neurosci.* 12:297-305 (1992), sensory perception (Ramanthan et al., *Science* 283:215-217 (1999); Navaratnam et al., *Neuron* 5:1077-1085 (1997)) regulation of smooth muscle tone (Brayden & Nelson, *Science* 256:532-535 (1992)) and control of neuronal excitability (Knaus et al., *J. Neurosci.* 16:955-963 (1996); Robitaille & Charlton, *J. Neurosci.* 12:297-305 (1992); Lancaster et al., *J. Neurosci.* 11:23-30 (1991); Robitaille et al., *Neuron* 11:645-655 (1993)).

SUMMARY OF THE INVENTION

The present invention therefore provides, for the first time, a gene encoding Slo 4, a new member of the Slo family and the Slo2/4 subfamily of potassium channels. In addition, the present invention presents for the first time the gene encoding human Slo2.

In one aspect, the present invention provides an isolated nucleic acid encoding a Slo4 polypeptide comprising an alpha subunit of a Slo potassium channel, the polypeptide: (i) forming, with at least one additional Slo alpha subunit, a Slo potassium channel comprising the characteristic of voltage-gating; and (ii) comprising a sequence having at least 60% amino acid sequence identity to an amino acid sequence of SEQ ID NO:4.

In another aspect, the present invention provides an isolated nucleic acid encoding a Slo4 polypeptide, the nucleic acid specifically hybridizing under stringent conditions to a nucleotide sequence of SEQ ID NO:3.

In one embodiment, the nucleic acid encodes an amino acid sequence of SEQ ID NO:4. In another embodiment, the nucleic acid comprises a nucleotide sequence of SEQ ID NO:3. In another embodiment, the nucleic acid selectively hybridizes under moderately stringent hybridization conditions to a nucleotide sequence of SEQ ID NO:3.

In one embodiment, the nucleic acid is amplified by at least one pair of primers that selectively hybridize under stringent hybridization conditions to the same sequence as the primers selected from the group consisting of:

```
                                        (SEQ ID NO: 23)
5'-GGCGTCTGCTTGATTGGTGTTAGGA-3'

(SEQ ID NO: 24)
5'-ATCAAAGTTGAGTTTCCTCCCGAG-3'

(SEQ ID NO: 25)
5'-CCCGGAGCATCTACCGTACATCTTC-3'

(SEQ ID NO: 26)
5'-CCAGCTGTTCAAACTGTATGGGTAG-3'

(SEQ ID NO: 27)
5'-GCTTGGAGGACCATGTTTCAGGAGT-3'

(SEQ ID NO: 28)
5'-ATGGTTGATTTGGAGAGCGAAGTG-3'

(SEQ ID NO: 29)
5'-CAATTTTGAGAGCATGGGCTGTGAAAG-3'

(SEQ ID NO: 30)
5'-GACTTATGGATCAGAACTTATGCCCAG-3'

(SEQ ID NO: 31)
5'-CATCTGGTGTAGTTTCATCTTCTGATTGG-3'.
```

In one aspect, the present invention provides a method of detecting a nucleic acid, the method comprising contacting the nucleic acid with an isolated Slo4 nucleic acid of the invention.

In one aspect, the present invention provides host cells comprising expression vectors comprising Slo4 nucleic acids of the invention.

In another aspect, the present invention provides an isolated Slo4 polypeptide comprising an alpha subunit of a Slo potassium channel, the polypeptide: (i) forming, with at least one additional Slo alpha subunit, a Slo potassium channel comprising the characteristic of voltage-gating; and (ii) comprising a sequence having at least 60% amino acid sequence identity to an amino acid sequence of SEQ ID NO:4.

In another embodiment, the potassium channel further comprises the characteristic of rapid activation.

In one embodiment, the polypeptide specifically binds to antibodies generated against SEQ ID NO:4. In another embodiment, the polypeptide comprises an alpha subunit of a homomeric or a heteromeric potassium channel. In one embodiment, the polypeptide has a molecular weight of between about 134 kD to about 144 kD.

In another embodiment, the polypeptide encodes human Slo4. In another embodiment, the polypeptide has an amino acid sequence of SEQ ID NO:4.

In one aspect, the invention provides an antibody that specifically binds to the Slo4 polypeptide of the invention.

In another aspect, the present invention provides a method for identifying a compound that increases or decreases ion flux through a potassium channel, the method comprising the steps of: (i) contacting the compound with a Slo4 polypeptide, the polypeptide (a) forming, with at least one additional Slo alpha subunit, a Slo potassium channel having the characteristic of voltage-gating; and (b) comprising a sequence having at least 60% amino acid sequence identity to an amino acid sequence of SEQ ID NO:4; and (ii) determining the functional effect of the compound upon the potassium channel.

In one embodiment, the functional effect is a physical effect or a chemical effect. In another embodiment, the functional effect is determined by measuring ion flux, changes in ion concentrations, changes in current or changes in voltage. In another embodiment, the functional effect is determined by measuring ligand binding to the channel.

In one embodiment, the polypeptide is expressed in a eukaryotic host cell or cell membrane. In another embodiment, the polypeptide is recombinant.

In one aspect, the present invention provides a method for identifying a compound that increases or decreases ion flux through a potassium channel comprising a Slo4 polypeptide, the method comprising the steps of: (i) entering into a computer system an amino acid sequence of at least 25 amino acids of a Slo4 polypeptide or at least 75 nucleotides of a nucleic acid encoding the Slo4 polypeptide, the Slo4 polypeptide comprising a subsequence having at least 60% amino acid sequence identity to an amino acid sequence of SEQ ID NO:4; (ii) generating a three-dimensional structure of the polypeptide encoded by the amino acid sequence; (iii) generating a three-dimensional structure of the potassium channel comprising the Slo4 polypeptide; (iv) generating a three-dimensional structure of the compound; and (v) comparing the three-dimensional structures of the polypeptide and the compound to determine whether or not the compound binds to the polypeptide.

In another aspect, the present invention provides a method of modulating ion flux through a Slo potassium channel comprising a Slo4 polypeptide to treat disease in a subject, the method comprising the step of administering to the subject a therapeutically effective amount of a compound identified using the methods of the invention.

In another aspect, the present invention provides a method of detecting the presence of hSlo4 in human tissue, the method comprising the steps of: (i) isolating a biological sample; (ii) contacting the biological sample with an hSlo4-specific reagent that selectively associates with hSlo4; and, (iii) detecting the level of hSlo4-specific reagent that selectively associates with the sample.

In one embodiment, the hSlo4-specific reagent is selected from the group consisting of: hSlo4-specific antibodies, hSlo4-specific oligonucleotide primers, and hSlo4-nucleic acid probes.

In another aspect, the present invention provides, in a computer system, a method of screening for mutations of a human Slo4 gene, the method comprising the steps of: (i) entering into the computer a first nucleic acid sequence encoding a Slo4 polypeptide having an amino acid sequence of SEQ ID NO:4, and conservatively modified versions thereof; (ii) comparing the first nucleic acid sequence with a second nucleic acid sequence having substantial identity to the first nucleic acid sequence; and (iii) identifying nucleotide differences between the first and second nucleic acid sequences.

In one embodiment, the second nucleic acid sequence is associated with a disease state.

In one aspect, the present invention provides an isolated nucleic acid encoding a Slo2 polypeptide comprising an alpha subunit of a Slo potassium channel, the polypeptide: (i) forming, with at least one additional Slo alpha subunit, a Slo potassium channel comprising the characteristic of voltage-gating; and (ii) comprising an amino acid sequence of SEQ ID NO:2.

In another aspect, the present invention provides an isolated nucleic acid encoding a Slo2 polypeptide, wherein the nucleic acid is amplified by primers that selectively hybridize under stringent hybridization conditions to the same sequence as the primers selected from the group consisting of:

```
                                          (SEQ ID NO: 18)
5'-TTAGAGCTGTGTCTCGTCGCGAGTCTC-3' (14)

(SEQ ID NO: 19)
5'-ATGGCGCGGGCCAAGCT-3' (15)

(SEQ ID NO: 20)
5'-GAGACAGGGAGGAGTCCAGGCTGAA-3' (16)

(SEQ ID NO: 21)
5'-CGTGGGCCAGAGGCTTCCTGTAGAA-3' (17)
```

In one embodiment, the nucleic acid comprises a nucleotide sequence of SEQ ID NO:1.

In one aspect, the present invention provides a method of detecting a nucleic acid, the method comprising contacting the nucleic acid with an isolated Slo2 nucleic acid of the invention.

In one aspect, the present invention provides host cells comprising expression vectors comprising Slo2 nucleic acids of the invention.

In one aspect, the present invention provides an isolated Slo2 polypeptide comprising an alpha subunit of a Slo potassium channel, the polypeptide: (i) forming, with at least one additional Slo alpha subunit, a Slo potassium channel comprising the characteristic of voltage-gating; and (ii) comprising a sequence having an amino acid sequence of SEQ ID NO:2.

In one embodiment, the potassium channel further comprises the characteristic of rapid activation.

In one embodiment, the polypeptide encoded by the nucleic acid comprises an alpha subunit of a heteromeric or homomeric potassium channel. In another embodiment, the polypeptide has a molecular weight of between about 134 kD to about 144 kD.

In one aspect, present the invention provides an antibody that specifically binds to the Slo4 polypeptide of the invention.

In another aspect, the present invention provides a method for identifying a compound that increases or decreases ion flux through a potassium channel, the method comprising the steps of: (i) contacting the compound with a Slo4 polypeptide, the polypeptide (a) forming, with at least one additional Slo alpha subunit, a Slo potassium channel having the characteristic of voltage-gating; and (b) comprising a sequence having an amino acid sequence of SEQ ID NO:2; and (ii) determining the functional effect of the compound upon the potassium channel.

In one embodiment, the functional effect is a physical effect or a chemical effect. In another embodiment, the functional effect is determined by measuring ion flux, changes in ion concentrations, changes in current or changes in voltage.

In another embodiment, the functional effect is determined by measuring ligand binding to the channel.

In one embodiment, the polypeptide is expressed in a eukaryotic host cell or cell membrane. In another embodiment, the polypeptide is recombinant.

In another aspect, the present invention provides a method for identifying a compound that increases or decreases ion flux through a potassium channel comprising a Slo2 polypeptide, the method comprising the steps of: (i) entering into a computer system an amino acid sequence of SEQ ID NO:2; (ii) generating a three-dimensional structure of the polypeptide encoded by the amino acid sequence; (iii) generating a three-dimensional structure of the potassium channel comprising the Slo2 polypeptide; (iv) generating a three-dimensional structure of the compound; and (v) comparing the three-dimensional structures of the polypeptide and the compound to determine whether or not the compound binds to the polypeptide.

In another aspect, the present invention provides a method of modulating ion flux through a Slo potassium channel comprising a Slo2 polypeptide to treat disease in a subject, the method comprising the step of administering to the subject a therapeutically effective amount of a compound identified using the methods of the invention.

In another aspect, the present invention provides a method of detecting the presence of hSlo2 in human tissue, the method comprising the steps of: (i) isolating a biological sample; (ii) contacting the biological sample with an hSlo2-specific reagent that selectively associates with hSlo2; and, (iii) detecting the level of hSlo2-specific reagent that selectively associates with the sample.

In one embodiment, the hSlo2-specific reagent is selected from the group consisting of: hSlo2-specific antibodies, hSlo2-specific oligonucleotide primers, and hSlo2-nucleic acid probes.

In another aspect, the present invention provides, in a computer system, a method of screening for mutations of a human Slo2 gene, the method comprising the steps of: (i) entering into the computer a first nucleic acid sequence encoding a Slo2 polypeptide having an amino acid sequence of SEQ ID NO:2, and conservatively modified versions thereof; (ii) comparing the first nucleic acid sequence with a second nucleic acid sequence having substantial identity to the first nucleic acid sequence; and (iii) identifying nucleotide differences between the first and second nucleic acid sequences.

In one embodiment, the second nucleic acid sequence is associated with a disease state.

BRIEF DESCRIPTION OF THE DRAWINGS

FIG. 1. Amino acid alignment of the complete human Slo2 amino acid sequence to the amino acids sequences of rat SLACK and the partial human cDNA KIAA1422. Identical residues are shaded and amino acid numbers are given at the left margin. Human Slo2 and rat SLACK are 93% identical and are probably orthologous genes. The pattern of divergence between human Slo2 and rat SLACK is not typical for orthologous potassium channels. KIAA1422 is a partial cDNA from the hSlo2 gene, but differs in several key ways. First, it has an alternative amino terminus that is highly divergent from those of human Slo2 and rat SLACK. It is also clearly truncated on the 3' end. The human Slo2 DNA and amino acid sequences can not be readily predicted from KIAA1422 or rat SLACK.

FIG. 2. Amino acid alignment of human Slo2 and human Slo4. Identical residues are shaded and amino acid numbers are given at the left margin. Six predicted transmembrane domains are underlined with solid lines. The potassium channel "signature sequence" or pore loop is underlined with a dotted line. A dashed line indicates a tail region that has been implicated in Slo channel calcium and chloride gating (Yuan et al., *Nat. Neurosci.* 3:771-779 (2000); Wei et al., *Neuron*, 13:671-681 (1994)). The two amino acid sequences are approximately 70% identical.

DETAILED DESCRIPTION OF THE INVENTION

Figure 3:
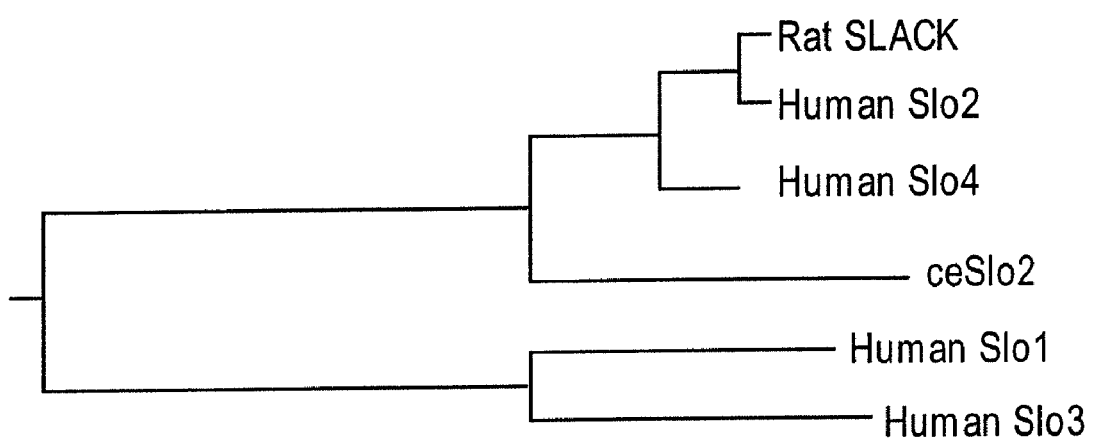
FIG. 3. Phylogenetic tree of the Slo potassium channel gene family. Two main branches define two distinct gene subfamilies. Human Slo2 and Slo4 are in a subfamily that also includes rat SLACK and the *C. elegans* Slo2 gene (ceSlo2). Note that *C. elegans* Slo2 branches separately from both Slo2 and Slo4, suggesting that it is not orthologous to either of these genes.

The present invention provides for the first time nucleic acids encoding Slo4 potassium channels. The present invention also provides the sequence of human Slo2. These polypeptide monomers are members of the Slo family of potassium channels, and the Slo2/4 subfamily. Members of this family are polypeptide subunits of potassium channels having six transmembrane regions and a pore-loop domain, as well as a cytoplasmic tail.

Both human Slo2 and Slo4 are expressed in the heart and central nervous system and appear to contribute to the modulation of neuronal excitability, because both Slo2 and Slo4 begin to activate in a voltage range below the typical thresholds for action potential generation. They also appear to be involved in action potential repolarization and refractory period and the control of neurotransmitter release, as is the case for other Slo family members. The expression of human Slo2 and Slo4 in peripheral tissues such as skeletal muscle, heart and spleen indicate that they may also be involved in regulating muscle contraction, heart rate, airway tone, inflammation, and lymphocyte proliferation. In addition, modulators of Slo2 and Slo4 should be useful in treating disorders of neuronal excitability related to increased levels of neuronal activity or abnormal neurotransmitter release. This includes neuropathic pain, epilepsy and seizure disorders, depression and other psychotic disorders such as bipolar disease and schizophrenia, migraine and anxiety. Modulators could also be useful in treating disorders of learning and memory caused by diseases such as Alzheimer's, or to enhance learning and memory in the aging population. In some cells, enhancement of Slo2 and Slo4 currents will cause greater hyperpolarization and decrease depolarization-based calcium influxes, providing neuroprotection. In other cells in which the calcium influx is independent of voltage, blockers of Slo2 and Slo4 may reduce the driving force for calcium entry, again providing neuroprotection.

The invention therefore provides methods of screening for activators and inhibitors of potassium channels that contain a Slo2 or a Slo4 alpha subunit. Such modulators of potassium channel activity are useful for treating disorders, including CNS disorders, such as neuropathic pain, epilepsy and other seizure disorders, migraines, anxiety, psychotic disorders such as schizophrenia, bipolar disease, and depression. Such modulators are also useful as neuroprotective agents (e.g., to prevent stroke). Modulators could also be useful in treating cognitive disorders of learning and memory caused by diseases such as Alzheimer's, or to enhance learning and memory in the aging population, as well providing neuroprotection. Finally, such modulators could be useful for treating hypercontractility of muscles, cardiac arrhythmias, inflammation, asthma, and as immunosuppressants or stimulants.

Furthermore, the invention provides assays for Slo2 and Slo4 activity where Slo2 or Slo4 acts as a direct or indirect reporter molecule. Such uses of Slo2 and Slo4 as a reporter molecule in assay and detection systems have broad applications, e.g., Slo2 or Slo4 can be used as a reporter molecule to measure changes in potassium concentration, membrane potential, current flow, ion flux, transcription, signal transduction, receptor-ligand interactions, second messenger concentrations, in vitro, in vivo, and ex vivo. In one embodiment, Slo2 or Slo4 can be used as an indicator of current flow in a particular direction (e.g., outward or inward potassium flow), and in another embodiment, Slo2 or Slo4 can be used as an indirect reporter via attachment to a second reporter molecule such as green fluorescent protein.

The invention also provides for methods of detecting Slo2 and Slo4 nucleic acid and protein expression, allowing investigation of the channel diversity provided by Slo2 and Slo4 family members, as well as diagnosis of disorders, including CNS disorders, such as neuropathic pain, epilepsy and other seizure disorders, migraines, anxiety, psychotic disorders such as schizophrenia, bipolar disease, and depression, cognitive disorders of learning and memory caused by diseases such as Alzheimer's, hypercontractility of muscles, cardiac arrhythmias, inflammation, and asthma.

Finally, the invention provides for a method of screening for mutations of Slo2 and Slo4 genes or proteins. The invention includes, but is not limited to, methods of screening for mutations in Slo2 or Slo4 with the use of a computer. Similarly, the invention provides for methods of identifying the three-dimensional structure of Slo2 and Slo4 polypeptides, e.g., human Slo2 and human Slo4, as well as the resulting computer readable images or data that comprise the three dimensional structure of Slo2 and Slo4 polypeptides. Other methods for screening for mutations of Slo2 and Slo4 genes or proteins include high density oligonucleotide arrays, PCR, immunoassays and the like.

Functionally, Slo2 and Slo4 polypeptides are alpha subunits of a Slo potassium channel. Slo2 and Slo4 potassium channels are potassium selective and voltage gated (e.g., the number of channels that open during a voltage step increases with increasing depolarization) In addition, these channels may be regulated by other means, e.g., calcium, chloride, or pH (see, e.g., Yuan et al., *Nat. Neurosci.* 8:771-779 (2000); see also Schreiber, supra, and Butler, supra). Typically, such channels are heteromeric or homomeric and contain four alpha subunits or monomers each with six or seven transmembrane domains. Heteromeric Slo channels can comprise one or more Slo2 or Slo4 alpha subunits along with one or more additional alpha subunits from the Slo family (see, e.g., McManus et al., *Neuron* 14:645-650 (1995); Schopperle et al., *Neuron* 20:565-573 (1998); Brenner et al., *J. Biol. Chem.* 275:6453-6461 (1999); and WO 0050444). Slo2 and Slo4 channels may also be homomeric. In addition, such homomeric channels may comprise one or more auxiliary beta subunits. The presence of Slo2 or Slo4 in a potassium channel may also modulate the activity of the heteromeric channel and thus enhance channel diversity, for example by altering a channel characteristic such as conductance. Channel diversity is also enhanced with alternatively spliced forms of Slo2 and Slo4 genes.

Figure 4A:
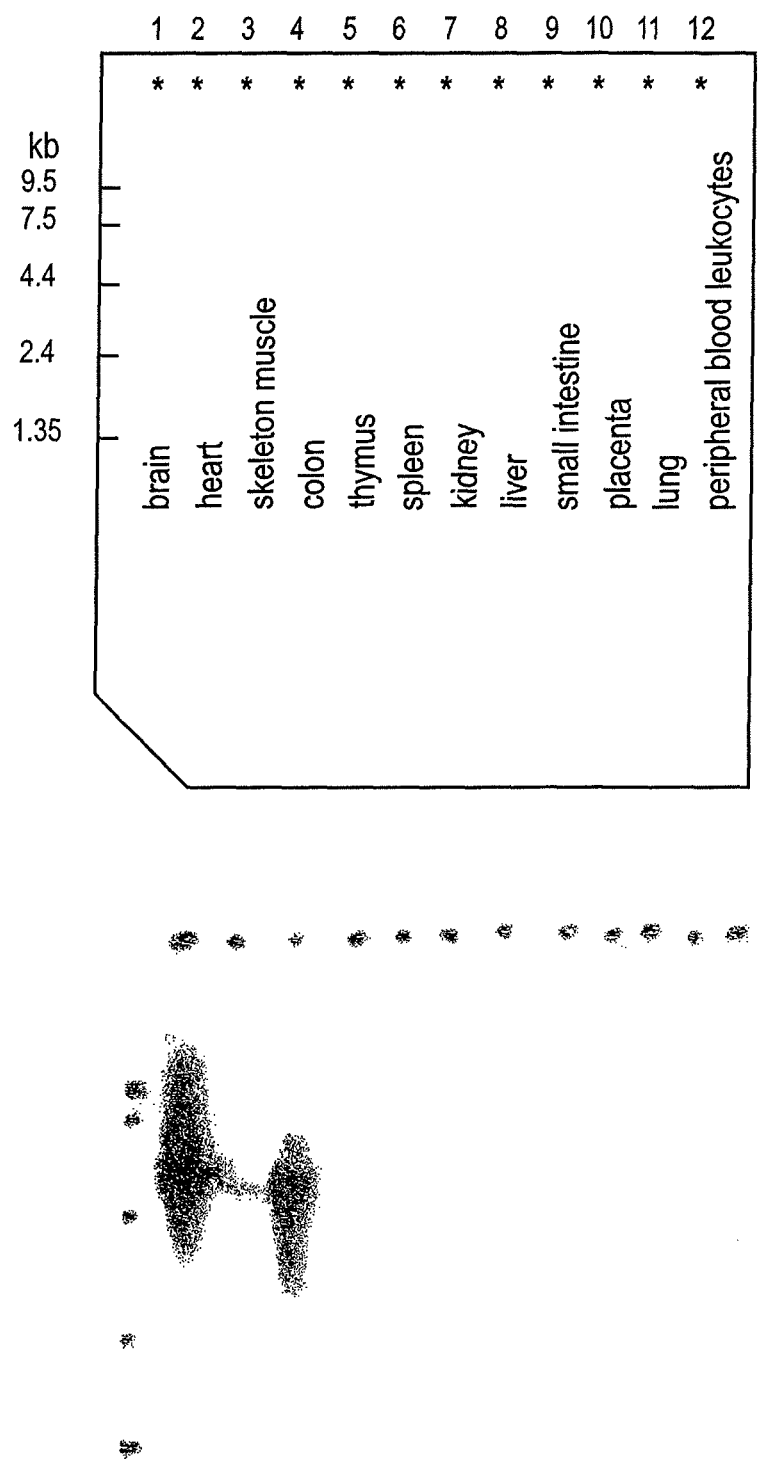
FIG. 4. Messenger RNA expression patterns of human Slo2. Blots were probed with a $^{32}$P-labeled Slo2 PCR fragment and hybridized with standard high stringency procedures. (A) Northern blot of Slo2. Strong bands of approximately 5 Kb are seen in brain and skeletal muscle. Weaker bands of 6+Kb are also present and may represent alternative splice variants or incompletely processed RNAs. Similar bands are also seen in heart and spleen. (B) mRNA dot blot hybridized with the same Slo2 probe. Note the strong signals seen in CNS tissues, skeletal muscle, spleen, heart, pituitary and ovary.
Figure 4B:
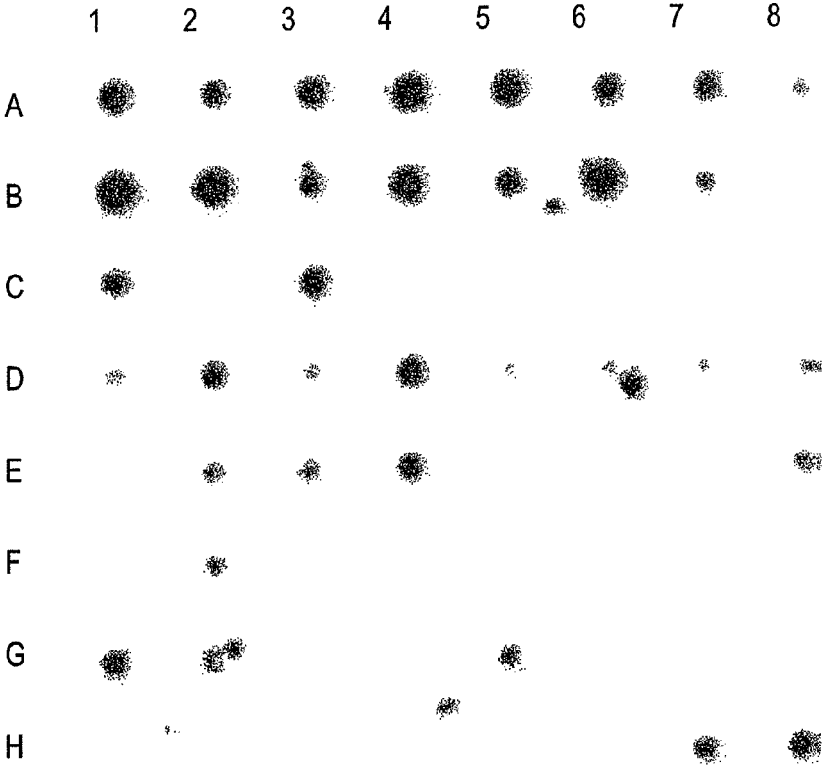

Slo2 nucleic acids are expressed in the human CNS tissues (cerebellum, cerebral cortex, occipital lobe, temporal lobe, putamen, nucleus accumbens, amygdala, caudate nucleus, frontal lobe, hippocampus, substantia nigra, and thalamus), skeletal muscle, spleen, heart, pituitary, ovary, placenta, fetal brain, and fetal spleen (see FIG. 4). Slo 4 cDNA has been amplified in the human brain, and Slo4 nucleic acids are expressed in human liver, brain, heart (atrium), skeletal muscle, spleen, kidney, GI tract (colon, small intestine), placenta, lung, testis, bladder, fetal brain, fetal kidney, and fetal liver, as well as in additional tissues (see FIG. 7).

Structurally, the nucleotide sequence of human Slo2 (SEQ ID NO:1) encodes a polypeptide monomer of about 1235 amino acids (SEQ ID NO:2) with a predicted molecular weight of about 139 Kd, and a range of approximately 134 Kd to 164 Kd.

The present invention also provides polymorphic variants of the human Slo2 depicted in SEQ ID NO:2: variant #1, in which a serine residue is substituted for the alanine residue at amino acid position 24; variant #2, in which a threonine residue is substituted for the alanine residue at amino acid position 39; variant #3, in which a threonine residue is substituted for the serine residue at amino acid position 113; and variant #4, in which a lysine residue is substituted for the arginine residue at amino acid position 1105.

Structurally, the nucleotide sequence of human Slo4 (SEQ ID NO:3) encodes a protein of about 1135 amino acids (SEQ ID NO:4) with a predicted molecular weight of about 130 Kd, and a range of approximately 125 Kd to 135 Kd.

The present invention also provides polymorphic variants of the human Slo4 depicted in SEQ ID NO:4: variant #1, in which a valine residue is substituted for the methionine residue at amino acid position 39; variant #2, in which a alanine residue is substituted for the serine residue at amino acid position 87; variant #3, in which a serine residue is substituted for the threonine residue at amino acid position 547; and variant #4, in which an isoleucine residue is substituted for the valine residue at amino acid position 1098.

Specific regions of Slo2 or Slo4 nucleotide and amino acid sequence may be used to identify Slo2 or Slo4 polymorphic variants, interspecies homologs, and alleles. This identification can be made in vitro, e.g., under stringent hybridization conditions and sequencing, or by using the sequence information in a computer system for comparison with other nucleotide sequences, or using antibodies raised to Slo2 or Slo4. Typically, identification of Slo2 or Slo4 polymorphic variants, orthologs, and alleles is made by comparing the amino acid sequence (or the nucleic acid encoding the amino acid sequence) to SEQ ID NO:2 or 4, or a conserved region such as the core transmembrane domain (pore loop and S1-S6 transmembrane domains), or the tail domain. Amino acid identity of approximately at least 60% or above, preferably 70%, 65%, 75%, 80%, 85%, most preferably 90-95% or above in the full length amino acid sequence typically demonstrates that a protein is a Slo2 or Slo4 polymorphic variant, interspecies homolog, or allele. Amino acid identity of approximately at least 60%, 65%, 70%, or 75%, 75% or above, preferably 80%, 85%, most preferably 90-95% or above in the core transmembrane domain (S1-S6 plus the pore loop) or the C-terminal cytoplasmic tail domain typically demonstrates that a protein is a Slo2 or Slo4 polymorphic variant, interspecies homolog, or allele. Sequence comparison is typically performed using the BLAST or BLAST 2.0 algorithm with default parameters, discussed below.

Slo2 or Slo4 polymorphic variants, interspecies homologs, and alleles can be confirmed by expressing or co-expressing the putative Slo2 or Slo4 polypeptide monomer and examining whether it forms a potassium channel with Slo family functional characteristics, such as voltage gating, and Slo2 or Slo4 characteristics such as relatively rapid activation and deactivation. This assay is used to demonstrate that a protein having about 60% or greater, preferably 65%, 70%, 75%, 80%, 85%, 90%, or 95% or greater amino acid identity to a conserved region of Slo2 or Slo4 shares the same functional characteristics as Slo2 or Slo4 and is therefore a species of Slo2 or Slo4. Typically, human Slo2 or Slo4 having the amino acid sequence of SEQ ID NO:2 or 4 is used as a positive control in comparison to the putative Slo2 or Slo4 protein to demonstrate the identification of a Slo2 or Slo4 polymorphic variant, ortholog, conservatively-modified variant, mutant, or allele.

Slo2 or Slo4 nucleotide and amino acid sequence information may also be used to construct models of Slo voltage-gated potassium channels in a computer system. These models are subsequently used to identify compounds that can activate or inhibit voltage-gated potassium channels comprising Slo2 or Slo4 polypeptides. Such compounds that modulate the activity of channels comprising Slo2 or Slo4 polypeptides can be used to investigate the role of Slo2 or Slo4 polypeptides in modulation of channel activity and in channel diversity.

The isolation of biologically active human Slo2 and human Slo4 for the first time provides a means for assaying for inhibitors and activators of voltage-gated potassium channels that comprise Slo2 or Slo4 subunits. Biologically active Slo2 or Slo4 polypeptides are useful for testing inhibitors and activators of voltage-gated potassium channels comprising subunits of Slo2 or Slo4 and/or other Slo members such as Slo1 or Slo3, using in vivo and in vitro expression that measure, e.g., changes in voltage or current. Such activators and inhibitors identified using a potassium channel comprising at least one Slo2 or Slo4 subunit, optionally up to four Slo2 or Slo4 subunits, can be used to further study voltage gating, channel kinetics and conductance properties of potassium channels. Such activators and inhibitors are useful as pharmaceutical agents for treating diseases involving abnormal ion flux, e.g., CNS disorders, such as neuropathic pain, epilepsy and other seizure disorders, migraines, anxiety, psychotic disorders such as schizophrenia, bipolar disease, and depression. Such modulators are also useful as neuroprotective agents (e.g., to prevent stroke). Modulators could also be useful in treating cognitive disorders of learning and memory caused by diseases such as Alzheimer's, or to enhance learning and memory in the aging population, as well providing neuroprotection. Finally, such modulators could be useful for treating hypercontractility of muscles, cardiac arrhythmias, inflammation, asthma, and as immunosuppressants or stimulants.

Methods of detecting Slo2 or Slo4 nucleic acids and polypeptides and expression of channels comprising Slo2 or Slo4 polypeptides are also useful for diagnostic applications for diseases involving abnormal ion flux, e.g., as described above. For example, chromosome localization of the gene encoding human Slo2 or Slo4 can be used to identify diseases caused by and associated with Slo2 or Slo4. Methods of detecting Slo2 or Slo4 are also useful for examining the role of Slo2 or Slo4 in channel diversity and modulation of channel activity.

II. DEFINITIONS

As used herein, the following terms have the meanings ascribed to them unless specified otherwise.

"Slo4" refers to a polypeptide that is a subunit or monomer of a Slo or Slo4 potassium channel, and a member of the Slo family. When Slo4 is part of a homomeric potassium channel, the channel has the characteristic of voltage gating and rapid deactivation. In addition, when Slo4 is part of a heteromeric potassium channel, it can confer altered characteristics. Slo4 has a core transmembrane domain corresponding to amino acids 64-282 of SEQ ID NO:4, which comprises the pore loop domain and the S1-S6 transmembrane domains. Slo4 also has a C-terminal cytoplasmic tail domain from amino acids 336-1135 of SEQ ID NO:4.

The term Slo4 therefore refers to Slo4 polymorphic variants, alleles, mutants, and orthologs (interspecies homologs) that: (1) have a sequence that has greater than about 60% amino acid sequence identity, preferably about 65%, 70%, 75%, 80%, 85%, 90%, or 95% amino acid sequence identity using a sequence comparison algorithm such as BLASTP with the parameters described herein, to a Slo4 amino acid sequence of SEQ ID NO:4 or a conserved region such as the core transmembrane domain or the C-terminal cytoplasmic tail; (2) bind to antibodies, e.g., polyclonal or monoclonal antibodies, raised against an immunogen comprising an amino acid sequence of SEQ ID NO:4 or an immunogenic fragment thereof, and conservatively modified variants thereof; (3) specifically hybridize under highly and/or moderately stringent hybridization conditions to a sequence of SEQ ID NO:3, and conservatively modified variants thereof; or (4) are amplified by primers that specifically hybridize under highly and/or moderately stringent hybridization conditions to the same sequence as a primer set selected from the group consisting of SEQ ID NOS:23-31.

"Slo2" refers to a polypeptide that is a subunit or monomer of a Slo or Slo4 potassium channel, and a member of the Slo family. When Slo2 is part of a homomeric potassium channel, the channel has the characteristic of voltage gating and rapid deactivation. In addition, when Slo2 is part of a heteromeric potassium channel, it can confer altered characteristics. Slo2 has a core transmembrane domain from amino acids 98-335 of SEQ ID NO:2, which comprises the pore loop domain and the S1-S6 transmembrane domains. Slo2 also has a C-terminal cytoplasmic tail domain from amino acids 283-1235 of SEQ ID NO:2.

The term Slo2 therefore refers to Slo4 polymorphic variants, alleles, and mutants that: (1) have amino acid sequence identity greater than about 95%, 96%, 97%, 98%, 99%, or more amino acid sequence identity using a sequence comparison algorithm such as BLASTP with the parameters described herein, to a Slo2 amino acid sequence of SEQ ID NO:2 or a conserved region such as the core transmembrane domain or the C-terminal cytoplasmic tail; (2) bind to antibodies, e.g., polyclonal or monoclonal antibodies, raised against an immunogen comprising an amino acid sequence of SEQ ID NO:2 or an immunogenic fragment thereof, and conservatively modified variants thereof; (3) specifically hybridize under highly and/or moderately stringent hybridization conditions to a sequence of SEQ ID NO:1, and conservatively modified variants thereof; or (4) are amplified by primers that specifically hybridize under highly and/or moderately stringent hybridization conditions to the same sequence as a primer set selected from the group consisting of SEQ ID NOS:5-22, in particular a primer set with at least one primer selected from the group consisting of SEQ ID NOS: 18-21.

The phrase "voltage-gated" activity or "voltage-gating" refers to a characteristic of a potassium channel composed of individual polypeptide monomers or subunits. Generally, the probability of a voltage-gated potassium channel opening increases as a cell is depolarized. Voltage-gated potassium channels primarily allow efflux of potassium because they have greater probabilities of being open at membrane potentials more positive than the equilibrium potential for potassium ($E_K$) in typical cells. $E_K$, or the equilibrium potential for potassium, depends on the relative concentrations of potassium found inside and outside the cell membrane, and is typically between −60 and −100 mV for mammalian cells. $E_K$ is the membrane potential at which there is no net flow of potassium ion because the electrical potential (i.e., voltage potential) driving potassium influx is balanced by the concentration gradient (the [K$^+$] potential) directing potassium efflux. This value is also known as the "reversal potential" or the "Nernst" potential for potassium. Some voltage-gated potassium channels undergo inactivation, which can reduce potassium efflux at higher membrane potentials. Potassium channels can also allow potassium influx in certain instances when they remain open at membrane potentials negative to $E_K$ (see, e.g., Adams & Nonner, in *Potassium Channels*, pp. 40-60 (Cook, ed., 1990)). The characteristic of voltage gating can be measured by a variety of techniques for measuring changes in current flow and ion flux through a channel, e.g., by changing the [K$^+$] of the external solution and measuring the activation potential of the channel current (see, e.g., U.S. Pat. No. 5,670,335), by measuring current with patch clamp techniques or voltage clamp under different conditions, and by measuring ion flux with radiolabeled tracers or voltage-sensitive dyes under different conditions.

"Large conductance" refers to the conductance of certain potassium channels. In native cells, conductances of these channels range from about 40 to 50 pS to over 200 pS (see, e.g., Latorre et al., *Annu. Rev. Physio.* 51:385-399 (19891)). For example, Slo1 and Slo3 channels have conductances near the upper end of this range, while Slo2 channels have conductances close to the lower end.

"Homomeric channel" refers to a Slo2 or a Slo4 channel composed of identical alpha subunits, whereas "heteromeric channel" refers to a Slo channel composed of at least one Slo2 or Slo4 alpha subunit, plus at least one other different type of alpha subunit from another Slo family member such as Slo1 or Slo3. Both homomeric and heteromeric channels can include auxiliary beta subunits. Typically, the channel is composed of four alpha subunits and the channel can be heteromeric or homomeric.

A "beta subunit" is a polypeptide monomer that is an auxiliary subunit of a potassium channel composed of alpha subunits; however, beta subunits alone cannot form a channel (see, e.g., U.S. Pat. No. 5,776,734). Beta subunits are known, for example, to increase the number of channels by helping the alpha subunits reach the cell surface, change activation kinetics, and change the sensitivity of natural ligands binding to the channels. Beta subunits can be outside of the pore region and associated with alpha subunits comprising the pore region. They can also contribute to the external mouth of the pore region.

The phrase "functional effects" in the context of assays for testing compounds affecting a channel comprising Slo2 or Slo4 includes the determination of any parameter that is indirectly or directly under the influence of the channel. It includes e.g., direct, physical effects, such as ligand binding, and indirect, chemical or phenotypic effects, e.g., changes in ion flux and membrane potential, and other physiologic effects such as increases or decreases of transcription or hormone release. "Functional effects" include in vitro (biochemical or ligand binding assays using, e.g., isolated protein, cell lysates or cell membranes), in vivo (cell- and animal-based assays), and ex vivo activities.

"Determining the functional effect" refers to examining the effect of a compound that has a direct physical effect on a Slo2 or Slo4 subunit or channel comprising a Slo2 or Slo4 subunit, e.g., ligand binding, or indirect chemical or phenotypic effects on channel comprising a Slo2 or a Slo4 subunit, e.g., increases or decreases ion flux in a cell or cell membrane.

The ion flux can be any ion that passes through a channel and analogues thereof, e.g., potassium, rubidium. Preferably, the term refers to the functional effect of the compound on the channels comprising Slo2 or Slo4, e.g., changes in ion flux including radioisotopes, current amplitude, membrane potential, current flow, conductance, transcription, protein binding, phosphorylation, dephosphorylation, second messenger concentrations (cAMP, cGMP, Ca$^{2+}$, IP$_3$), ligand binding, changes in ion concentration, and other physiological effects such as hormone and neurotransmitter release, as well as changes in voltage and current. Such functional effects can be measured by any means known to those skilled in the art, e.g., patch clamping, voltage-sensitive dyes, ion sensitive dyes, whole cell currents, radioisotope efflux, inducible markers, and the like.

"Inhibitors," "activators" or "modulators" of voltage-gated potassium channels comprising a Slo2 or a Slo4 polypeptide refer to inhibitory or activating molecules identified using in vitro and in vivo assays for Slo2 or a Slo4 channel function. Inhibitors are compounds that decrease, block, prevent, delay activation, inactivate, desensitize, or down regulate the channel, e.g., antagonists. Activators are compounds that increase, open, activate, facilitate, enhance activation, sensitize or up regulate channel activity, e.g., agonists. Such assays for inhibitors and activators include e.g., expressing a Slo2 or a Slo4 polypeptide in cells, cell extracts, or cell membranes and then measuring flux of ions through the channel and determining changes in polarization (i.e., electrical potential). Alternatively, cells expressing endogenous Slo2 or a Slo4 channels can be used in such assays. Isolated naturally occurring or recombinant Slo2 or Slo4-comprising channels or Slo2 or Slo4 subunits, or cell extracts containing the same can also be used in ligand binding assays to identify such modulators. To examine the extent of inhibition, samples or assays comprising a Slo2 or a Slo4 subunit or channel are treated with a potential activator or inhibitor and are compared to control samples without the inhibitor. Control samples (untreated with inhibitors) are assigned a relative Slo2 or a Slo4 activity value of 100% Inhibition of channels comprising Slo2 or a Slo4 is achieved when the Slo2 or a Slo4 activity value relative to the control is about 90%, preferably 50%, more preferably 25-0%. Activation of channels comprising Slo2 or a Slo4 is achieved when the Slo2 or a Slo4 activity value relative to the control is 110%, more preferably 150%, most preferably at least 200-500% higher or 1000% or higher.

"Biologically active" Slo2 or a Slo4 polypeptides refers to Slo2 or a Slo4 polypeptides that have the ability to form a potassium channel having the characteristic of voltage-gating and rapid deactivation, tested as described above.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated Slo2 or a Slo4 nucleic acid is separated from open reading frames that flank the Slo2 or Slo4 gene and encode proteins other than Slo2 or Slo4. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure. Isolated or purified Slo2 and 4 can be recombinant or naturally occurring.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid (e.g., a sphingolipid), fatty acid, polynucleotide, oligonucleotide, etc., to be tested for the capacity to directly or indirectly modulation lymphocyte activation. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 5000 daltons, preferably less than about 2000 daltons, preferably between about 100 to about 1000 daltons, more preferably between about 200 to about 500 daltons.

The term "pain" refers to all categories of pain, including pain that is described in terms of stimulus or nerve response, e.g., somatic pain (normal nerve response to a noxious stimulus) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic neuropathy (see, e.g., *Harrison's Principles of Internal Medicine*, pp. 93-98 (Wilson et al., eds., 12th ed. 1991); Williams et al., *J. of Medicinal Chem.* 42:1481-1485 (1999), herein each incorporated by reference in their entirety).

"Somatic" pain, as described above, refers to a normal nerve response to a noxious stimulus such as injury or illness, e.g., trauma, burn, infection, inflammation, or disease process such as cancer, and includes both cutaneous pain (e.g., skin, muscle or joint derived) and visceral pain (e.g., organ derived).

"Neuropathic" pain, as described above, refers to pain resulting from injury to or chronic changes in peripheral and/or central sensory pathways, where the pain often occurs or persists without an obvious noxious input.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., *J. Biol. Chem.* 273(52):35095-35101 (1998).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);

2) Aspartic acid (D), Glutamic acid (E);

3) Asparagine (N), Glutamine (Q);

4) Arginine (R), Lysine (K);

5) Isoleucine (I), Leucine (L), Methionine (M), Valine (V);

6) Phenylalanine (F), Tyrosine (Y), Tryptophan (W);

7) Serine (S), Threonine (T); and

8) Cysteine (C), Methionine (M)

(see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically about 18 to 350 amino acids long, e.g., the transmembrane regions, pore loop domain, and the C-terminal tail domain. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" is a composition detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, digoxigenin, or haptens and proteins for which antisera or monoclonal antibodies are available (e.g., the polypeptide of SEQ ID NO:2 or 4 can be made detectable, e.g., by incorporating a radiolabel into the peptide, and used to detect antibodies specifically reactive with the peptide).

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, preferably 65%, 70%, 75%, 80%, 85%, 90%, or 95% identity over a specified region of SEQ ID NO:2 or 4), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to Slo2 or Slo4 nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

For preparation of monoclonal or polyclonal antibodies, any technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)).

An "anti-Slo2" or "anti-Slo4" antibody is an antibody or antibody fragment that specifically binds a polypeptide encoded by a Slo2 or Slo4 gene, cDNA, or a subsequence thereof.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, antibodies, e.g., polyclonal or monoclonal antibodies, raised to Slo2 or a Slo4, as shown in SEQ ID NOS:2 or 4, or splice variants, or portions thereof, can be selected to obtain only those polyclonal antibodies that are specifically immunoreactive with Slo2 or Slo4 family members and not with other Slo proteins. This selection may be achieved by subtracting out antibodies that cross-react with molecules such as other Slo family members. In addition, antibodies, e.g., polyclonal or monoclonal antibodies, raised to human Slo2 or human Slo4 polymorphic variants, alleles, and conservatively modified variants can be selected to obtain only those antibodies that recognize human Slo2 or human Slo4, but not other Slo2 or Slo4 orthologs, e.g., rat Slo2 (rat SLACK). A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa and the like, e.g., cultured cells, explants, and cells in vivo.

"Biological sample" as used herein is a sample of biological tissue or fluid that contains Slo2 or Slo4 polypeptides or nucleic acid encoding a Slo2 or Slo4 protein. Such samples include, but are not limited to, tissue isolated from humans. Biological samples may also include sections of tissues such as frozen sections taken for histologic purposes. A biological sample is typically obtained from a eukaryotic organism, preferably eukaryotes such as fungi, plants, insects, protozoa, birds, fish, reptiles, and preferably a mammal such as rat, mice, cow, dog, guinea pig, or rabbit, and most preferably a primate such as chimpanzees or humans.

III. ISOLATING A GENE ENCODING A SLO2 OR SLO4 POLYPEPTIDE

A. General Recombinant DNA Methods

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (Kb) or base pairs (bp). These are estimates derived from agarose or acrylamide gel electrophoresis, from sequenced nucleic acids, or from published DNA sequences. For proteins, sizes are given in kilodaltons (kD) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859-1862 (1981), using an automated synthesizer, as described in Van Devanter et. al., *Nucleic Acids Res.* 12:6159-6168 (1984). Purification of oligonucleotides is by either native acrylamide gel electrophoresis or by anion-exchange HPLC as described in Pearson & Reanier, *J. Chrom.* 255:137-149 (1983).

The sequence of the cloned genes and synthetic oligonucleotides can be verified after cloning using, e.g., the chain termination method for sequencing double-stranded templates of Wallace et al., *Gene* 16:21-26 (1981).

B. Cloning Methods for the Isolation of Nucleotide Sequences Encoding Slo2 or Slo4 Polypeptides In general, the nucleic acid sequences encoding Slo2 or a Slo4 and related nucleic acid sequence homologs are cloned from cDNA and genomic DNA libraries or isolated using amplification techniques with oligonucleotide primers. For example, Slo2 or a Slo4 sequences are typically isolated from human nucleic acid (genomic or cDNA) libraries by hybridizing with a nucleic acid probe or polynucleotide, the sequence of which can be derived from SEQ ID NOS:1 or 3. A suitable tissue from which Slo2 or Slo4 RNA and cDNA can be isolated is nervous system tissue such as whole brain, or any other tissues in which Slo2 or Slo4 is expressed (see, e.g., FIGS. 4 and 7).

Amplification techniques using primers can also be used to amplify and isolate Slo2 or Slo4. The following primers can also be used to amplify a sequence of human Slo2:

```
                                        (SEQ ID NO: 5)
5'-CACCACGGAGCTCACCCACCCTTCC-3'  (1)

(SEQ ID NO: 6)
5'-CGCGTCTTCAGCATCAGCATGTTGGAC-3'  (2)

(SEQ ID NO: 7)
5'-CTGGTAGAGCAGTGTGTCCAACATGCTG-3'  (3)

(SEQ ID NO: 8)
5'-ACTGCATGAAGCGCATGTTGGAAGGGTG-3'  (4)

(SEQ ID NO: 9)
5'-CCCATTGCCGGCCGTCTCTGCCGAG-3'  (5)

(SEQ ID NO: 10)
5'-CTTGAACCCGTAGGCCTTGGCGTCTTC-3'  (6)

(SEQ ID NO: 11)
5'-CACACCACGTGGTCAGCAAACTTGACG-3'  (7)

(SEQ ID NO: 12)
5'-GCAGTTGGGGCGAAGTCCTTCACGG-3'  (8)

(SEQ ID NO: 13)
5'-CACCTTCAAGGAGCGGCTCAAGCTG-3'  (9)

(SEQ ID NO: 14)
5'-GACGTGTGCACCAGCAGGGTGATGAG-3'  (10)

(SEQ ID NO: 15)
5'-GTTTCACGTCAAGTTTGCTGACCACG-3'  (11)

(SEQ ID NO: 16)
5'-CCGTACGTGCGGATCCACAGGTCG-3'  (12)

(SEQ ID NO: 17)
5'-CGTGAAGGACTACATGATCACCATC-3'  (13)
```

```
                                              (SEQ ID NO: 18)
5'-TTAGAGCTGTGTCTCGTCGCGAGTCTC-3' (14)

(SEQ ID NO: 19)
5'-ATGGCGCGGGCCAAGCT-3' (15)

(SEQ ID NO: 20)
5'-GAGACAGGGAGGAGTCCAGGCTGAA-3' (16)

(SEQ ID NO: 21)
5'-CGTGGGCCAGAGGCTTCCTGTAGAA-3' (17)

(SEQ ID NO: 22)
5'-GCTCCCAGATGTTGCCTTTGTAGCTG-3' (18)
```

The following primers can be used to amplify Slo4:

```
                                              (SEQ ID NO: 23)
5'-GGCGTCTGCTTGATTGGTGTTAGGA-3' (19)

(SEQ ID NO: 24)
5'-ATCAAAGTTGAGTTTCCTCCCGAG-3' (20)

(SEQ ID NO: 25)
5'-CCCGGAGCATCTACCGTACATCTTC-3' (21)

(SEQ ID NO: 26)
5'-CCAGCTGTTCAAACTGTATGGGTAG-3' (22)

(SEQ ID NO: 27)
5'-GCTTGGAGGACCATGTTTCAGGAGT-3' (23)

(SEQ ID NO: 28)
5'-ATGGTTGATTTGGAGAGCGAAGTG-3' (24)

(SEQ ID NO: 29)
5'-CAATTTTGAGAGCATGGGCTGTGAAAG-3' (25)

(SEQ ID NO: 30)
5'-GACTTATGGATCAGAACTTATGCCCAG-3' (26)

(SEQ ID NO: 31)
5'-CATCTGGTGTAGTTTCATCTTCTGATTGG-3' (27)
```

These primers can be used, e.g., to amplify either the full length sequence or a probe of one to several hundred nucleotides, which is then used to screen a library for full-length Slo2 or Slo4.

Nucleic acids encoding Slo2 or Slo4 family members can also be isolated from expression libraries using antibodies as probes. Such polyclonal or monoclonal antibodies can be raised using the sequence of SEQ ID NO:2 or 4, or an immunogenic portion thereof, e.g., the C-terminal tail region, located at amino acids 336-1235 for Slo2 and amino acids 323-1135 for Slo4.

Slo2 and Slo4 polymorphic variants, orthologs, and alleles that are substantially identical to a conserved region of Slo2 or Slo4 can be isolated using Slo2 or Slo4 nucleic acid probes and oligonucleotides under stringent hybridization conditions, by screening libraries. Alternatively, expression libraries can be used to clone Slo2 or Slo4 polymorphic variants, orthologs, and alleles by detecting expressed homologs immunologically with antisera or purified antibodies made against human Slo2 or Slo4 or immunogenic portions thereof (e.g., the tail (C-terminal) regions of human Slo2 or Slo4), which also recognize and selectively bind to the Slo2 or Slo4 homolog.

To make a cDNA library, one should choose a source that is rich in Slo2 or Slo4 mRNA, e.g., whole brain. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263-269 (1983); Sambrook et al., supra; Ausubel et al., supra).

For a genomic library, the DNA is extracted from the tissue and either mechanically sheared or enzymatically digested to yield fragments of about 12-20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180-182 (1977). Colony hybridization is carried out as generally described in Grunstein et al., *Proc. Natl. Acad. Sci. USA.*, 72:3961-3965 (1975).

An alternative method of isolating Slo2 or Slo4 nucleic acid and its orthologs, alleles, mutants, polymorphic variants, and conservatively modified variants combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of human Slo2 or Slo4 directly from mRNA, from cDNA, from genomic libraries or cDNA libraries. Degenerate oligonucleotides can be designed to amplify Slo2 or Slo4 homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of Slo2 or Slo4 encoding mRNA in physiological samples, for nucleic acid sequencing, or for other purposes. Genes amplified by the PCR reaction can be purified from agarose gels and cloned into an appropriate vector.

Gene expression of Slo2 or Slo4 can also be analyzed by techniques known in the art, e.g., reverse transcription and amplification of mRNA, isolation of total RNA or poly A$^+$ RNA, northern blotting, dot blotting, in situ hybridization, RNase protection, high density polynucleotide array technology and the like.

Synthetic oligonucleotides can be used to construct recombinant Slo2 or Slo4 genes for use as probes or for expression of protein. This method is performed using a series of overlapping oligonucleotides usually 40-120 by in length, representing both the sense and nonsense strands of the gene. These DNA fragments are then annealed, ligated and cloned. Alternatively, amplification techniques can be used with precise primers to amplify a specific subsequence of the Slo2 or Slo4 gene. The specific subsequence is then ligated into an expression vector.

The nucleic acid encoding Slo2 or Slo4 is typically cloned into intermediate vectors before transformation into prokaryotic or eukaryotic cells for replication and/or expression. These intermediate vectors are typically prokaryote vectors, e.g., plasmids, or shuttle vectors.

C. Expression in Prokaryotes and Eukaryotes

To obtain high level expression of a cloned gene, such as those cDNAs encoding Slo2 or Slo4, one typically subclones Slo2 or Slo4 into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al., and Ausubel et al, supra. Bacterial expression systems for expressing Slo2 or Slo4 protein are available in, e.g., *E. coli, Bacillus* sp., and *Salmonella* (Palva et al., *Gene* 22:229-235 (1983); Mosbach et al., *Nature* 302: 543-545 (1983). Kits for such expression systems are commercially available. Eukaryotic expression systems for mammalian cells, yeast, and insect cells are well known in the art and are also commercially available.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the Slo2 or Slo4 encoding nucleic acid in host cells. A typical expression cassette thus contains a promoter operably linked to the nucleic acid sequence encoding Slo2 or Slo4 and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal. Inducible expression vectors are often chosen if expression of the protein of interest is detrimental to eukaryotic cells.

Some expression systems have markers that provide gene amplification such as thymidine kinase and dihydrofolate reductase. Alternatively, high yield expression systems not involving gene amplification are also suitable, such as using a baculovirus vector in insect cells, with a Slo2 or Slo4 encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of Slo2 or Slo4 protein, which are then purified using standard techniques (see, e.g., Colley et al., *J. Biol. Chem.* 264:17619-17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing Slo2 or Slo4.

After the expression vector is introduced into the cells, the transfected cells are cultured under conditions favoring expression of Slo2 or Slo4, which is recovered from the culture using standard techniques identified below.

IV. PURIFICATION OF SLO2 OR SLO4 POLYPEPTIDES

Either naturally occurring or recombinant Slo2 or Slo4 can be purified for use in functional assays. Naturally occurring Slo2 or Slo4 monomers can be purified, e.g., from human tissue such as whole brain or cerebral cortex and any other source of a Slo2 or Slo4 homolog. Recombinant Slo2 or Slo4 monomers can be purified from any suitable expression system.

The Slo2 or Slo4 monomers may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant Slo2 or Slo4 monomers are being purified. For example, proteins having established molecular adhesion properties can be reversible fused to the Slo2 or Slo4 monomers. With the appropriate ligand, the Slo2 or Slo4 monomers can be selectively adsorbed to a purification column and then freed from the column in a relatively pure form. The fused protein is then removed by enzymatic activity. Finally the Slo2 or Slo4 monomers could be purified using immunoaffinity columns.

A. Purification of Slo2 or Slo4 Monomers from Recombinant Bacteria

Recombinant proteins are expressed by transformed bacteria in large amounts, typically after promoter induction; but expression can be constitutive. Promoter induction with IPTG is one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of the Slo2 or Slo4 monomers inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2-3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. Human Slo monomers are separated from other bacterial proteins by standard separation techniques, e.g., with Ni-NTA agarose resin.

Alternatively, it is possible to purify the Slo2 or Slo4 monomers from bacteria periplasm. After lysis of the bacteria, when the Slo2 or Slo4 monomers are exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying Slo2 or Slo4 Monomers

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of the Slo2 or Slo4 monomers can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The Slo2 or Slo4 monomers can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

V. IMMUNOLOGICAL DETECTION OF SLO2 OR SLO4 POLYPEPTIDES

In addition to the detection of Slo2 or Slo4 genes and gene expression using nucleic acid hybridization technology, one can also use immunoassays to detect the Slo2 or Slo4 monomers of the invention. Immunoassays can be used to qualitatively or quantitatively analyze the hSlo2 or Slo4 monomers. A general overview of the applicable technology can be found in Harlow & Lane, *Antibodies: A Laboratory Manual* (1988).

A. Antibodies to Slo2 or Slo4 Monomers

Methods of producing polyclonal and monoclonal antibodies that react specifically with the Slo2 or Slo4 monomers, or Slo2 or Slo4 monomers from particular species such as human Slo2 or Slo4 are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495-497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)).

A number of immunogens comprising portions of Slo2 or Slo4 monomers may be used to produce antibodies specifically reactive with Slo2 or Slo4 monomers. For example, recombinant Slo2 or Slo4 monomers or an antigenic fragment thereof, such as a conserved region (see, e.g., the pore loop or the C-terminal tail domains), can be isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, *Eur. J. Immunol.* 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., *Science* 246:1275-1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-Slo family proteins and other Slo family proteins, using a competitive binding immunoassay. Specific polyclonal antisera and monoclonal antibodies will usually bind with a $K_d$ of at least about 0.1 mM, more usually at least about 1 µM, preferably at least about 0.1 µM or better, and most preferably, 0.01 µM or better. Antibodies specific only for a particular Slo2 or Slo4 ortholog, such as human Slo2 or Slo4, can also be made, by subtracting out other cross-reacting orthologs from a species such as a non-human mammal.

Once the specific antibodies against Slo2 or Slo4 are available, the polypeptides can be detected by a variety of immunoassay methods. For a review of immunological and immunoassay procedures, see *Basic and Clinical Immunology* (Stites & Terr eds., 7$^{th}$ ed. 1991). Moreover, the immunoassays of the present invention can be performed in any of several configurations, which are reviewed extensively in Enzyme Immunoassay (Maggio, ed., 1980); and Harlow & Lane, supra.

B. Immunological Binding Assays

The Slo2 or Slo4 polypeptides of the invention can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7$^{th}$ ed. 1991). Immunological binding assays (or immunoassays) typically use an antibody that specifically binds to a protein or antigen of choice (in this case Slo2 or Slo4 or an antigenic subsequence thereof). The antibody (e.g., anti-Slo2 or Slo4) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled Slo2 or Slo4 polypeptide or a labeled anti-Slo2 or Slo4 antibody. Alternatively, the labeling agent may be a third moiety, such a secondary antibody, which specifically binds to the antibody/Slo2 or Slo4 complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111:1401-1406 (1973); Akerstrom et al., *J. Immunol.* 135:2589-2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-Competitive Assay Formats

Immunoassays for detecting the Slo2 or Slo4 in samples may be either competitive or noncompetitive. Noncompetitive immunoassays are assays in which the amount of antigen is directly measured. In one preferred "sandwich" assay, for example, the anti-Slo2 or Slo4 subunit antibodies can be bound directly to a solid substrate on which they are immobilized. These immobilized antibodies then capture Slo2 or Slo4 present in the test sample. The Slo2 or Slo4 monomers are thus immobilized and then bound by a labeling agent, such as a second Slo2 or Slo4 antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of the Slo2 or Slo4 present in the sample is measured indirectly by measuring the amount of known, added (exogenous) Slo2 or Slo4 displaced (competed away) from an anti-Slo2 or Slo4 antibody by the unknown Slo2 or Slo4 present in a sample. In one competitive assay, a known amount of the Slo2 or Slo4 is added to a sample and the sample is then contacted with an antibody that specifically binds to the Slo2 or Slo4. The amount of exogenous Slo2 or Slo4 bound to the antibody is inversely proportional to the concentration of the Slo2 or Slo4 present in the sample. In a particularly preferred embodiment, the antibody is immobilized on a solid substrate. The amount of Slo2 or Slo4 bound to the antibody may be determined either by measuring the amount of Slo2 or Slo4 present in a Slo2 or Slo4/antibody complex, or alternatively by measuring the amount of remaining uncomplexed protein. The amount of Slo2 or Slo4 may be detected by providing a labeled Slo2 or Slo4 molecule.

A hapten inhibition assay is another preferred competitive assay. In this assay the known Slo2 or Slo4 is immobilized on a solid substrate. A known amount of anti-Slo2 or Slo4 antibody is added to the sample, and the sample is then contacted with the immobilized Slo2 or Slo4. The amount of anti-Slo2 or Slo4 antibody bound to the known immobilized Slo2 or Slo4 is inversely proportional to the amount of Slo2 or Slo4 present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-Reactivity Determinations

Immunoassays in the competitive binding format can also be used for crossreactivity determinations for Slo2 or Slo4. For example, a Slo2 or Slo4 protein at least partially corresponding to an amino acid sequence of SEQ ID NO:2 or 4 or an immunogenic region thereof, such as a conserved region (e.g., the pore loop or tail domain), can be immobilized to a solid support. Other proteins such as other Slo family members are added to the assay so as to compete for binding of the antisera to the immobilized antigen. The ability of the added proteins to compete for binding of the antisera to the immobilized protein is compared to the ability of the Slo2 or Slo4 or immunogenic portion thereof to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs. Antibodies that specifically bind only to Slo2 or Slo4, or only to particular orthologs of Slo2 or Slo4, such as human Slo2 or Slo4, can also be made using this methodology.

The immunoabsorbed and pooled antisera are then used in a competitive binding immunoassay as described above to compare a second protein, thought to be perhaps Slo2 or Slo4 or an allele, ortholog, or polymorphic variant thereof, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by Slo2 or Slo4 that is required to inhibit 50% of binding, then the second protein is said to specifically bind to the polyclonal antibodies generated to the respective Slo2 or Slo4 immunogen.

Other Assay Formats

Western blot (immunoblot) analysis is used to detect and quantify the presence of the Slo2 or Slo4 in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind Slo2 or Slo4. The anti-Slo2 or Slo4 antibodies specifically bind to Slo2 or Slo4 on the solid support. These antibodies may be directly labeled or alternatively may be subsequently detected using labeled antibodies (e.g., labeled sheep anti-mouse antibodies) that specifically bind to the anti-Slo2 or Slo4 antibodies.

Other assay formats include liposome immunoassays (LIA), which use liposomes designed to bind specific molecules (e.g., antibodies) and release encapsulated reagents or markers. The released chemicals are then detected according to standard techniques (see, Monroe et al., *Amer. Clin. Prod. Rev.* 5:34-41 (1986)).

Reduction of Non-Specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecule (e.g., streptavidin), which is either inherently detectable or covalently bound to a signal system, such as a detectable enzyme, a fluorescent compound, or a chemiluminescent compound. The ligands and their targets can be used in any suitable combination with antibodies that recognize hSlo2 or Slo4, or secondary antibodies that recognize anti-hSlo2 or Slo4 antibodies.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see, U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally, simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

VI. ASSAYS FOR MODULATORS OF SLO2 OR SLO4

A. Assays

Introduction

Human Slo2 or Slo4 and alleles, orthologs, and polymorphic variants are subunits of potassium channels. The activity of a potassium channel comprising Slo2 or Slo4 can be assessed using a variety of in vitro and in vivo assays, e.g., measuring current, measuring membrane potential, measuring ligand binding, measuring ion flux, e.g., potassium, or rubidium, measuring ion concentration, measuring second messengers and transcription levels, using potassium-dependent yeast growth assays, measuring ligand binding, and using, e.g., voltage-sensitive dyes, ion sensitive dyes such as potassium sensitive dyes, radioactive tracers, and patch-clamp electrophysiology.

Furthermore, such assays can be used to test for inhibitors and activators of channels comprising Slo2 or Slo4. Such modulators of a potassium channel are useful for treating various disorders involving potassium channels. Such modulators of potassium channel activity are useful for treating disorders, including CNS disorders, such as neuropathic pain, epilepsy and other seizure disorders, migraines, anxiety, psychotic disorders such as schizophrenia, bipolar disease, and depression. Such modulators are also useful as neuroprotective agents (e.g., to prevent stroke). Modulators could also be useful in treating cognitive disorders of learning and memory caused by diseases such as Alzheimer's, or to enhance learning and memory in the aging population, as well providing neuroprotection. Finally, such modulators could be useful for treating hypercontractility of muscles, cardiac arrhythmias, inflammation, asthma, and as immunosuppressants or stimulants.

Such modulators are also useful for investigation of the channel diversity provided by Slo2 or Slo4 and the regulation/modulation of potassium channel activity provided by Slo2 or Slo4.

Modulators of the Slo potassium channels are tested using biologically active Slo2 or Slo4, either recombinant or naturally occurring, preferably human Slo2 or Slo4. Slo2 or Slo4 can be isolated, co-expressed or expressed in a cell, or expressed in a membrane derived from a cell. In such assays, Slo2 or Slo4 is expressed alone to form a homomeric potassium channel or is co-expressed with a second alpha subunit (e.g., another Slo family member, e.g., Slo1 or Slo3) so as to form a heteromeric potassium channel. Slo2 or Slo4 polypeptides can also be expressed with additional beta subunits. Modulation is tested using one of the in vitro or in vivo assays described herein.

Samples or assays that are treated with a potential potassium channel inhibitor or activator are compared to control samples without the test compound, to examine the extent of modulation. Control samples (untreated with activators or inhibitors) are assigned a relative potassium channel activity value of 100. Inhibition of channels comprising a Slo2 or Slo4 polypeptide is achieved when the potassium channel activity value relative to the control is about 90%, preferably 50%, more preferably 25%. Activation of channels comprising a Slo2 or Slo4 polypeptide is achieved when the potassium channel activity value relative to the control is 110%, more preferably 150%, more preferable 200% higher. Compounds that increase the flux of ions will cause a detectable increase in the ion current density by increasing the probability of a channel comprising a Slo2 or Slo4 polypeptide being open, by decreasing the probability of it being closed, by increasing conductance through the channel, and/or by allowing the passage of ions.

Preferably, the Slo2 or Slo4 polypeptide used in the assay will have the sequence displayed in SEQ ID NO:2 or 4 or a conservatively modified variant thereof. Alternatively, the Slo2 or Slo4 of the assay will be derived from a eukaryote and include an amino acid subsequence having substantial amino acid sequence identity to a conserved region (see, e.g., pore loop or tail domain) of human Slo2 or Slo4. Generally, the amino acid sequence identity will be at least 60%, preferably at least 65%, 70%, 75%, 80%, 85%, or 90%, most preferably at least 95% or higher.

In Vitro Assays

Assays to identify compounds with potassium channel modulating activity can be performed in vitro, e.g., binding assays. Purified recombinant or naturally occurring Slo2 or Slo4 protein, or a channel comprising Slo 2 or Slo4 protein, can be used in the in vitro methods of the invention. In addition to purified Slo2 or Slo4 protein or channel comprising the same, the recombinant or naturally occurring Slo2 or Slo4 protein can be part of a cellular lysate or a cell membrane. As described below, the assay can be either solid state or soluble. Preferably, the protein or membrane is bound to a solid support, either covalently or non-covalently. Often, the in vitro assays of the invention are ligand or toxin binding or ligand affinity assays, either non-competitive or competitive. Other in vitro assays include measuring changes in spectroscopic (e.g., fluorescence, absorbance, refractive index), hydrodynamic (e.g., shape), chromatographic, or solubility properties for the protein or channel. Cell membranes or lysates can also be used to measure changes in polarization (i.e., electrical potential) of the cell or membrane expressing the potassium channel comprising a Slo2 or Slo4 polypeptide, as described below.

In Vivo Assays

In another embodiment, Slo2 or Slo4 protein is expressed in a cell, and functional, e.g., physical and chemical or phenotypic, changes are assayed to identify potassium channel modulators. For example, using cell- or animal based assays, changes in ion flux may be assessed by determining changes in polarization (i.e., electrical potential) of the cell or membrane expressing the potassium channel comprising a Slo2 or Slo4 polypeptide. A preferred means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., *New Engl. J. Med.* 336:1575-1595 (1997)). Whole cell currents are conveniently determined using the standard methodology (see, e.g., Hamil et al., *PFlugers. Archiv.* 391:85 (1981). Other known assays include: radiolabeled rubidium flux assays and fluorescence assays using voltage-sensitive dyes or ion sensitive dyes (see, e.g., Vestergarrd-Bogind et al., *J. Membrane Biol.* 88:67-75 (1988); Daniel et al., *J. Pharmacol. Meth.* 25:185-193 (1991); Holevinsky et al., *J. Membrane Biology* 137:59-70 (1994)). Assays for compounds capable of inhibiting or increasing potassium flux through the channel proteins comprising a Slo2 or Slo4 polypeptide can be performed by application of the compounds to a bath solution in contact with and comprising cells having a channel of the present invention (see, e.g., Blatz et al., *Nature* 323:718-720 (1986); Park, *J. Physiol.* 481:555-570 (1994)). Generally, the compounds to be tested are present in the range from 1 µM to 100 mM.

The effects of the test compounds upon the function of the channels can be measured by changes in the electrical currents or ionic flux or by the consequences of changes in currents and flux. Changes in electrical current or ionic flux are measured by either increases or decreases in flux of ions such as potassium or rubidium ions. The ions can be measured in a variety of standard ways. They can be measured directly by concentration changes of the ions, e.g., changes in intracellular concentrations, or indirectly by membrane potential or by radio-labeling of the ions. Consequences of the test compound on ion flux can be quite varied. Accordingly, any suitable physiological change can be used to assess the influence of a test compound on the channels of this invention.

For example, the effects of a test compound can be measured by a ligand or toxin binding assay. One can also measure a variety of effects such as transmitter release (e.g., dopamine), intracellular calcium changes, hormone release (e.g., insulin), transcriptional changes to both known and uncharacterized genetic markers (e.g., northern blots), cell volume changes (e.g., in red blood cells), immunoresponses (e.g., T cell activation), changes in cell metabolism such as cell growth or pH changes, and changes in intracellular second messengers such as cyclic nucleotides.

Slo2 or Slo4 orthologs, alleles, polymorphic variants, and conservatively modified variants will generally confer substantially similar properties on a channel comprising a Slo2 or Slo4 polypeptide, as described above. In a preferred embodiment, the cell placed in contact with a compound that is suspected to be a Slo2 or Slo4 homolog is assayed for increasing or decreasing ion flux in a eukaryotic cell, e.g., an oocyte of *Xenopus* (e.g., *Xenopus laevis*) or a mammalian cell such as a CHO or HeLa cell. Channels that are affected by compounds in ways similar to Slo2 or Slo4 are considered homologs or orthologs of Slo2 or Slo4.

Animal Models

Animal models also find use in screening for potassium channel modulators. Transgenic animal technology, including gene knockout technology as a result of homologous recombination with an appropriate gene targeting vector, or gene overexpression, will result in the absence or increased expression of the Slo2 or Slo4 protein. When desired, tissue-specific expression or knockout of the Slo2 or Slo4 protein may be necessary. Transgenic animals generated by such methods find use as animal models of abnormal ion flux and are additionally useful in screening for modulators of potassium channels.

B. Modulators

The compounds tested as modulators of Slo channels comprising a Slo2 or Slo4 subunit can be any small organic compound, or a biological entity, such as a protein, e.g., a peptide or antibody, sugar, nucleic acid, e.g., an antisense molecule, or lipid. Alternatively, modulators can be genetically altered versions of a Slo2 or Slo4 subunit. Typically, test compounds will be small organic molecules, antibodies, antisense molecules, and peptides. Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), carbohydrate libraries (see, e.g., Liang et al., *Science,* 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

In one embodiment, the invention provides solid phase based in vitro assays in a high throughput format, where the cell or tissue expressing a Slo channel comprising a human Slo2 or Slo4 subunit is attached to a solid phase substrate. In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 96 modulators. If 1536 well plates are used, then a single plate can easily assay from about 100-about 1500 different compounds. It is possible to assay many plates per day; assay screens for up to about 6,000, 20,000, 50,000, or 100,000 or more different compounds are possible using the integrated systems of the invention.

C. Solid State and Soluble High Throughput Assays

In one embodiment the invention provides high throughput soluble assays using, e.g., isolated potassium channels comprising a Slo2 or Slo4 polypeptide; a membrane comprising a Slo2 or Slo4 potassium channel, or a cell or tissue expressing potassium channels comprising a Slo2 or Slo4 polypeptide, either naturally occurring or recombinant. In another embodiment, the invention provides solid phase based in vitro assays in a high throughput format, where Slo2 or Slo4 potassium channel attached to a solid phase substrate. In another assay, the cell membrane or cell comprising the channel can be attached to a solid phase substrate. In yet another embodiment, the test compound is attached to a solid phase substrate.

In the high throughput assays of the invention, it is possible to screen thousands of different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100-about 1500 different compounds. It is possible to assay many plates per day; assay screens for up to about 6,000, 20,000, 50,000, or more than 100,000 different compounds are possible using the integrated systems of the invention.

The channel of interest, or a cell or membrane comprising the channel of interest can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest (e.g., the taste transduction molecule of interest) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

VII. COMPUTER ASSISTED DRUG DESIGN USING SLO2 OR SLO4

Yet another assay for compounds that modulate the activities of a Slo2 or Slo4 channel involves computer assisted drug design, in which a computer system is used to generate a three-dimensional structure of Slo2 or Slo4 based on the structural information encoded by the amino acid sequence. The input amino acid sequence interacts directly and actively with a pre-established algorithm in a computer program to yield secondary, tertiary, and quaternary structural models of the protein. The models of the protein structure are then examined to identify regions of the structure that have the ability to bind, e.g., ligands or other potassium channel subunits. These regions are then used to identify ligands that bind to the protein or region where Slo2 or Slo4 interacts with other potassium channel subunits.

The three-dimensional structural model of the protein is generated by entering channel protein amino acid sequences of at least 25, 50, 75 or 100 or more amino acid residues or corresponding nucleic acid sequences encoding a Slo2 or Slo4 monomer into the computer system. The amino acid sequence of each of the monomers is selected from the group consisting of SEQ ID NO:2 or 4 and a conservatively modified versions thereof, or an immunogenic portion thereof comprising a conserved region, e.g., the pore loop or the tail domains. The amino acid sequence represents the primary sequence or subsequence of each of the proteins, which encodes the structural information of the protein. At least 25, 50, 75, or 100 residues of the amino acid sequence (or a nucleotide sequence encoding at least about 25, 50, 75 or 100 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the channel protein is then generated by the interaction of the amino acid sequence and the computer system, using software known to those of skill in the art. The resulting three-dimensional computer model can then be saved on a computer readable substrate.

The amino acid sequence represents a primary structure that encodes the information necessary to form the secondary, tertiary and quaternary structure of the monomer and the heteromeric potassium channel protein comprising four monomers. The software looks at certain parameters encoded by the primary sequence to generate the structural model. These parameters are referred to as "energy terms," or anisotropic terms and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of the Slo2 or Slo4 protein to identify ligands that bind to Slo2 or Slo4. Binding affinity between the protein and ligands is determined using energy terms to determine which ligands have an enhanced probability of binding to the protein.

Computer systems are also used to screen for mutations, polymorphic variants, alleles and interspecies homologs of Slo2 or Slo4 genes. Such mutations can be associated with disease states. Once the variants are identified, diagnostic assays can be used to identify patients having such mutated genes associated with disease states. Identification of the mutated Slo2 or Slo4 genes involves receiving input of a first nucleic acid, e.g., SEQ ID NOS:1 or 3, or an amino acid sequence encoding Slo2 or Slo4, e.g., SEQ ID NO:2 or 4, and conservatively modified versions thereof, or an amino acid sequence comprising a conserved region, e.g., the pore loop or the tail domain. The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in Slo2 or Slo4 genes, preferably human Slo2 or Slo4 genes and mutations associated with disease states. The first and second sequences described above can be saved on a computer readable substrate.

Nucleic acids encoding Slo2 or Slo4 monomers can be used with high density oligonucleotide array technology (e.g., GeneChip™) to identify Slo2 or Slo4 homologs, orthologs, alleles, conservatively modified variants, and polymorphic variants in this invention. In the case where the homologs being identified are linked to a known disease, they can be used with GeneChip™ as a diagnostic tool in detecting the disease in a biological sample, see, e.g., Gunthand et al., *AIDS Res. Hum. Retroviruses* 14: 869-876 (1998); Kozal et al., *Nat. Med.* 2:753-759 (1996); Matson et al., *Anal. Biochem.* 224:110-106 (1995); Lockhart et al., *Nat. Biotechnol.* 14:1675-1680 (1996); Gingeras et al., *Genome Res.* 8:435-448 (1998); Hacia et al., *Nucleic Acids Res.* 26:3865-3866 (1998).

VIII. CELLULAR TRANSFECTION AND GENE THERAPY

The present invention provides the nucleic acids of Slo2 or Slo4 for the transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acid for Slo2 or Slo4, under the control of a promoter, then expresses a Slo2 or Slo4 monomer of the present invention, thereby mitigating the effects of absent, partial inactivation, or abnormal expression of the Slo2 or Slo4 gene. The compositions are administered to a patient in an amount sufficient to elicit a therapeutic response in the patient. An amount adequate to accomplish this is defined as "therapeutically effective dose or amount."

Such gene therapy procedures have been used to correct acquired and inherited genetic defects, cancer, and viral infection in a number of contexts. The ability to express artificial genes in humans facilitates the prevention and/or cure of many important human diseases, including many diseases which are not amenable to treatment by other therapies (for a review of gene therapy procedures, see Anderson, *Science* 256:808-813 (1992); Nabel & Felgner, TIBTECH 11:211-217 (1993); Mitani & Caskey, TIBTECH 11:162-166 (1993); Mulligan, *Science* 926-932 (1993); Dillon, TIBTECH 11:167-175 (1993); Miller, *Nature* 357:455-460 (1992); Van Brunt, *Biotechnology* 6(10):1149-1154 (1998); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* (Doerfler & Böhm eds., 1995); and Yu et al., *Gene Therapy* 1:13-26 (1994)).

Delivery of the gene or genetic material into the cell is the first step in gene therapy treatment of disease. A large number of delivery methods are well known to those of skill in the art. Preferably, the nucleic acids are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell.

Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in, e.g., U.S. Pat. No. 5,049,386, U.S. Pat. No. 4,946,787; and U.S. Pat. No. 4,897,355 and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleic acids could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a virus, e.g., a retrovirus, can be altered by incorporating foreign envelope proteins, expanding the potential target population of target cells. Lentiviral vectors are retroviral vector that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), simian immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications where transient expression of the nucleic acid is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994)). Construction of recombinant AAV vectors are described in a number of publications, including U.S. Pat. No. 5,173,414; Tratschin et al., *Mol. Cell. Biol.* 5:3251-3260 (1985); Tratschin et al., *Mol. Cell. Biol.* 4:2072-2081 (1984); Hermonat & Muzyczka, *Proc. Natl. Acad. Sci. U.S.A.* 81:6466-6470 (1984); and Samulski et al., *J. Virol.* 63:03822-3828 (1989).

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

Vectors (e.g., retroviruses, adenoviruses, liposomes, etc.) containing therapeutic nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Administration is by any of the routes normally used for introducing a molecule into ultimate contact with blood or tissue cells. The nucleic acids are administered in any suitable manner, preferably with pharmaceutically acceptable carriers. Suitable methods of administering such nucleic acids are available and well known to those of skill in the art, and, although more than one route can be used to administer a particular composition, a particular route can often provide a more immediate and more effective reaction than another route.

IX. PHARMACEUTICAL COMPOSITIONS AND ADMINISTRATION

Pharmaceutically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present invention (see, e.g., *Remington's Pharmaceutical Sciences,* 17$^{th}$ ed., 1989). Administration can be in any convenient manner, e.g., by injection, oral administration, inhalation, transdermal application, or rectal administration.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of commends can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of conditions owing to diminished or aberrant expression of the Slo channels comprising a Slo2 or Slo4 subunit, the physician evaluates circulating plasma levels of the vector, vector toxicities, progression of the disease, and the production of anti-vector antibodies. In general, the dose equivalent of a naked nucleic acid from a vector is from about 1 µg to 100 µg for a typical 70 kilogram patient, and doses of vectors which include a retroviral particle are calculated to yield an equivalent amount of therapeutic nucleic acid.

For administration, compounds and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

X. KITS

Human Slo2 or Slo4 and their homologs are useful tools for examining expression and regulation of potassium channels. Human Slo2 or Slo4-specific reagents that specifically hybridize to hSlo2 or Slo4 nucleic acid, such as hSlo2 or Slo4 probes and primers, and hSlo2 or Slo4-specific reagents that specifically bind to the hSlo2 or Slo4 protein, e.g., hSlo2 or Slo4 antibodies are used to examine expression and regulation.

Nucleic acid assays for the presence of hSlo2 or Slo4 DNA and RNA in a sample include numerous techniques are known to those skilled in the art, such as Southern analysis, northern analysis, dot blots, RNase protection, S1 analysis, amplification techniques such as PCR and LCR, and in situ hybridization. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques* 4:230-250 (1986); Haase et al., *Methods in Virology*, vol. VII, pp. 189-226 (1984); and *Nucleic Acid Hybridization: A Practical Approach* (Hames et al., eds. 1987). In addition, hSlo2 or Slo4 protein can be detected with the various immunoassay techniques described above. The test sample is typically compared to both a positive control (e.g., a sample expressing recombinant Slo2 or Slo4 monomers) and a negative control.

The present invention also provides for kits for screening modulators of the potassium channels of the invention. Such kits can be prepared from readily available materials and reagents. For example, such kits can comprise any one or more of the following materials: Slo2 or Slo4 monomers, reaction tubes, and instructions for testing the activities of potassium channels containing Slo2 or Slo4. A wide variety of kits and components can be prepared according to the present invention, depending upon the intended user of the kit and the particular needs of the user. For example, the kit can be tailored for in vitro or in vivo assays for measuring the activity of a potassium channel comprising a Slo2 or Slo4 monomer.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following example is provided by way of illustration only and not by way of limitation. Those of skill in the art will readily recognize a variety of noncritical parameters that could be changed or modified to yield essentially similar results.

Example 1

Cloning and Expression of Human Slo2

A. Cloning

A fragment of the human Slo2 sequence was identified in the human EST database at NCBI by BLAST search homology to the amino acid sequence of human Slo1, a large-conductance calcium-activated potassium channel. A single EST of Slo2, R87855, was identified, ordered and completely sequenced. The clone contained approximately 700 bp of sequence with homology to a long C-terminal cytoplasmic domain contained in the Slo1 sequence (Slo1 is over 3 Kb in length). Neither the 5' or 3' ends of the gene were present in this clone, indicating that it represented only a small fragment of the Slo2 gene. The cDNA was named Slo2 because it shared the greatest homology with a *C. elegans* potassium channel that had already been named Slo2. It should be noted, however, that human Slo2 and the *C. elegans* gene are not orthologs.

The 3' end of the human Slo2 gene was cloned using two nested rounds of RACE PCR with human hippocampus cDNA as a template. RACE PCR is a technique in which a gene specific oligo is used in conjunction with an oligo to a non-specific tag present on a pool of cDNAs to amplify the end of the gene from that pool. In the first round, the gene-specific sense primer used was 5'-CACCACGGAGCTCAC-CCACCCTTCC-3' (1) (SEQ ID NO:5). A small aliquot of this reaction was then reamplified with a Slo2 gene-specific sense oligo nested 3' of (1), 5'-CGCGTCTTCAGCATCAG-CATGTTGGAC-3' (2) (SEQ ID NO:6). Both gene specific oligos were derived from the sequence of the R87855 EST clone. Four cDNAs ranging from approximately 600 by to approximately 2 Kb were isolated and sequenced. An approximately 1.8 Kb fragment was sequenced and found to contain the 3' end of the Slo2 coding region as well as 3' UTR sequence.

Several rounds of 5' RACE PCR were used to clone most of the 5' end of human Slo2. First, 2 rounds of nested 5' RACE PCR were used to amplify an approximately 500 by fragment of Slo2 from a human hippocampus cDNA library using Slo2-specific antisense oligos based on the R87855EST sequence. In the first round, the gene specific antisense oligo used was 5'-CTGGTAGAGCAGTGTGTCCAACATGCTG-3' (3) (SEQ ID NO:7). A small aliquot of this reaction was reamplified with a more 5'Slo2 antisense oligo 5'-ACTGCAT-GAAGCGCATGTTGGAAGGGTG-3' (4) (SEQ ID NO:8) to obtain the fragment. This fragment contained significant homology to the *C. elegans* Slo2 gene, but clearly did not represent a 5' complete cDNA.

Two new Slo2 antisense oligos were designed based on the 5' end of this ~500 by fragment.

2 rounds of nested 5' RACE PCR were used to obtain fragments of ~1 Kb in length using these oligos. In the first round, the gene specific antisense oligo used was 5'-CCCAT-TGCCGGCCGTCTCTGCCGAG-3' (5) (SEQ ID NO:9). A small aliquot of this reaction was reamplified with a more 5' Slo2 antisense oligo 5'-CTTGAACCCGTAGGCCTTG-GCGTCTTC-3' (6) (SEQ ID NO:10) to yield the 1 Kb fragments. These fragments encoded an amino acid with over 30% identity to *C. elegans* Slo2, and with a lower level of homology to Slo1. These fragments represented incomplete cDNAs because the fragments are homologous to the middle of the *C. elegans* Slo2 gene, which contains over 1 Kb of coding sequence upstream of the region homologous to these human Slo2 fragments. The 5' PCR was repeated with 2 new human Slo2-specific antisense oligos based on the 5' most sequence obtained from the above 5' RACE PCR fragments. The new oligos used were 5'-CACACCACGTGGTCAG-CAAACTTGACG-3' (7) (SEQ ID NO:11) in the first round and 5'-GCAGTTGGGGGCGAAGTCCTTCACGG-3' (8) (SEQ ID NO:12) in the second round. A fragment of approximately 1.2 Kb was isolated from the second reaction and sequenced. This band was found to contain homology to the 5' region of *C. elegans* Slo2, but contained no obvious start codons. Comparison to a newly cloned rat gene, rat SLACK (Joiner et al., *Nat. Neurosci.* 1:462-9 (1998)), also indicated that the human Slo2 sequence was probably 5' incomplete.

The cDNA cloned by Joiner et al. appeared to be the rat ortholog of human Slo2, sharing over 90% amino acid identity.

All RACE PCR products described above were produced under a relatively standard set of conditions. Denaturations were carried out at 95° C. for 15 seconds, annealing temperatures ranged from 72-60° C. for 15 seconds, and extensions were carried out at 72° C. for 90 seconds to 3 minutes depending on the length of the products. First round RACE reactions consisted of 35-40 cycles of PCR, will nested reamplifications consisted of 20-30 cycles.

A clone containing a 5' incomplete (but otherwise full-length) human Slo2 sequence was constructed using overlap extension PCR and 3 Slo2 fragments amplified from human hippocampus cDNA. A 5' fragment of approximately 1.3 Kb was amplified using the sense oligo 5'-CACCTTCAAG-GAGCGGCTCAAGCTG-3' (9) (SEQ ID NO:13) and the antisense oligo 5'-GACGTGTGCACCAGCAGGGTGAT-GAG-3' (10) SEQ ID NO:14). The middle of the Slo2 sequence was amplified as a 1.55 Kb fragment with the oligos (sense) 5'-GTTTCACGTCAAGTTTGCTGACCACG-3' (11) (SEQ ID NO:15) and (antisense) 5'-CCGTACGTGCG-GATCCACAGGTCG-3' (12) (SEQ ID NO:16). The 3' end of the Slo2 coding sequence was amplified with the sense oligo 5'-CGTGAAGGACTACATGATCACCATC-3' (13) (SEQ ID NO:17) and the antisense oligo 5'-CAGGGTCTAGATTA-GAGCTGTGTCTCGTCGCGAGTCTC-3' (14) (SEQ ID NO:18) to produce a fragment of 800 bp. The latter oligo includes the predicted Slo2 stop codon and 3' end of Slo2 coding (in bold), plus an XbaI site for subcloning on the 5' end. It should be noted that only the bold sequence corresponding to Slo2 is used to amplify Slo2. These fragments were assembled into a single fragment using 2 rounds of standard overlap extension PCR. First, the 5' and middle fragments were mixed and amplified with oligos 9 and 12 to produce a fragment of approximately 2.8 Kb. Similarly, the middle and 3' end fragments were mixed and amplified with oligos 11 and 14 to produce a fragment of approximately 2.3 Kb. These two larger fragments were then mixed and amplified with oligos 9 and 14 to produce a fragment of 3.5 Kb containing all known human Slo2 sequence. This fragment was cloned into a plasmid vector and multiple clones were sequenced to determine a final human Slo2 sequence for this region. The conditions used to amplify the coding region of Slo2 were similar to those described above for the Slo2 RACE reactions. One notable exception is that longer extension times (4 minutes) were allowed during the overlap reactions because of the large size of the desired fragments.

A potential 5' end for human Slo2 was identified by BLAST searching the rat SLACK sequence against publicly available human genomic DNA sequence. An exon homologous to the DNA sequence encoding amino acids 1-52 of rat Slack was identified. Based on homology to Rat SLACK, this exon contained the 5' end of human Slo2 coding sequence. A complete putative human Slo2 coding sequence was constructed using the sequence of the 3.5 Kb construct described herein, the 5' end exon, and two other exons identified in the BLAST search. BLAST analysis of this complete coding sequence vs. the human Slo2 genomic sequence shows that the hSlo2 coding sequence is divided into at least 30 exons. This cDNA sequence could not be predicted from genomic DNA, without the cloned cDNA.

The 5' end of Slo2 was amplified from human brain cDNA using an overlap extension PCR screen. A fragment containing the start codon and first 200 bp of Slo2 was amplified using the sense oligo 5'-CCACCATGGCGCGGGC-CAAGCT-3' (15) (SEQ ID NO:19) and the antisense oligo 5'-GAGACAGGGAGGAGTCCAGGCTGAA-3' (16) (SEQ ID NO:20). Only the bold bases in 15 match Slo2 and are used for amplification of Slo2; the 5' bases add a Kozak consensus sequence and are included only for expression vector construction. A second fragment of approximately 400 by that overlapped the first fragment and a unique Hind III restriction site in the 3.5 Kb Slo2 clone was amplified using the oligos 5'-CGTGGGCCAGAGGCTTCCTGTAGAA-3' (17) (SEQ ID NO:21) and 5'-GCTCCCAGATGTTGCCTTTG-TAGCTG-3' (18) (SEQ ID NO:22). These two fragments were mixed and amplified with oligos 15 and 18 to produce an approximately 550 by fragment containing both the initiator methionine of Slo2 and the unique Slo2 Hind III site. This fragment was cloned into a standard plasmid and 3 clones were sequenced. Each clone was identical to the consensus human Slo2 derived from our cDNA and genomic information. A full length Slo2 coding region was then assembled by joining the 5' end fragment and 3.5 Kb Slo2 fragment at their common Hind III restriction site by standard DNA cloning methods.

Recently, a large but partial human Slo2 cDNA was deposited in the NCBI database (KIA1422, accession number AB037843). This clone differs from the complete human Slo2 clone described above in several key ways (see FIG. 1). Most importantly, it is incomplete on the 3' end. DNA encoding 127 amino acids at the carboxy terminus of human Slo2 is missing from KIAA1422. Additionally, KIAA1422 has an alternative 5' end. Because the KIAA1422 reading frame remains open at the 5' end, it is unclear whether the KIAA1422 cDNA represents a clone with a complete alternative 5' end (with the protein starting at one of the internal methionine codons), or whether it represents a 5' incomplete clone. Finally, KIAA1422 contains a 2 amino acid insertion (GT) at the equivalent position of amino acid 650 in the hSlo2 sequence.

The numbered oligonucleotides listed above can be used in various combinations to amplify sections of the hSlo2 cDNA from an appropriate template, such as human brain cDNA, using the conditions described above. Oligos 14-17 are not contained in the KIAA1422 sequence and oligo pairs including at least one of these oligos can be used to amplify fragments that could not be derived from the KIAA1422 sequence. Oligo 17 can be paired with 18, 8, 7, 6, 5, 4, 3 and 14 to produce fragments of approximately 415 bp, 1.25 Kb, 1.3 Kb, 2.19 Kb, 2.23 Kb, 2.59 Kb, 2.74 Kb and 3.58 Kb, respectively. Oligo 15 can be substituted for 17 in the above combinations to produce fragments that are approximately 150 by longer than those listed above. Additionally, oligo 14 can be paired with 9, 11, 1, 2 and 13 to produce fragments of approximately 3.49 Kb, 2.29 Kb, 1.03 Kb, 880 by and 830 bp, respectively. None of the oligo pairs listed above will amplify KIAA1422. If at least one of these amplifications can be obtained from a gene, and the sequence of the fragment is substantially identical to that of human Slo2, then the sequence should be considered a species of human Slo2. Other notable pairs that would amplify both KIAA1422 and human Slo2 are 9+10 and 11+12, which were used in the production of the 3.5 Kb 5' incomplete human Slo2 clone.

B. mRNA Expression

A northern blot and mRNA dot blot probed with a $^{32}$P-labeled PCR fragment produced with oligos 13 and 14 are shown in FIG. 3. On the northern blot, prominent band of approximately 5 Kb is seen in brain, with a less intense band visible at roughly 6 Kb. Similar bands are seen in skeletal muscle, albeit at a lower intensity. Faint signals are seen in heart and spleen. The mRNA dot blot shows widespread expression of human Slo2 in the central nervous system.

Expression is highest in the cerebellum, cerebral cortex, occipital lobe, temporal lobe, putamen and nucleus accumbens. Significant levels of expression were also found in the fetal brain, amygdala, caudate nucleus, frontal lobe, hippocampus, substantia nigra and thalamus. In addition to the peripheral tissues identified as expressing Slo2 on the northern blot, expression significant levels of expression were found in ovary, placenta, and fetal spleen.

C. *Xenopus* Expression

Functional expression of human Slo2 was examined in *Xenopus* oocytes. Slo2 was cloned into the pOX expression vector and run-off cRNA transcripts were prepared. These transcripts were injected in mature stage 4 *Xenopus* oocytes and examined under whole cell two-electrode voltage clamp after 24-48 hours. Oocyte expression procedures were performed according to Jegla & Salkoff, *J. Neurosci* 17(1):32-44 (1996)).

Figure 5A:
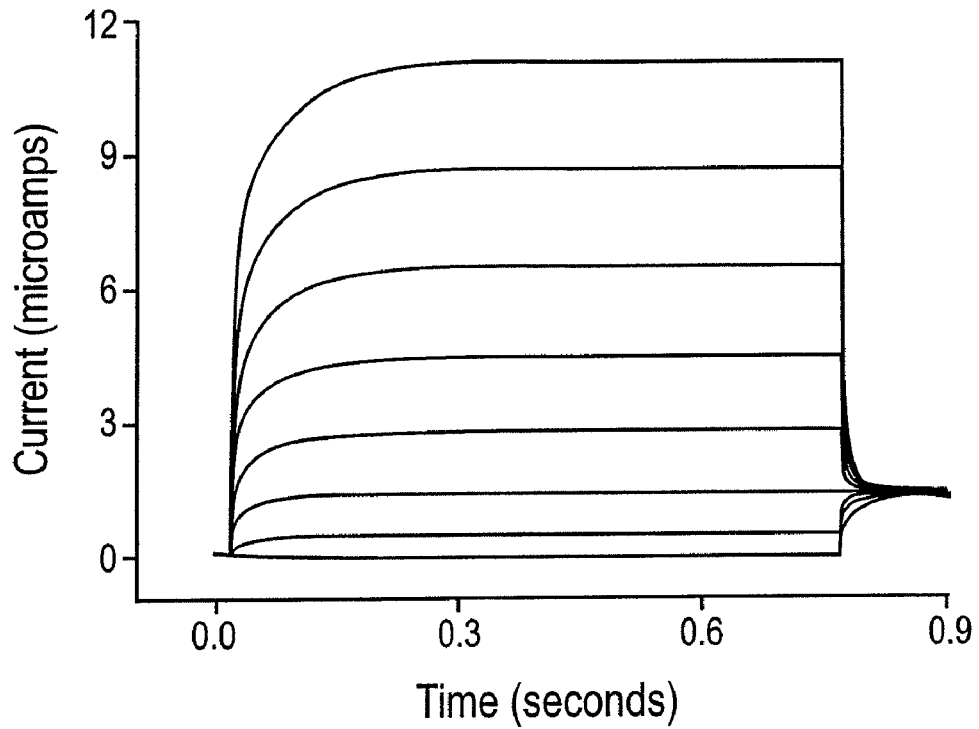
FIG. 5. Functional expression of human Slo2 in *Xenopus* oocytes. (A) Slo2 currents elicited by depolarizing voltage steps from a holding potential of −120 mV up to +40 mV. Steps were taken in 20 mV increments and tail currents were measured at −60 mV. Note that Slo2 current is clearly seen at voltages as low as −80 mV. Activation at −100 mV may be obscured because this in near the potassium equilibrium potential. (B) Currents elicited from an oocyte expressing Slo2 with 3 second voltage ramps ranging from −160 mV to +80 mV. Ramps were run with either 2 mM external potassium (1) or 50 mM external potassium (2). Note the large positive shift in reversal potential of the current at 50 mM potassium (right arrow). Also note the large inward current in 50 mM potassium that is seen at the resting voltage of −90 mV (left arrow). This indicates significant activation of Slo2 at −90 mV. It is unmasked by 50 mM potassium which shifts the reversal potential away from −90 mV, providing a large driving force for potassium entry.
Figure 5B:
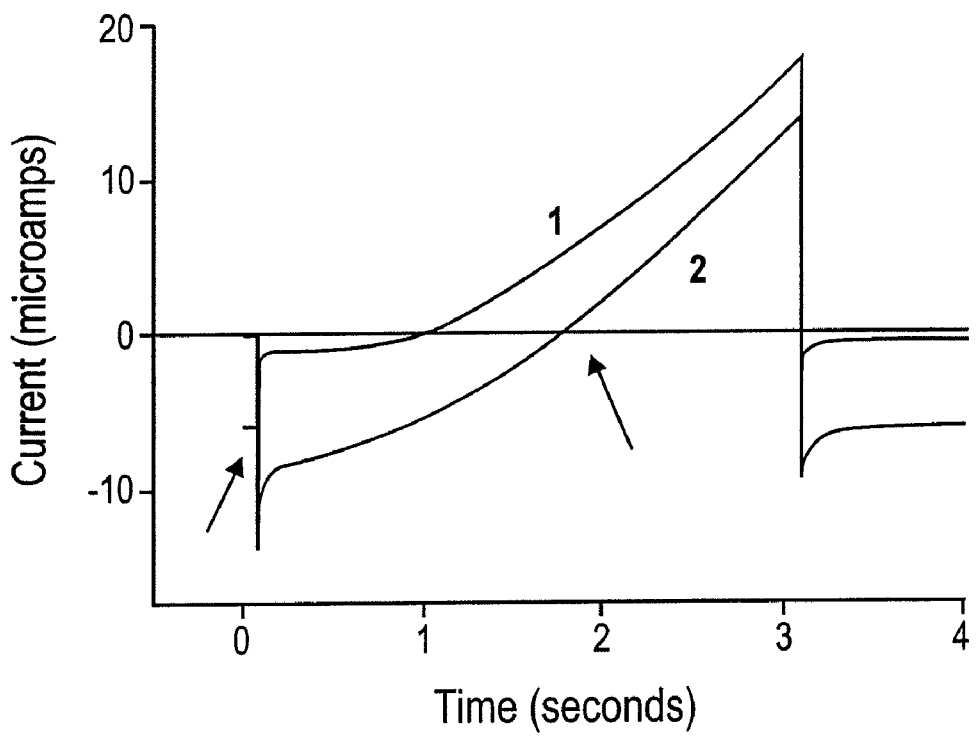

FIG. 5*a* shows a series of currents recorded from an oocyte expressing human Slo2. A large, outwardly rectifying current is seen in voltage steps above −100 mV. No similar current was seen in uninjected control oocytes. The reversal potential of the human Slo2 current shifted with changes in external potassium concentration (FIG. 5*b*). In the example shown, the reversal potential of the Slo2 current shifts almost +70 mV in response to an increase in external potassium concentration from 2 mM to 50 mM. This large shift is almost as much as that predicted for a channel that is perfectly potassium selective, and indicates that Slo2 channels are highly selective for potassium over other cations. These results also indicate that Slo2 is voltage gated.

Example 2

Cloning and Expression of Slo4

A. Cloning

Partial human Slo4 sequences were originally identified with TBLASTN searches of 3 databases with the rat SLACK sequence and partial human Slo2 sequences: A proprietary database, the public EST database at NCBI, and the public Genome Survey Sequence Database at NCBI. The proprietary clone 5035170 contained a short stretch of Slo4 coding sequence with amino acid 60% identity to rat SLACK amino acids 646-730. The entire clone had an insert of less than 700 bp. It was sequenced in its entirety and determined that most of the insert probably represented intronic sequence. The two Genome survey sequences (GSS), AQ701228 and AQ892600 contained homology Rat SLACK just 5' and 3' to the proprietary clone, respectively. Finally, a public EST clone (AI791929) was identified that had homology to the 3' end of the RAT SLACK coding sequence and appeared to contain a stop codon for the Slo4 open reading frame. These non-overlapping sequences were confirmed to have come from the same gene by amplifying an approximately 1.5 Kb fragment with a sense oligo based on the 5' most sequence (AQ701228), 5'-GGCGTCTGCTTGATTGGTGTTAGGA-3' (19) (SEQ ID NO:23), and an antisense oligo overlapping the stop codon in the EST sequence, 5'-TTTATCTAGAATCAAAGTTGAGTTTCCTCCCGAG-3' (20) (SEQ ID NO:24). This amplified clone contained sequence identical to all four of the clones identified by BLAST searches. It also contained a high degree of homology to human Slo2 and rat SLACK across its entire length.

Two partial genomic sequences of Slo4 (AL139137.1 and AL138931.1) were then discovered using TBLASTN searches of the NCBI High Throughput Genomic Sequence Database (HTGS) with the complete human Slo2 sequence described above. AL138931.1 contained 10 exons with homology to Slo2, with 3 of those exons containing sequence more 5' than that which we had previously identified. The 5' most exon contained homology to amino acids 449-484 of the human Slo2 sequence. To clone the 5' end of the Slo4 coding sequence, antisense oligos were designed based on this new sequence for use in 5' RACE PCR. A single round of RACE PCR with the Slo4-specific antisense oligo 5'-CCCGGAGCATCTACCGTACATCTTC-3' (21) (SEQ ID NO:25) produced a fragment of approximately 800 by from human brain cDNA. This fragment extended the Slo4 coding sequence by almost 500 by into a region highly homologous to the pore-loop motifs of Slo potassium channels.

The 5' end of the Slo4 coding sequence was cloned with 2 nested rounds of 5' RACE PCR using Slo4-specific antisense oligos based on the new sequence obtained in the first 5' RACE attempt. The Slo4-specific oligos used were 5'-CCAGCTGTTCAAACTGTATGGGTAG-3' (22) (SEQ ID NO:26) and 5'-GCTTGGAGGACCATGTTTCAGGAGT-3' (23) (SEQ ID NO:27) in the first and second rounds, respectively. Conditions for these amplifications and the first Slo4 5' RACE attempt were similar to those described above for Slo2. An approximately 900 by fragment was isolated from the 2nd reaction and was determined to contain the 5' end of the Slo4 coding sequence. The fragment contains a long open reading frame with substantial homology to the 5' coding region of human Slo2. A stop codon ends the open reading frame immediately upstream of a methionine codon, indicating that this is the initiator methionine of Slo4.

The entire Slo4 coding sequence was amplified in a single fragment using a sense oligo overlapping the initiator methionine codon, 5'-ATCCCAATTGCCGCCATGGTTGATTTGGAGAGCGAAGTG-3' (24) (SEQ ID NO:28) and the antisense oligo overlapping the stop codon, oligo #20. Only the bases listed in bold type in oligos 20 and 24 match the Slo4 DNA sequence. In oligo 20, the additional bases at the 5' end add an XbaI restriction site to assist subcloning. In oligo 24 the additional bases at the 5' end add a MunI site for subcloning and a Kozak consensus sequence to boost translation initiation at the Slo4 methionine codon. Only the areas given in bold type are used for the amplification of Slo4; the other bases need not be present to obtain amplification.

Two additional Slo4-specific sense oligos and one Slo4-specific antisense oligo can be used to amplify Slo4:

```
Sense
                                         (SEQ ID NO: 29)
5'-CAATTTTGAGAGCATGGGCTGTGAAAG-3' (25)

(SEQ ID NO: 30)
5'-GACTTATGGATCAGAACTTATGCCCAG-3' (26)

Antisense
                                         (SEQ ID NO: 31)
5'-CATCTGGTGTAGTTTCATCTTCTGATTGG-3' (27).
```

These oligos can be used in combination with the other Slo4 oligos listed above to amplify a variety of Slo4 fragments from an appropriate cDNA source such as human brain. 24 can be used with 23, 22, 21, 27 or 20 to produce fragments of approximately 780 bp, 830 bp, 1.46 Kb, 1.98 Kb and 3.4 Kb, respectively. 25 can be used with 21, 27 or 20 to produce bands of around 250 bp, 780 by and 2.2 Kb, respectively. 19 can be used with 27 or 20 to produce fragments of approximately 420 by and 1.85 Kb. Finally, 26 can be used with 20 to produce a fragment of around 600 bp. If at least one of these amplifications can be obtained from a gene, and the sequence of the fragment is substantially identical to that of human Slo4, then the sequence should be considered a species of human Slo4.

B. mRNA Expression

Figure 7A:
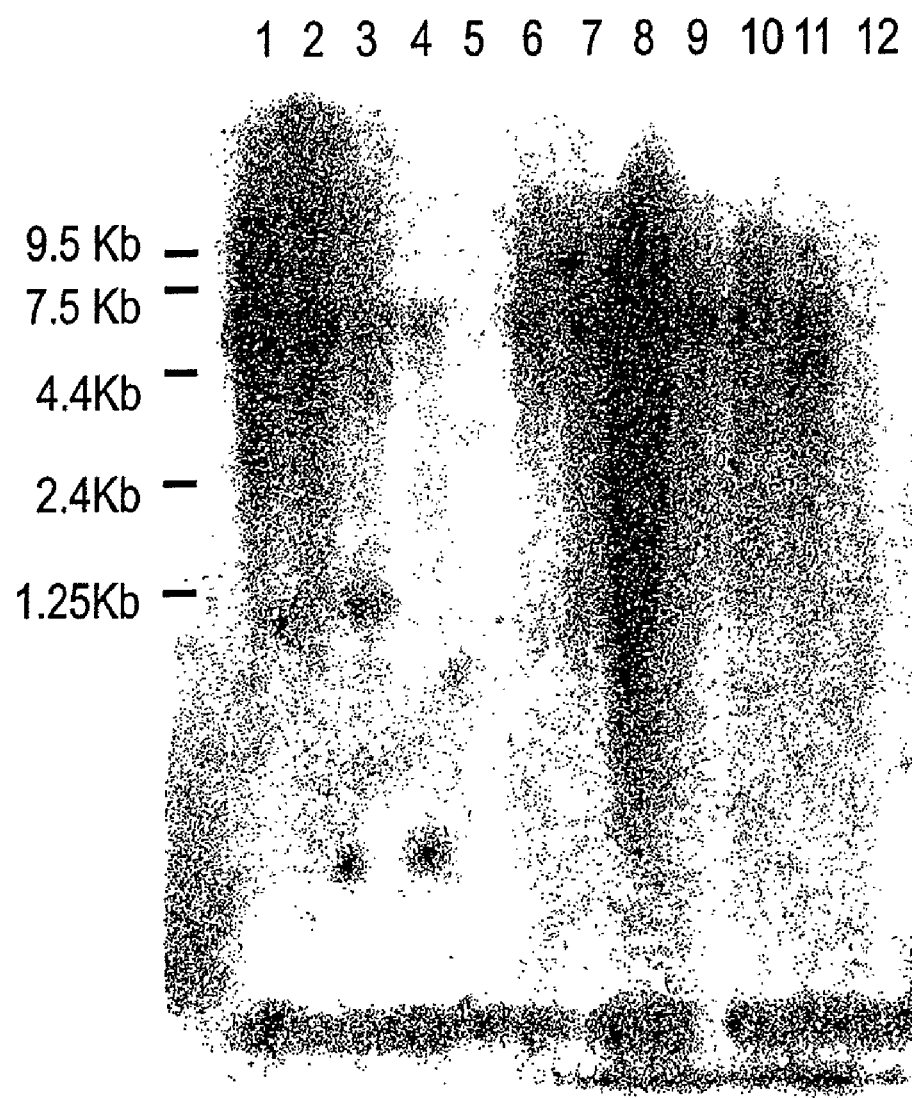
FIG. 7. (A) Human northern blot hybridized with a $^{32}$P-labeled Slo4 cDNA probe. Marks at the left margin indicate molecular weight in kilobases (Kb). Lane numbers are given at the top. The following is a list of the tissues in these lanes: 1) whole brain, 2) heart, 3) skeletal muscle, 4) colon, 5) thymus, 6) spleen, 7) kidney, 8) liver, 9) small intestine, 10) placenta, 11) lung, 12) peripheral blood leukocytes. A transcript of approximately 5.5 Kb is labeled in most of these tissues. Expression is highest in the liver, with high level expression also being found in the brain and heart. Lower levels of expression are detected in skeletal muscle, colon, spleen, kidney, small intestine, placenta and lung. Larger transcripts of approximately 9 Kb and 13 Kb are seen in brain and heart. These may represent alternative transcripts or incompletely processed transcripts. A 4.5 Kb transcript is seen in lung, and may represent an alternative transcript; it is long enough to encode a complete Slo4 protein. (B) mRNA dot blot hybridized with the same probe as in (A). The highest levels of expression are seen in liver, fetal brain, fetal kidney and fetal liver. High levels of expression are also seen in testis, fetal lung, most brain regions, the atrium, the GI track, lung, placenta and bladder. Expression is detectable in many other tissues on the blot. Based on comparison with the northern results in (A), these low signals are likely to represent Slo4 expression and not background non-specific hybridization.
Figure 7B:
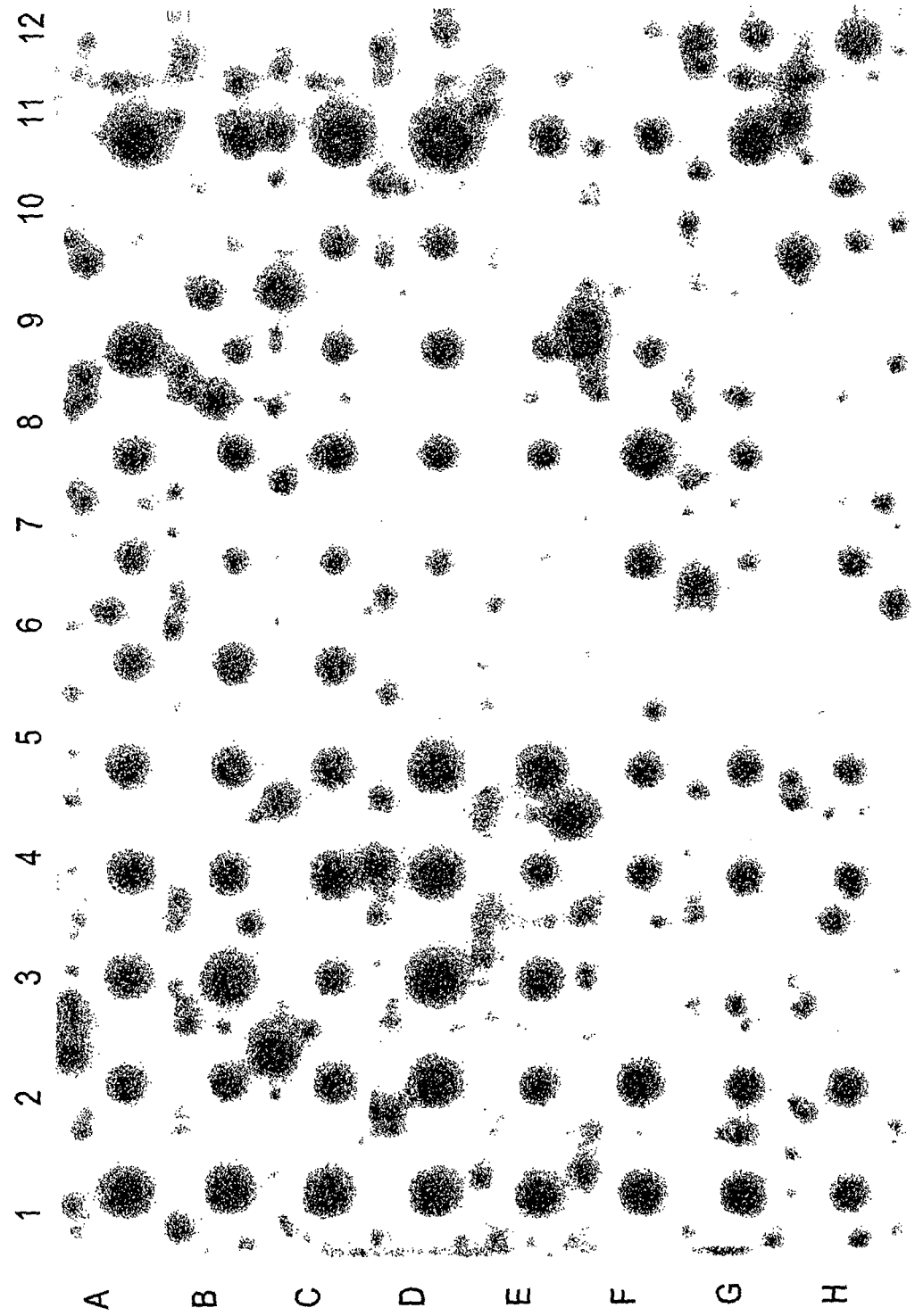

A human northern blot and dot blot hybridized with a $^{32}$P-labeled Slo4 cDNA probe are shown in FIG. 7. A transcript of approximately 5.5 Kb is labeled in most of the tissues on the northern blot. Expression is highest in the liver, with high level expression also being found in the brain and heart. Lower levels of expression are detected in skeletal muscle, colon, spleen, kidney, small intestine, placenta and lung. Larger transcripts of approximately 9 Kb and 13 Kb are seen in brain and heart. These may represent alternative transcripts or incompletely processed transcripts. A 4.5 Kb transcript is seen in lung, and may represent an alternative transcript; it is long enough to encode a complete Slo4 protein. In the dot blot, the highest levels of expression are seen in liver, fetal brain, fetal kidney and fetal liver. High levels of expression are also seen in testis, fetal lung, most brain regions, the atrium, the GI track, lung, placenta and bladder. Expression is detectable in many other tissues on the blot. Based on comparison with the northern results in (A), these low signals are likely to represent Slo4 expression and not background non-specific hybridization.

C. *Xenopus* Expression

Functional expression of human Slo4 was examined in *Xenopus* oocytes. Slo4 was cloned into the pOX expression vector and run-off cRNA transcripts were prepared. These transcripts were injected in mature stage 4 *Xenopus* oocytes and examined under whole cell two-electrode voltage clamp after 24-48 hours. Oocyte expression procedures were performed according to Jegla & Salkoff, *J. Neurosci* 17(1):32-44 (1996)).

Figure 6A:
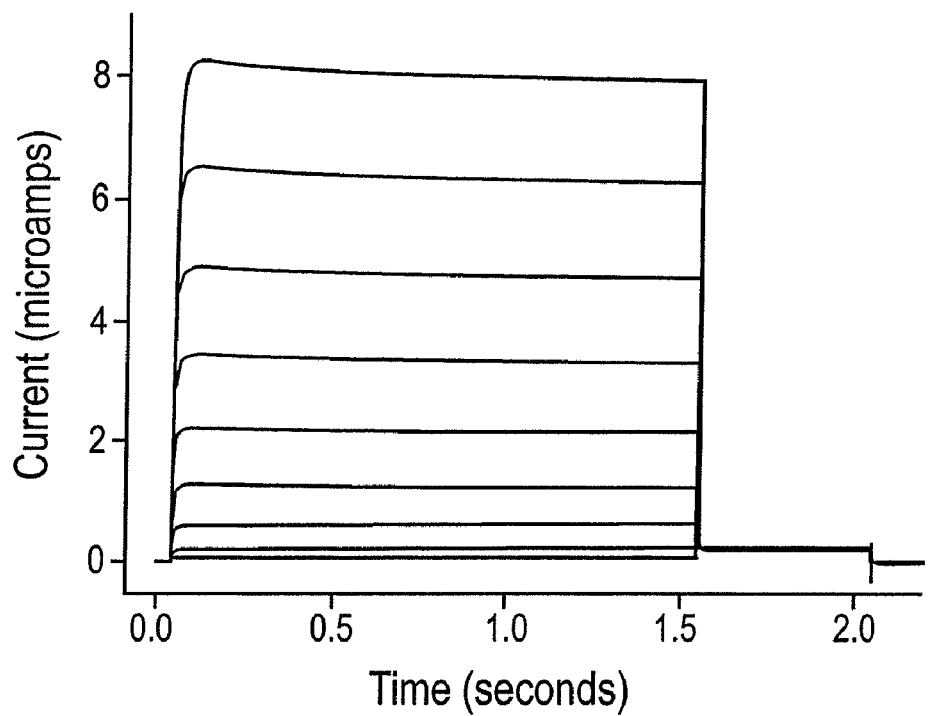
FIG. 6. Functional expression of human Slo4 in *Xenopus* oocytes. (A) Slo4 currents elicited by depolarizing voltage steps from −80 mV up to +80 mV. Steps were taken in 20 mV increments from a holding potential of −100 mV, and tail currents were measured at −60 mV. The Slo4 current is clearly seen at −60 mV, and some Slo4 current is present even at −80 mV. (B) Currents elicited from an oocyte expressing Slo4 with 3 second voltage ramps ranging from −160 mV to +80 mV. Ramps were run with either 2 mM external potassium (1) or 20 mM external potassium (2). Note the large positive shift in reversal potential of the current in 20 mM potassium (right arrow). Also note that some inward current in 20 mM potassium is seen at the resting voltage of −90 mV (left arrow). This indicates activation of Slo4 at −90 mV.
Figure 6B:
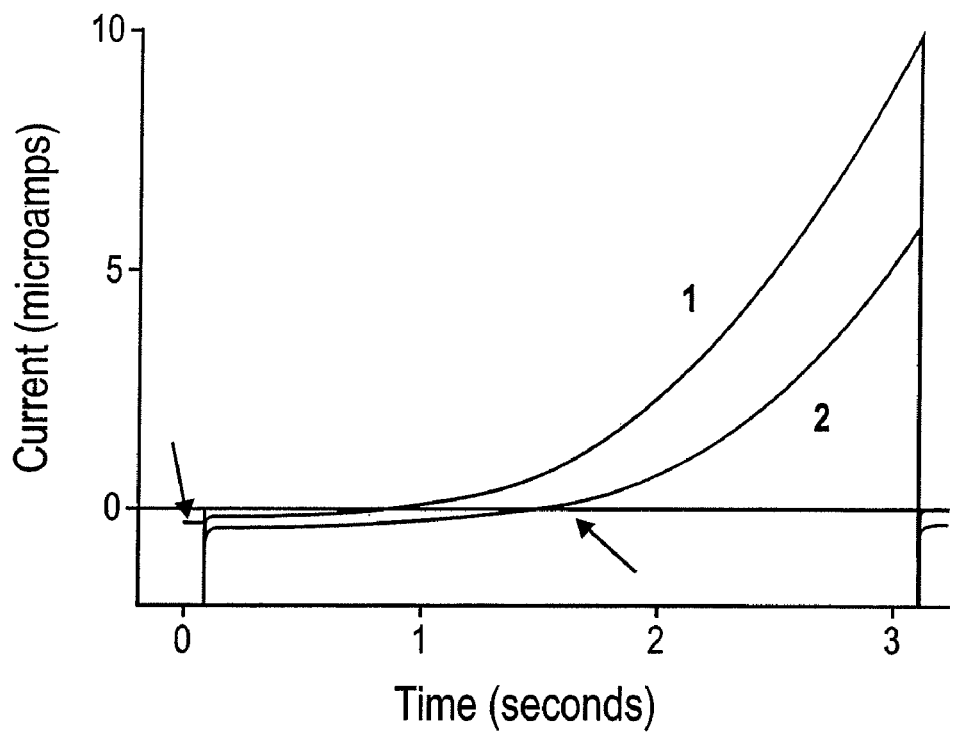

FIG. 6 shows a similar set of experiments conducted with human Slo4. As observed for Slo2, large, outwardly rectifying potassium currents are seen with depolarizing voltage steps. The reversal potential for Slo4 was also highly sensitive to changes in external potassium concentration. As shown in FIG. 6b, change in external potassium concentration from 2 mM to 20 mM caused the Slo4 current reversal potential to shift over +45 mV. This change is almost at great at the +48 mV shift that would be expected for a perfectly potassium selective channel, indicating that Slo4 is very highly potassium selective over other cations, as is Slo2. These results also indicate that Slo4 is voltage gated.

Sequence Listing

SEQ ID NO: 1-Human Slo2 nucleotide sequence

ATGGCGCGGGCCAAGCTGCCGCGCTCGCCGTCCGAGGGCAAGGCGGGC

CCGGGGGGCGCCCCAGCCGGCGCCGCAGCCCCGAGGAGCCTCACGGG

CTCAGCCCGCTGCTGCCGGCCCGCGGCGGGGGCTCCGTGGGCAGCGAC

GTGGGCCAGAGGCTTCCTGTAGAAGATTTCAGCCTGGACTCCTCCCTG

TCTCAGGTCCAGGTGGAGTTCTACGTCAACGAGAACACCTTCAAGGAG

CGGCTCAAGCTGTTCTTCATCAAAAACCAAAGATCGAGCCTGAGGATC

CGGCTGTTCAACTTCTCCCTGAAGCTGCTCACCTGCCTGCTCTACATT

GTGCGCGTCCTGCTCGATGACCCGGCCCTGGGCATCGGATGCTGGGGC

TGCCCAAAGCAGAACTACTCCTTCAATGACTCGTCCTCCGAGATCAAC

TGGGCTCCTATTCTGTGGGTGGAGAGAAAGATGACACTGTGGGCGATC

CAGGTCATCGTGGCCATAATAAGCTTCCTGGAGACGATGCTTCTCATC

TACCTCAGCTACAAAGGCAACATCTGGGAGCAGATCTTCCGCGTGTCC

TTCGTCCTGGAGATGATCAACACTCTGCCCTTCATCATCACGATCTTC

TGGCCGCCGCTGCGGAACCTGTTCATCCCCGTCTTTCTGAACTGCTGG

CTGGCCAAGCACGCGCTGGAAAACATGATTAATGACTTCCACCGTGCC

ATCCTGCGGACACAGTCAGCCATGTTCAACCAGGTCCTCATCCTCTTC

TGCACCCTGCTGTGCCTCGTTTTCACGGGGACCTGCGGCATCCAGCAC

CTGGAGCGGGCGGGCGAGAACCTGTCCCTCCTGACCTCCTTCTACTTC

TGCATCGTCACCTTCTCCACCGTGGGCTACGGTGACGTCACGCCCAAG

ATCTGGCCATCGCAGCTGCTGGTGGTCATCATGATCTGCGTGGCCCTC

GTGGTGCTCCCACTGCAGTTCGAGGAGCTCGTCTACCTCTGGATGGAG

CGGCAGAAGTCAGGGGGCAACTACAGCCGCCACCGTGCGCAGACGGAG

AAGCACGTGGTCCTGTGTGTCAGCTCCCTCAAGATCGACCTTCTCATG

GACTTCCTGAACGAGTTCTACGCCCACCCCCGGCTCCAGGACTATTAC

GTGGTCATCCTGTGCCCCACGGAGATGGATGTCCAGGTGCGCAGAGTC

CTGCAGATCCCTCTGTGGTCCCAGCGGGTCATCTACCTCCAGGGCTCT

GCACTCAAAGACCAGGACCTCATGCGAGCCAAGATGGACAATGGGGAG

GCCTGCTTCATCCTCAGCAGCAGGAACGAGGTGGACCGCACGGCTGCA

GACCACCAGACCATCCTGCGCGCCTGGGCCGTGAAGGACTTCGCCCCC

AACTGCCCCCTCTACGTCCAGATCCTCAAACCTGAAAACAAGTTTCAC

GTCAAGTTTGCTGACCACGTGGTGTGTGAGGAGGAGTGCAAGTACGCC

ATGCTGGCGCTGAACTGCATCTGCCCGGCGACCTCCACCCTCATCACC

CTGCTGGTGCACACGTCCCGCGGCCAGGAGGGACAGGAGTCTCCGGAG

CAGTGGCAGCGCATGTATGGGCGCTGCTCCGGCAACGAGGTGTACCAC

ATCCGCATGGGTGACAGCAAGTTCTTCCGCGAGTACGAGGGCAAGAGC

TTCACCTACGCGGCCTTCCACGCCCACAAGAAGTATGGCGTGTGCCTC

ATCGGGCTGAAGCGGGAGGACAACAAGAGCATCCTGCTGAACCCGGGG

CCCCGGCACATCCTGGCCGCCTCTGACACCTGCTTCTACATCAACATC

ACCAAGGAGGAGAACTCGGCCTTCATCTTCAAGCAGGAGGAGAAGCGG

AAGAAGAGGGCCTTCTCGGGGCAGGGGCTGCACGAGGGTCCGGCCCGC

CTGCCCGTGCACAGCATCATCGCCTCCATGGTGGCCATGGACCTGCAG

GGCACAGAGCACCGGCCTACGCAGAGCGGCGGTGGGGCGGGGCAGC

AAGCTGGCACTGCCCACGGAGAACGGCTCGGGCAGCCGGCGGCCCAGC

ATCGCGCCCGTCCTGGAACTGGCCGACAGCTCAGCCCTGCTGCCCTGC

GACCTGCTGAGCGACCAGTCGGAGGATGAGGTGACGCCGTCGGACGAC

GAGGGGCTCTCCGTGGTAGAGTATGTGAAGGGCTACCCTCCCAACTCG

CCCTACATCGTCAGCTCCCAACCCTGTGCCACCTCCTGCCTGTGAAA

GCCCCCTTCTGCTGCCTGCGGCTGGACAAGGGCTGCAAGCACAACAGC

TATGAAGACGCCAAGGCCTACGGGTTCAAGAACAAGCTGATCATCGTC

-continued

```
TCGGCAGAGACGGCCGGCAATGGGCTGTACAACTTCATCGTGCCACTG
CGGGCCTACTACAGATCCCGCAAGGAGCTGAACCCCATCGTGCTGCTG
CTGGACAACAAGCCCGACCACCACTTCCTGGAAGCCATCTGCTGCTTC
CCCATGGTCTACTACATGGAGGGCTCTGTGGACAACCTGGACAGCCTG
CTGCAGTGTGGCATCATCTATGCGGACAACCTGGTGGTGGTGGACAAG
GAGAGCACCATGAGCGCCGAGGAGGACTACATGGCGGACGCCAAGACC
ATCGTCAACGTGCAGACCATGTTCCGGCTCTTCCCCAGCCTCAGCATC
ACCACGGAGCTCACCCACCCTTCCAACATGCGCTTCATGCAGTTCCGC
GCCAAGGACAGCTACTCTCTGGCTCTTTCCAAACTAGAAAAGAGGGAG
CGAGAGAATGGCTCCAACCTGGCCTTCATGTTCCGCCTGCCGTTCGCC
GCCGGCCGCGTCTTCAGCATCAGCATGTTGGACACACTGCTCTACCAG
TCCTTCGTGAAGGACTACATGATCACCATCACCCGGCTGCTGCTGGGC
CTGGACACCACGCCGGGCTCGGGGTACCTCTGTGCCATGAAAATCACC
GAGGGCGACCTGTGGATCCGCACGTACGGCCGCCTCTTCCAGAAGCTC
TGCTCCTCCAGCGCCGAGATCCCCATTGGCATCTACCGGACAGAGAGC
CACGTCTTCTCCACCTCGGAGCCCCACGACCTCAGAGCCCAGTCCCAG
ATCTCGGTGAACGTGGAGGACTGTGAGGACACACGGGAAGTGAAGGGG
CCCTGGGGCTCCCGCGCTGGCACCGGAGGCAGCTCCCAGGGCCGCCAC
ACGGGCGGCGGTGACCCCGCAGAGCACCCACTGCTACGGCGCAAGAGC
CTGCAGTGGGCCCGGAGGCTGAGCCGCAAGGCGCCCAAGCAGGCAGGC
CGGGCGGCGGCCGCGGAGTGGATCAGCCAGCAGCGCCTCAGCCTGTAC
CGGCGCTCTGAGCGCCAGGAGCTCTCCGAGCTGGTGAAGAACGCATG
AAGCACCTGGGGCTGCCCACCACCGGCTACGAGGACGTAGCAAATTTA
ACAGCCAGTGATGTCATGAATCGGGTAAACCTGGGATATTTGCAAGAC
GAGATGAACGACCACCAGAACACCCTCTCCTACGTCCTCATCAACCCT
CCGCCCGACACGAGGCTGGAGCCCAGTGACATTGTCTATCTCATCCGC
TCCGACCCCCTGGCTCACGTGGCCAGCAGCTCCCAGAGCCGGAAGAGC
AGCTGCAGCCACAAGCTGTCGTCCTGCAACCCCGAGACTCGCGACGAG
ACACAGCTCTAA
```

SEQ ID NO: 2-Human Slo2 amino acid sequence
```
MARAKLPRSPSEGKAGPGGAPAGAAAPEEPHGLSPLLPARGGGSVGSD
VGQRLPVEDFSLDSSLSQVQVEFYVNENTFKERLKLFFIKNQRSSLRI
RLFNFSLKLLTCLLYIVRVLLDDPALGIGCWGCPKQNYSFNDSSSEIN
WAPILWVERKMTLWAIQVIVAIISFLETMLLIYLSYKGNIWEQIFRVS
FVLEMINTLPFIITIFWPPLRNLFIPVFLNCWLAKHALENMINDFHRA
ILRTQSAMFNQVLILFCTLLCLVFTGTCGIQHLERAGENLSLLTSFYF
CIVTFSTVGYGDVTPKIWPSQLLVVIMICVALVVLPLQFEELVYLWME
RQKSGGNYSRHRAQTEKHVVLCVSSLKIDLLMDFLNEFYAHPRLQDYY
VVILCPTEMDVQVRRVLQIPLWSQRVIYLQGSALKDQDLMRAKMDNGE
ACFILSSRNEVDRTAADHQTILRAWAVKDFAPNCPLYVQILKPENKFH
VKFADHVVCEEECKYAMLALNCICPATSTLITLLVHTSRGQEGQESPE
QWQRMYGRCSGNEVYHIRMGDSKFFREYEGKSFTYAAFHAHKKYGVCL
IGLKREDNKSILLNPGPRHILAASDTCFYINITKEENSAFIFKQEEKR
KKRAFSGQGLHEGPARLPVHSIIASMVAMDLQGTEHRPTQSGGGGGS
KLALPTENGSGSRRPSIAPVLELADSSALLPCDLLSDQSEDEVTPSDD
EGLSVVEYVKGYPPNSPYIVSSPTLCHLLPVKAPFCCLRLDKGCKHNS
YEDAKAYGFKNKLIIVSAETAGNGLYNFIVPLRAYYRSRKELNPIVLL
LDNKPDHHFLEAICCFPMVYYMEGSVDNLDSLLQCGIIYADNLVVVDK
ESTMSAEEDYMADAKTIVNVQTMFRLFPSLSITTELTHPSNMRFMQFR
AKDSYSLALSKLEKRERENGSNLAFMFRLPFAAGRVFSISMLDTLLYQ
SFVKDYMITITRLLLGLDTTPGSGYLCAMKITEGDLWIRTYGRLFQKL
CSSSAEIPIGIYRTESHVFSTSEPHDLRAQSQISVNVEDCEDTREVKG
PWGSRAGTGGSSQGRHTGGGDPAEHPLLRRKSLQWARRLSRKAPKQAG
RAAAAEWISQQRLSLYRRSERQELSELVKNRMKHLGLPTTGYEDVANL
TASDVMNRVNLGYLQDEMNDHQNTLSYVLINPPPDTRLEPSDIVYLIR
SDPLAHVASSSQSRKSSCSHKLSSCNPETRDETQL
```

SEQ ID NO: 3-Human Slo4 nucleotide sequence
```
ATGGTTGATTTGGAGAGCGAAGTGCCCCCTCTGCCTCCCAGGTACAGG
TTTCGAGATTTGCTGCTAGGGGACCAAGGATGGCAAAACGACGACAGG
GTACAAGTTGAATTCTATATGAATGAAAATACATTTAAAGAAAGACTA
AAATTATTTTTCATAAAAAACCAGAGATCAAGTCTAAGGATACGCCTG
TTCAATTTTTCTCTCAAATTACTAAGCTGCTTATTATACATAATCCGA
GTACTACTAGAAACCCTTCACAAGGAAATGAATGGTCTCATATCTTT
TGGGTGAACAGAAGTCTACCTTTGTGGGGCTTACAGGTTTCAGTGGCA
TTGATAAGTCTGTTTGAAACAATATTACTTGGTTATCTTAGTTATAAG
GGAAACATCTGGGAACAGATTTTACGAATACCCTTCATCTTGGAAATA
ATTAATGCAGTTCCCTTCATTATCTCAATATTCTGGCCTTCCTTAAGG
AATCTATTTGTCCCAGTCTTTCTGAACTGTTGGCTTGCCAAACATGCC
TTGGAAAATATGATTAATGATCTACACAGAGCCATTCAGCGTACACAG
TCTGCAATGTTTAATCAAGTTTTGATTTTAATATCTACATTACTATGC
CTTATCTTCACCTGCATTTGTGGGATCCAACATCTGGAACGAATAGGA
AAGAAGCTGAATCTCTTTGACTCCCTTTATTTCTGCATTGTGACGTTT
TCTACTGTGGGCTTCGGGGATGTCACTCCTGAAACATGGTCCTCCAAG
CTTTTTGTAGTTGCTATGATTTGTGTTGCTCTTGTGGTTCTACCCATA
CAGTTTGAACAGCTGGCTTATTTGTGGATGGAGAGACAAAAGTCAGGA
GGAAACTATAGTCGACATAGAGCTCAAACTGAAAAGCATGTCGTCCTG
TGTGTCAGCTCACTGAAGATTGATTTACTTATGGATTTTTTAAATGAA
TTCTATGCTCATCCTAGGCTCCAGGATTATTATGTGGTGATTTTGTGT
CCTACTGAAATGGATGTACAGGTTCGAAGGGTACTGCAGATTCCAATG
TGGTCCCAACGAGTTATCTACCTTCAAGGTTCAGCCCTTAAAGATCAA
```

-continued

```
GACCTATTGAGAGCAAAGATGGATGACGCTGAGGCCTGTTTTATTCTC
AGTAGCCGTTGTGAAGTGGATAGGACATCATCTGATCACCAAACAATT
TTGAGAGCATGGGCTGTGAAAGATTTTGCTCCAAATTGTCCTTTGTAT
GTCCAGATATTAAAGCCTGAAAATAAATTTCACATCAAATTTGCTGAT
CATGTTGTTTGTGAAGAAGAGTTTAAATACGCCATGTTAGCTTTAAAC
TGTATATGCCCAGCAACATCTACACTTATTACACTACTGGTTCATACC
TCTAGAGGGCAAGAAGGCCAGCAATCGCCAGAACAATGGCAGAAGATG
TACGGTAGATGCTCCGGGAATGAAGTCTACCACATTGTTTTGGAAGAA
AGTACATTTTTTGCTGAATATGAAGGAAAGAGTTTTACATATGCCTCT
TTCCATGCACACAAAAAGTTTGGCGTCTgCTTGATTGGTGTTAGGAGG
GAGGATAATAAAAACATTTTGCTGAATCCAGGTCCTCGATACATTATG
AATTCTACAGACATATGCTTTTATATTAATATTACCAAAGAAGAGAAT
TCAGCATTTAAAAACCAAGACCAGCAGAGAAAAGCAATGTGTCCAGG
TCGTTTTATCATGGACCTTCCAGATTACCTGTACATAGCATAATTGCC
AGCATGGGTACTGTGGCTATAGACTTGCAAGATACAAGCTGTAGATCA
GCAAGTGGCCCTACCCTGTCTCTTCCTACAGAGGGAAGCAAAGAAATA
AGAAGACCTAGCATTGCTCCTGTTTTAGAGGTTGCAGATACATCATCG
ATTCAAACATGTGATCTTCTAAGTGACCAATCAGAAGATGAAACTACA
CCAGATGAAGAAATGTCTTCAAACTTAGAGTATGCTAAAGGTTACCCA
CCTTATTCTCCATATATAGGAAGTTCACCCACTTTTTGTCATCTCCTT
CATGAAAAAGTACCATTTTGCTGCTTAAGATTAGACAAGAGTTGCCAA
CATAACTACTATGAGGATGCAAAAGCCTATGGATTCAAAAATAAACTA
ATTATAGTTGCAGCTGAAACAGCTGGAAATGGATTATATAACTTTATT
GTTCCTCTCAGGGCATATTATAGACCAAAGAAAGAACTTAATCCCATA
GTACTGCTATTGGATAACCCGCCAGATATGCATTTTCTGGATGCAATC
TGTTGGTTTCCAATGGTTTACTACATGGTGGGCTCTATTGACAACCTA
GATGACTTACTCAGGTGTGGAGTGACTTTTGCTGCTAATATGGTGGTT
GTGGATAAAGAGAGCACCATGAGTGCCGAGGAAGACTACATGGCAGAT
GCCAAAACCATTGTGAACGTGCAGACACTCTTCAGGTTGTTTTCCAGT
CTCAGTATTATCACAGAGCTAACTCACCCCGCCAACATGAGATTCATG
CAATTCAGAGCCAAAGACTGTTACTCTCTTGCTCTTTCAAAACTGGAA
AAGAAAGAACGGGAGAGAGGCTCTAACTTGGCCTTTATGTTTCGACTG
CCTTTTGCTGCTGGGAGGGTGTTTAGCATCAGTATGTTGGACACTCTG
CTGTATCAGTCATTTGTGAAGGATTATATGATTTCTATCACGAGACTT
CTGTTGGGACTGGACACTACACCAGGATCTGGGTTTCTTGTTCTATG
AAAATCACTGCAGATGACTTATGGATCAGAACTTATGCCAGACTTTAT
CAGAAGTTGTGTTCTTCTACTGGAGATGTTCCCATTGGAATCTACAGG
ACTGAGTCTCAGAAACTTACTACATCTGAGTCTCAAATATCTATCAGT
GTAGAAGAGTGGGAAGACACCAAAGACTCCAAAGAACAAGGGCACCAC
CGCAGCAACCACCGCAACTCAACATCCAGTGACCAGTCGGACCATCCC
```

-continued

```
TTGCTGCGGAGAAAAAGCATGCAGTGGGCCCGAAGACTGAGCAGAAAA
GGCCCAAAACACTCTGGTAAAACAGCTGAAAAAATAACCCAGCAGCGA
CTGAACCTCTACAGGAGGTCAGAAAGACAAGAGCTTGCTGAACTTGTG
AAAAATAGAATGAAACACTTGGGTCTTTCTACAGTGGGATATGATGAA
ATGAATGATCATCAAAGTACCCTCTCCTACATCCTGATTAACCCATCT
CCAGATACCAGAATAGAGCTGAATGATGTTGTATACTTAATTCGACCA
GATCCACTGGCCTACCTTCCAAACAGTGAGCCCAGTCGAAGAAACAGC
ATCTGCAATGTCACTGGTCAAGATTCTCGGGAGGAAACTCAACTTTGA
```

SEQ ID NO: 4-Human Slo4 amino acid sequence

```
MVDLESEVPPLPPRYRFRDLLLGDQGWQNDDRVQVEFYMNENTFKERL
KLFFIKNQRSSLRIRLFNFSLKLLSCLLYIIRVLLENPSQGNEWSHIF
WVNRSLPLWGLQVSVALISLFETILLGYLSYKGNIWEQILRIPPFILEI
INAVPFIISIFWPSLRNLFVPVFLNCWLAKHALENMINDLHRAIQRTQ
SAMFNQVLILISTLLCLIFTCICGIQHLERIGKKLNLFDSLYFCIVTF
STVGFGDVTPETWSSKLFVVAMICVALVVLPIQFEQLAYLWMERQKSG
GNYSRHRAQTEKHVVLCVSSLKIDLLMDFLNEFYAHPRLQDYYVVILC
PTEMDVQVRRVLQIPMWSQRVIYLQGSALKDQDLLRAKMDDAEACFIL
SSRCEVDRTSSDHQTILRAWAVKDFAPNCPLYVQILKPENKFHIKFAD
HVVCEEEFKYAMLALNCICPATSTLITLLVHTSRGQEGQQSPEQWQKM
YGRCSGNEVYHIVLEESTFFAEYEGKSFTYASFHAHKKFGVCLIGVRR
EDNKNILLNPGPRYIMNSTDICFYINITKEENSAFKNQDQQRKSNVSR
SFYHGPSRLPVHSIIASMGTVAIDLQDTSCRSASGPTLSLPTEGSKEI
RRPSIAPVLEVADTSSIQTCDLLSDQSEDETTPDEEMSSNLEYAKGYP
PYSPYIGSSPTFCHLLHEKVPFCCLRLDKSCQHNYYEDAKAYGFKNKL
IIVAAETAGNGLYNFIVPLRAYYRPKKELNPIVLLLDNPPDMHFLDAI
CWFPMVYYMVGSIDNLDDLLRCGVTFAANMVVVDKESTMSAEEDYMAD
AKTIVNVQTLFRLFSSLSIITELTHPANMRFMQFRAKDCYSLALSKLE
KKERERGSNLAFMFRLPFAAGRVFSISMLDTLLYQSFVKDYMISITRL
LLGLDTTPGSGFLCSMKITADDLWIRTYARLYQKLCSSTGDVPIGIYR
TESQKLTTSESQISISVEEWEDTKDSKEQGHHRSNHRNSTSSDQSDHP
LLRRKSMQWARRLSRKGPKHSGKTAEKITQQRLNLYRRSERQELAELV
KNRMKHLGLSTVGYDEMNDHQSTLSYILINPSPDTRIELNDVVYLIRP
DPLAYLPNSEPSRRNSICNVTGQDSREETQL
```

What is claimed is:

1. An isolated Slo2 polypeptide comprising an alpha subunit of a Slo potassium channel, the polypeptide:
   (i) forming, with at least one additional Slo alpha subunit, a Slo potassium channel comprising the characteristic of voltage-gating; and
   (ii) comprising a sequence having an amino acid sequence having at least 95% sequence identity to SEQ ID NO:2.

2. The polypeptide of claim 1, wherein the potassium channel further comprises the characteristic of rapid activation.

3. The polypeptide of claim 1, wherein the polypeptide has a molecular weight of between about 134 kD to about 144 kD.

4. The polypeptide of claim 1, wherein the polypeptide comprises an alpha subunit of a homomeric potassium channel.

5. The polypeptide of claim 1, wherein the polypeptide comprises an alpha subunit of a heteromeric potassium channel.

6. The polypeptide of claim 1, wherein the polypeptide comprises the amino acid sequence of SEQ ID NO:2.

7. The polypeptide of claim 1, wherein the polypeptide consists of the amino acid sequence of SEQ ID NO:2.

* * * * *